United States Patent [19]

Unger et al.

[11] Patent Number: 6,033,645
[45] Date of Patent: Mar. 7, 2000

[54] METHODS FOR DIAGNOSTIC IMAGING BY REGULATING THE ADMINISTRATION RATE OF A CONTRAST AGENT

[76] Inventors: Evan C. Unger, 13365 E. Camino LaCebadilla, Tucson, Ariz. 85749; Terry Matsunaga, 751 S. Front Royal, Tucson, Ariz. 85710; Thomas A. Fritz, 5442 E. 8th St., Tucson, Ariz. 85711; Varadarajan Ramaswami, 7727 E. 8th St., Tucson, Ariz. 85715

[21] Appl. No.: 08/666,129

[22] Filed: Jun. 19, 1996

[51] Int. Cl.[7] .................................................. A61K 49/00
[52] U.S. Cl. ..................... 424/9.5; 424/9.51; 424/9.52; 424/450
[58] Field of Search ........................ 424/9.5, 450, 9.51, 424/9.52

[56] References Cited

U.S. PATENT DOCUMENTS

| | | | |
|---|---|---|---|
| 3,015,128 | 1/1962 | Somerville, Jr. | 18/2.6 |
| 3,291,843 | 12/1966 | Fritz et al. | 260/614 |
| 3,293,114 | 12/1966 | Kenaga et al. | 162/168 |
| 3,401,475 | 9/1968 | Morehouse et al. | 40/306 |
| 3,401,680 | 9/1968 | Unterstenhoefer et al. | 126/91 |
| 3,479,811 | 11/1969 | Walters | 57/153 |
| 3,488,714 | 1/1970 | Walters et al. | 161/161 |
| 3,557,294 | 1/1971 | Dear et al. | 424/342 |
| 3,594,326 | 7/1971 | Himmel et al. | 252/316 |
| 3,615,972 | 10/1971 | Morehouse, Jr. et al. | 156/79 |
| 3,650,831 | 3/1972 | Jungermann et al. | 134/27 |
| 3,732,172 | 5/1973 | Herbig et al. | 252/316 |
| 3,873,564 | 3/1975 | Schneider et al. | 260/309.6 |
| 3,945,956 | 3/1976 | Garner | 260/2.5 |
| 3,968,203 | 7/1976 | Spitzer et al. | 424/47 |
| 4,027,007 | 5/1977 | Messina | 424/46 |
| 4,089,801 | 5/1978 | Schneider | 252/316 |
| 4,108,806 | 8/1978 | Cohrs et al. | 521/54 |
| 4,162,282 | 7/1979 | Fulwyler et al. | 264/9 |
| 4,179,546 | 12/1979 | Garner et al. | 521/56 |
| 4,192,859 | 3/1980 | Mackaness et al. | 424/5 |
| 4,224,179 | 9/1980 | Schnieder | 252/316 |
| 4,229,360 | 10/1980 | Schneider et al. | 260/403 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,342,826 | 8/1982 | Cole | 435/7 |
| 4,344,929 | 8/1982 | Bonsen et al. | 424/15 |
| 4,420,442 | 12/1983 | Sands | 264/13 |
| 4,421,562 | 12/1983 | Sands | 106/75 |
| 4,426,330 | 1/1984 | Sears | 260/403 |
| 4,427,649 | 1/1984 | Dingle et al. | 424/38 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,532,500 | 10/1970 | Priest et al. | 96/91 |
| 4,533,254 | 8/1985 | Cook et al. | 366/176 |
| 4,534,899 | 8/1985 | Sears | 260/403 |
| 4,540,629 | 9/1985 | Sands et al. | 428/402 |
| 4,544,545 | 10/1985 | Ryan et al. | 424/1.1 |

(List continued on next page.)

FOREIGN PATENT DOCUMENTS

| | | |
|---|---|---|
| 641363 | 3/1990 | Australia . |
| B-30351/89 | 3/1993 | Australia . |
| 0 052 575 | 5/1982 | European Pat. Off. . |
| 0 107 559 | 5/1984 | European Pat. Off. . |
| 0 077 752 B1 | 3/1986 | European Pat. Off. . |
| 0 243 947 | 4/1987 | European Pat. Off. . |
| 0 231 091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357163 A1 | 3/1990 | European Pat. Off. . |

(List continued on next page.)

OTHER PUBLICATIONS

Seibyl, Biois #94:339104, 1994.
Galjee, Biosis #91:493622, 1991.
Uemura, Biosis #80: 105491, 1979.
Uemura, Embase, #79180131, 1979
Shinoda, K., et al., "The Formation of Micelles", *Colloidal Surfactant,* Academic Press, New York, 1963, Chapter 1, 1–88.
Deasy, P.D., "Polymerization Procedures for Nonbiodegradable Micro–and Nanocapsules and Particles", *Microencapsulation and Related Drug Processes,* Marcel Dekker, Inc., New York, 1984, 9, 195–218.
Deasy, P.D., "Polymerization Procedures for Biodegradable Micro–and Nanocapsules and Particles", *Microencapsulation and Related Drug Processes,* Marcel Dekker, Inc., New York, 1984, 10, 219–240.
Chang et al., "Semipermeable Aqueous Microcapsules", *Canadian J. of Physiology and Pharmocology,* 1966, 44, 115–128.
Chang, "Semipermeable Microcapsules", *Science,* 1964, 146, 524–525.
Ulendorf, "Physics of Ultrasound Contrast Imaging: Scattering in the Linear Range", *IEEE Transactions on Ultrasonics, Ferrolectrics, and Frequency Control,* 1994, 41(1), 70–79.
Sutherland et al., "Color Doppler Myocardial Imaging: A New Technique for the Assessment of Myocardial Function", *J. Am. Soc. of Echocardiogr,* 1994, 7(5), 441–458.

(List continued on next page.)

*Primary Examiner*—Johann Richter
*Assistant Examiner*—Patrick R. Delaney

[57] ABSTRACT

Methods for providing an image of an internal region of a patient. Embodiments of the methods involve administering to the patient a contrast agent which comprises a vesicle composition comprising, in an aqueous carrier, a gas or gaseous precursor and vesicles comprising lipids, proteins or polymers. The patient is scanned using diagnostic imaging, such as ultrasound, to obtain a visible image of the region. The contrast agent is administered to the patient at a rate to substantially eliminate diagnostic artifacts in the image. The methods are particularly useful for diagnosing the presence of any diseased tissue in the patient.

240 Claims, 1 Drawing Sheet

U.S. PATENT DOCUMENTS

| | | | |
|---|---|---|---|
| 4,549,892 | 10/1985 | Baker et al. | 65/21.4 |
| 4,569,836 | 2/1986 | Gordon . | |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,663,161 | 5/1987 | Mannino et al. | 424/89 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,693,999 | 9/1987 | Axelsson et al. | 514/174 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,834,964 | 5/1989 | Rosen | 424/9 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/339 |
| 4,895,719 | 1/1990 | Radhakrishnan | 424/45 |
| 4,898,734 | 2/1990 | Mathiowitz et al. | 424/426 |
| 4,900,540 | 2/1990 | Ryan et al. | 424/9 |
| 4,918,065 | 4/1990 | Stindl et al. | 514/179 |
| 4,919,895 | 4/1990 | Heldebrant et al. | 422/129 |
| 4,921,706 | 5/1990 | Roberts et al. | 424/450 |
| 4,927,623 | 5/1990 | Long, Jr. | 424/5 |
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,984,573 | 1/1991 | Leunbach | 128/653 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,004,611 | 4/1991 | Leigh | 424/450 |
| 5,008,050 | 4/1991 | Cullis et al. | 264/4.3 |
| 5,008,109 | 4/1991 | Tin | 424/422 |
| 5,013,556 | 5/1991 | Woodle et al. | 424/450 |
| 5,045,304 | 9/1991 | Schneider et al. | 424/9 |
| 5,049,388 | 9/1991 | Knight et al. | 424/450 |
| 5,088,499 | 2/1992 | Unger | 128/662.2 |
| 5,107,842 | 4/1992 | Levene et al. | 128/662.02 |
| 5,114,703 | 5/1992 | Wolf et al. | 424/5 |
| 5,123,414 | 6/1992 | Unger | 28/654 |
| 5,135,000 | 8/1992 | Akselrod et al. | 128/662.02 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,196,348 | 3/1993 | Schweighardt et al. | 436/173 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,247,935 | 9/1993 | Cline et al. | 128/653.2 |
| 5,271,928 | 12/1993 | Schneider et al. | 424/9 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,339,814 | 8/1994 | LAsker | 128/653.4 |
| 5,344,930 | 9/1994 | Piess et al. | 544/84 |
| 5,350,571 | 9/1994 | Kaufman et al. | 424/9 |
| 5,352,435 | 10/1994 | Unger | 424/9 |
| 5,362,477 | 11/1994 | Moore et al. | 424/9 |
| 5,368,840 | 10/1997 | Unger | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.1 |
| 5,469,854 | 11/1995 | Unger et al. | 128/662.02 |
| 5,470,582 | 11/1995 | Supersaxo et al. | 424/489 |
| 5,485,839 | 1/1996 | Aida et al. | 128/653.1 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,505,932 | 4/1996 | Grinstaff et al. | 424/9.3 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,545,396 | 8/1996 | Albert et al. | 424/93 |
| 5,552,133 | 9/1996 | Lambert et al. | 424/9.52 |
| 5,552,155 | 9/1996 | Bailey et al. | 424/450 |
| 5,556,610 | 9/1996 | Yan et al. | 424/9.52 |
| 5,558,856 | 9/1996 | Klaveness et al. | 424/9.37 |
| 5,560,364 | 10/1996 | Porter | 128/662.02 |
| 5,562,893 | 10/1996 | Lohrmann | 424/9.52 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,569,448 | 10/1996 | Wong et al. | 424/9.45 |
| 5,569,449 | 10/1996 | Klaveness et al. | 424/9.51 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,593,680 | 1/1997 | Bara et al. | 424/401 |
| 5,605,673 | 2/1997 | Schutt et al. | 424/9.51 |
| 5,614,169 | 3/1997 | Klaveness et al. | 424/9.52 |
| 5,620,689 | 4/1997 | Allen et al. | 424/178.1 |
| 5,626,833 | 5/1997 | Schutt et al. | 424/9.52 |
| 5,639,443 | 6/1997 | Schutt et al. | 424/9.52 |
| 5,643,553 | 7/1997 | Schneider et al. | 424/9.52 |
| 5,672,585 | 9/1997 | Pierschbacher et al. | 514/11 |
| 5,676,928 | 10/1997 | Klaveness et al. | 424/9.32 |
| 5,679,459 | 10/1997 | Riess et al. | 428/402.2 |
| 5,686,060 | 11/1997 | Schneider et al. | 424/9.52 |

| | | |
|---|---|---|
| 5,686,102 | 11/1997 | Gross et al. .......................... 424/450 |
| 5,707,606 | 1/1998 | Quay .................................. 424/9.52 |
| 5,707,607 | 1/1998 | Quay .................................. 424/9.52 |
| 5,711,933 | 1/1998 | Bichon et al. ...................... 424/9.52 |
| 5,716,597 | 2/1998 | Lohrmann et al. ................... 424/9.5 |
| 5,732,707 | 3/1998 | Widder et al. ................... 128/661.08 |
| 5,733,527 | 3/1998 | Schutt ............................... 424/9.52 |
| 5,740,807 | 4/1998 | Porter ............................. 128/662.02 |
| 5,804,162 | 9/1998 | Kabalnov et al. .................. 424/9.51 |
| 5,840,023 | 11/1998 | Oraevsky et al. .................. 600/407 |
| 5,855,865 | 1/1999 | Lambert et al. ................... 424/9.52 |

FOREIGN PATENT DOCUMENTS

| | | |
|---|---|---|
| 0 361 894 | 4/1990 | European Pat. Off. . |
| 0 216 730 | 1/1991 | European Pat. Off. . |
| 0 467 031 A2 | 5/1991 | European Pat. Off. . |
| 441468 A2 | 8/1991 | European Pat. Off. . |
| 0 357 164 B1 | 10/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 586 875 | 3/1994 | European Pat. Off. . |
| 0 614 656 A1 | 9/1994 | European Pat. Off. . |
| 0 727 225 A2 | 8/1996 | European Pat. Off. . |
| 2 700 952 | 8/1994 | France . |
| 25 21 003 | 8/1976 | Germany . |
| 62 286534 | 12/1987 | Japan . |
| 63-60943 | 3/1988 | Japan . |
| 1044680 | 10/1966 | United Kingdom . |
| 2193095 | 2/1988 | United Kingdom . |
| WO 80/02365 | 11/1980 | WIPO . |
| WO 82/01642 | 5/1982 | WIPO . |
| 85/01161 | 3/1985 | WIPO . |
| WO 86/00238 | 1/1986 | WIPO . |
| WO 86/01103 | 2/1986 | WIPO . |
| WO 89/05040 | 6/1989 | WIPO . |
| WO 90/04384 | 5/1990 | WIPO . |
| WO 90/04943 | 5/1990 | WIPO . |
| WO 91/00086 | 1/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/15284 | 9/1992 | WIPO . |
| WO 92/17212 | 10/1992 | WIPO . |
| WO 92/17213 | 10/1992 | WIPO . |
| WO 92/17436 | 10/1992 | WIPO . |
| WO 92/17514 | 10/1992 | WIPO . |
| WO 92/21382 | 10/1992 | WIPO . |
| WO 92/22249 | 12/1992 | WIPO . |
| WO 92/22298 | 12/1992 | WIPO . |
| WO 93/00933 | 1/1993 | WIPO . |
| WO 93/05819 | 1/1993 | WIPO . |
| WO 93/06869 | 4/1993 | WIPO . |
| WO 93/13809 | 7/1993 | WIPO . |
| WO 93/17718 | 9/1993 | WIPO . |
| WO 93/20802 | 10/1993 | WIPO . |
| WO 94/00110 | 1/1994 | WIPO . |
| WO 94/06477 | 3/1994 | WIPO . |
| WO 94/07539 | 4/1994 | WIPO . |
| WO 94/09829 | 5/1994 | WIPO . |
| WO 84/02909 | 8/1994 | WIPO . |
| WO 94/16739 | 8/1994 | WIPO . |
| WO 94/21302 | 9/1994 | WIPO . |
| WO 94/28780 | 12/1994 | WIPO . |
| WO 94/28873 | 12/1994 | WIPO . |
| WO 95/06518 | 3/1995 | WIPO . |
| WO 95/07072 | 3/1995 | WIPO . |
| WO 95/23615 | 9/1995 | WIPO . |
| WO 95/24184 | 9/1995 | WIPO . |
| WO 96/04018 | 2/1996 | WIPO . |
| WO 96/09793 | 4/1996 | WIPO . |
| WO 96/40281 | 12/1996 | WIPO . |
| WO 98/00172 | 1/1998 | WIPO . |

OTHER PUBLICATIONS

Kawabata, K. et al., "Effect of second–harmonic superimposition on efficient induction of sonochemical effect", *Ultrasonics Sonochemistry,* 1966, 3, 1–5.

Villanueva et al., "Characterization of Spatial Patters of Flow Within the Reperfused Myocardium by Myocardial Contrast Echocardiography", *Circulation,* vol. 88, No. 6, pp. 2596–2606 (Dec. 1993).

Desir et al., "Assessment of regional myocardial perfusion with myocardial contrast echocardiography in a canine model of varying degrees of coronary stenosis", *Am. Heart J.,* Jan., 1994, 127(1), 56–63.

Sekins et al., "Lung Cancer Hyperthermia via Ultrasound and PFC Liquids", Published Pietersen, "A New Warning System for Fires of Electrical Origin", CERN European Organization for Nuclear Research, Health and Safety Division, Mar., 1977, 1–5.

PCT International Search Report dated Nov. 12, 1997, 1 page.

Reexamination of U.S. Patent No. 5527521, Reexam Control No. 90/004,719.

Reexamination of U.S. Patent No. 5,547656, Reexam Control No. 90/004,720.

Nomura et al., "US Contrast Enhancement of Hepatic Tumor with Helium Gas Microbubbles: A Preliminary Report", *Jpn. J. Med. Ultrasonics,* 1991, 18(5), (Japanese with Engligh language abstract).

Hynynen et al., "The Ysefulness of a Contrast Agent and Gradient Recalled Acquisition in a Steady–State Imaging Sequence for Magnetic Resonance Imaging–Guided Noninvasive Ultrasound Surgery", *Investigative Radiology,* 1994, 29(10), 897–903.

Linder et al., "Myocardial Perfusion Characteristics and Hemodynamic Profile of MRX–115, a Venous Echocardiographic Contrast Agent, During Acute Myocardial Infarction", *J. Am. Soc. Enchocardiography,* 1998, 11(1), 36–46.

Regen et al., "Polymerized Phosphatidylcholine Vesicles, Synthesis and Characterization", *J. Am. Chem. Soc.,* 1982, 104(3), 191–195.

Wei et al., "Quantification of Myocardial Blood Flow with Ultrasound–Induced Destruction of Microbubbles Administered as a Constant Venous Infusion", *Circulation,* 1998, 97, 473–483.

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry,* vol. 13, No. 3, pp. 568–574 (1974).

Thanassi, "Aminomalonic Acid: Spontaneous Decarboxylation and Reaction with 5–Deoxypyridoxal", *Biochemistry,* vol. 9, No. 3, pp. 525–532 (1970).

Stelmashok et al., *Koordinatsionnaya Khimiya,* vol. 3, No. 4, pp. 524–527 (1977) (Russian and English language versions).

Mayhew et al., "High–Pressure Continuous–Flow System for Drug Entrapment in Liposomes", *Methods in Enzymology,* vol. 149, pp. 64–77 (1987).

Mayhew et al., "Characterization of Liposomes Prepared Using a Microemulsifier", *Biochimica et Biophysica Acta,* vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812:55–65 (1985).

Mayer et al., "Vesicles of Variable Size PRoduced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Enchcardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophses of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.*, vol. 23, pp S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems—Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250 (3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1–18, 29–35, 51–65 and 79–107 (CRC Press Inc., Boca Raton, FL, 1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiaby Low–frequency Synthesized Ultrasound", *IEEE Engineering*, pp. 879–880, vol. 2 (1988) (abstract).

McAvoy et al., *IEEE Engineering*, Ultrasonics Symposium Proceedings, vol. 2, pp. 677–1248 (1989) (abstract).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.,* 1965, 13:238–252.

Carson et al., *Ultrasound in Med. & Biol.* 3, 1978, 341–350.

deGier et al., "Relations Between Liposomes and Biomembranes", *Annals of The New York Academy of Sciences,* 1978, 308:85–99.

Felgner et al., "Lipofection: A highly efficient, lipid–mediated DNA–transfection procedure", *Proc. Natl. Acad. Sci.,* 1987, 84:7413–7417.

Gabizon et al., "Liposome formulations with prolonged circulation time in blood and enhanced uptake by tumors", *Proc. Natl. Acad. Sci.,* 1988, 85:6949–6953.

Garelli, et al., *Biochimica et Biophysica Acta,* vol. 1127:41–48 (1992).

Kawai et al., "New Procedure for DNA Transfection with Polycation and Dimethyl Sulfoxide", *Molecular and Cellular Biology,* 1984, 4:1172–1174.

Kuo et al., "Metallocene Antitumor Agents. Solution and Solid–State Molybdenocene Coordination . . . ", *J. Am. Chem. Soc.,* 1991, 113:9027–9045.

*Mammalian Cell Biotechnology: A Practical Approach,* M. Butler, 1991 (Oxford University Press, New York), p. 57–70.

Mathiowitz et al., "Photochemical Rupture of Microcapsules: A Model System", *Journal of Applied Polymer Science,* 1981, 26:809–822.

May et al., "Cationic Liposomes Enable Bovine Herpesvirus Type 2 DNA to Infect Cells", *Acta virol.,* 1991, 35:107.

Poznansky et al., "Biologica Approaches to the Controlled Delivery of Drugs: A Critical Review", *Pharmacol, Rev.,* 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature,* 1992, 359:67–70.

Thompson, Larry, "At Age 2, Gene Therapy Enters a Growth Phase", *Science* 1992, 258:744–746.

Trubetskoy et al., "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE,* 1992, O–7803–0785, pp. 354–355.

Williams, "Human Gene Therapy: Searching for Better Vectors", *ASM News* [American Society for Microbology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science,* vol. 35, pp. 755–774 (1988).

Sankaram et al., "Cholesterol–Induced Fluid–Phase Immiscibility in Membranes", *Proc. Natl. Acad. Sci.,* vol. 88, pp. 8686–8690 (1991).

*Scientific Apparatus Catalog 92/93* (VWR Scientific, 1991), "Syringes", pp. 1511–1513; "Filtration, Syringe Filters", pp. 766–768; "Filtration, Membranes", pp. 750–753; "Filtration, Filter Holders", p. 744.

Gramiak et al., *Radiology,* "Detection of Intracardiac Blood Flow by Pulsed Echo–Ranging", pp. 415–418 (1971).

Feigenbaum et al., *Circulation,* "Identification of Ultrasound Echoes from the Left Ventricle by Use of Intracardiac Injections of Indocyanine Green", vol. XL1, pp. 615–621 (1970).

Santaella, et al., *FEBS 13463,* "Extended In Vivo Blood Circulation Time of Fluorinated Liposomes", vol. 336, No. 3, pp. 481–484 (1993).

Kost, et al., "Ultrasonic Modulated Drug Delivery Systems", *Polymers in Medicine II: Biomedical and Pharmaceutical Applications,* Chielline E. (ed.), (Plenum Press, New York and London), pp. 387–396 (1988).

Brown and Langer, *Annual Review Medicine,* 1988, 39:221 29, Annual Review, Inc., "Transdermal Delivery of Drugs", pp. 221–229.

Moseley, et al., *Microbubbles: A Novel MR Susceptibility Contrast Agent,* abstract, 1991 Napa, California Meeting of the Society for Magnetic Resonance in Medicine.

Ter–Pogossia *Tomography,* Kee, et al., n, "Physical Principles and Instrumentation", *Computed Body* eds., Raven Press, New York, Chapter 1, pp. 1–7 (1988).

Aronberg, "Techniques", *Computed Body Tomography,* Kee, et al., eds., Raven PRess, New York, Chapter 2, pp. 9–36 (1988).

Miller, *Ultrasonics* (Sep. 1981), "Ultrasonic detection of resonant cavitation bubbles in a flow tube by their second–harmonic emissions," pp. 217–244.

Dittrich, "Cardiac Muscle Ischemia and Infarction", The Second Annual International Symposium on Contrast Agents in Diagnostic Ultrasound, Atlantic City, NJ (May 7, 1996) (abstract).

Pantely, "Intravenous Contrast Echocardiography—Tissue Imaging & Quantification of Coronary Blood Flow", The Second Annual International Symposium on Contrast Agents in Diagnostic Ultrasound, Atlantic City, NJ (May 7, 1996) (Abstract).

Schutt et al., "Osmotically Stabilized Microbubble Sonographic Contrast Agents",*Acad. Radiol.,* vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta,* 1192, pp. 61–70 (1994).

Frézard, et al., "Fluorinated Phospholipid–Based Vesicles as Potential Drug Carriers: Encapsulation/Sustaining of Drugs and Stability in Human Serum", *Art., Cells, Blood Subs., and Immob. Biotech.,* 22(4), pp. 1403–1408 (1994).

Canfield et al., "Incorporation of β–Carotene into Mixed Micelles", *Methods in Enzymology,* 1990, 189, 418–422.

Elgorab et al., "Solubilization of β–Carotene and Retinol in Aqueous Solutions of Mixed Micelles", *Biochem. Biophys. Acta.,* 1973, 306, 58–66.

Feinstein, Steven B., "Myocardial Perfusion Imaging: Contrast Echocardiography Today and Tomorrow," *Journal of the American College of Cardiology,* 8,(1):251–253 (1986).

Keller et al., "The Behavior of Sonicated Albumin Microbubbles Within the Microcirculation: A Basis for Their Use During Myocardial Contrast Echocardiography", *Circulation Res.,* 65(2) :458465 (1989).

Lincoff et al., "Perfluoro–n–butane: A Gas for Maximum Duration Retinal Tamponade," *Arch Ophthalmology,* 101:460–462 (1983).

*Remington's Pharmaceutical Sciences,* John Hoover, managing ed., Mack Publishing Company, Easton, PA, pp. 295–298, 736; 1242–1244 (1975).

*Handbook of Pharmaceutical Excipients,* American Pharmaceutical Association, Washington, D.C. and The Parmaceutical Society of Great Britain, London, England, pp. 181–183 (1986).

Barnhart et al., "Characteristics of Albunex™: Air–Filled Microspheres for Echocardiography Contrast Enhancement," *Investigative Radiology,* 25:S162–164 (1988).

Levene et al., "Characterization of Albunex™," *J. acoust. Soc. Am.,* 87(Suppl.1):569–70 (1987).

Miller et al., "Physiochemical Approaches to the Mode of Action of General Anesthetics," *J. Amer. Soc. Anesthesiologists,* 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

PR Newswire, Apr. 1, 1986.

Swanson et al., Chapter 22, "Enhancement Agents for Ultrasound: Fundamentals", *Pharmaceuticals In Medical Imaging,* pp. 682–687 (1990).

Ophir et al., "Contrast Agents in Diagnostic Ultrasound", *Ultrasound in Med. & Biol.,* vol. 15, No. 4, pp. 319–333 (1989).

Jacobs, "Intraocular gas measurement using A–scan ultrasound", *Current Eye Research,* vol. 5, No. 8, pp. 575–578 (1986).

METHODS FOR DIAGNOSTIC IMAGING BY REGULATING THE ADMINISTRATION RATE OF A CONTRAST AGENT

FIELD OF THE INVENTION

The present invention relates to improved methods for diagnostic imaging. More particularly, the present invention relates to improved methods for diagnostic imaging which involve the regulation of the rate at which a contrast agent is administered to a patient.

BACKGROUND OF THE INVENTION

Ultrasound is a valuable diagnostic imaging technique for studying various areas of the body including, for example, the vasculature, such as tissue microvasculature. Ultrasound provides certain advantages over other diagnostic techniques. For example, diagnostic techniques involving nuclear medicine and X-rays generally results in exposure of the patient to ionizing electron radiation. Such radiation can cause damage to subcellular material, including deoxyribonucleic acid (DNA), ribonucleic acid (RNA) and proteins. Ultrasound does not involve such potentially damaging radiation. In addition, ultrasound is relatively inexpensive as compared to other diagnostic techniques, such as magnetic resonance imaging (MRI), which can require elaborate and expensive equipment.

Ultrasound involves the exposure of a patient to sound waves. Generally, the sound waves dissipate due to absorption by body tissue, penetrate through the tissue, or reflect off of the tissue. The reflection of sound waves off of tissue, generally referred to as backscatter or reflectivity, forms the basis for developing an ultrasound image. This is because sound waves reflect differentially from different body tissues. This differential reflection is due to various factors, including the constituents and the density of the particular tissue being observed. The differentially reflected waves are then detected, usually with a transducer which can detect sound waves having a frequency of from 1 megahertz (MHz) to ten MHz. The detected waves are integrated, quantitated and converted into an image of the tissue being studied.

Ultrasound imaging techniques often involve the use of contrast agents. Contrast agents can serve to improve the quality and usefulness of images which are obtained with ultrasound. Certain exemplary contrast agents include, for example, suspensions of solid particles and emulsified liquid droplets.

The reflection of sound from a liquid-gas interface is extremely efficient.

Accordingly, certain bubbles, including certain gas-filled bubbles, can be highly useful as contrast agents. The term "bubbles", as used herein, refers to vesicles which are generally characterized by the presence of one or more membranes or walls surrounding an internal void that is filled with a gas or precursor thereto. Exemplary bubbles include, for example, liposomes, micelles and the like.

The effectiveness of bubbles as contrast agents depends upon various factors, including, for example, the size of the bubble. As known to the skilled artisan, the signal which is in the range of diagnostic ultrasound frequencies and which can be reflected off of a bubble is a function of the radius ($r^6$) of the bubble (Rayleigh Scatterer).

Thus, a bubble having a diameter of about 4 micrometer ($\mu$m) possesses about 64 times the scattering ability of a bubble having a diameter of about 2 $\mu$m. Thus, generally speaking, the larger the bubble, the greater the reflected signal.

However, bubble size is limited by the diameter of capillaries through which the bubbles must pass. Generally, contrast agents which comprise bubbles having a diameter of greater than about 10 $\mu$m can be dangerous since microvessels may be occluded. Accordingly, it is desired that greater than about 98% of the bubbles in a contrast agent have a diameter of less than about 10 $\mu$m. Mean bubble diameter is important also, and should be greater than about 1 $\mu$m, with greater than about 2 $\mu$m being preferred. The volume weighted mean diameter of the bubbles should be about 7 to about 20 $\mu$m.

The viability of currently available ultrasound contrast agents and methods involving their use is highly dependent on the concentration of contrast agent which is present at the region being imaged. For example, ultrasound imaging involving excess concentrations of contrast agent or insufficient concentrations of contrast agent can result in the generation of ultrasound images which are unacceptable for diagnostic use. In this connection, an excess concentration of contrast agent generally results in the reflection of an overabundance of sound waves. This overabundance of reflected sound waves can cause diagnostic artifacts including, for example, shadowing or darkening, in the resulting ultrasound image. An insufficient concentration of contrast agent generally results in the reflection of an insufficient amount of sound waves. This insufficient amount of reflected sound waves can also produce diagnostic artifacts, such as excessive lightening or brightening, in the resulting ultrasound image. Methods for regulating the concentration of contrast agent in vivo in connection with diagnostic imaging methods have been unreported heretofore.

In addition to ultrasound, computed tomography (CT) is a valuable diagnostic imaging technique for studying various areas of the body. In CT, the radiodensity (electron density) of matter is measured and is expressed in terms of Hounsefield Units (HU). Hounsefield Units, named after the inventor of the first CT scanner, are an indication of the relative absorption of CT X-rays by matter, the absorption being directly proportional to the electron density of that matter. Water, for example, has a value of 0 HU, air a value of –1000 HU, and dense cortical bone a value of 1000 HU. Because of the similarity in the densities of various tissues in the body, however, it has been necessary to develop contrast agents which can be used to change the relative densities of different tissues. This has resulted in an overall improvement in the diagnostic efficacy of CT.

In the search for contrast agents for CT, researchers have generally sought to develop agents that will increase electron density in certain areas of a region of the body (positive contrast agents). Barium and iodine compounds, for example, have been developed for this purpose. For the gastrointestinal tract, barium sulfate is used extensively to increase the radiodensity of the bowel lumen on CT scans. Iodinated water-soluble contrast media are also used to increase density within the gastrointestinal tract, but are not used as commonly as the barium compounds, primarily because the iodine preparations are more expensive than barium and are generally less effective in increasing radiodensity within this region of the body. The use of low density microspheres as CT contrast agents has also been reported. See, e.g., Unger, U.S. Pat. No. 5,205,290.

As discussed above in connection with ultrasound diagnostic methods, the viability of currently available CT contrast agents and methods involving their use is extremely dependent on concentration. For example, too little contrast is observed if the concentration of contrast agent at the region of interest is too low. Conversely, too much contrast is observed if the concentration of contrast agent at the region of interest is too high. In the case of barium and iodine compounds, for example, too high a concentration can cause beam hardening diagnostic artifacts which appear as streaks in the CT images.

Accordingly, new and/or better diagnostic imaging methods which permit the regulation of the concentration of contrast agents are needed. The present invention is directed to this, as well as other, important ends.

SUMMARY OF THE INVENTION

The present invention is directed, in part, to improved methods for diagnostic imaging. Specifically, in one embodiment, there is provided an improved method for providing an image of an internal region of a patient. The method comprises administering to the patient a vesicle composition comprising, in an aqueous carrier, a gas or gaseous precursor and vesicles comprising lipids, proteins or polymers. The patient is scanned using diagnostic imaging to obtain a visible image of the region. The method involves the administration of the vesicle composition at a rate which substantially eliminates diagnostic artifacts in the image. A preferable rate of administration of the vesicle composition is less than about $8 \times 10^6$ vesicles/Kg-sec.

Another embodiment of the invention also relates to a method for providing an image of an internal region of a patient. The method comprises administering to the patient a lipid composition comprising, in an aqueous carrier, a lipid and a gas or gaseous precursor. The patient is scanned using diagnostic imaging to obtain a visible image of the region. The method involves the administration of the lipid composition at a rate which substantially eliminates diagnostic artifacts in the image. A preferable rate of administration of the lipid composition is from about $1 \times 10^{-7}$ to about $3 \times 10^{-3}$ cc gas/Kg-sec.

Still another embodiment of the present invention relates to a method for providing an image of an internal region of a patient. The method comprises administering to the patient a vesicle composition comprising, in an aqueous carrier, a gas or gaseous precursor and vesicles comprising lipids, proteins or polymers. The composition is flushed and the patient is scanned using diagnostic imaging to obtain a visible image of the region. The method involves flushing the composition at a rate which substantially eliminates diagnostic artifacts in the image. A preferable flush rate is less than about 2.5 mL/sec.

Yet another embodiment of the invention relates to a method for providing a diagnostic image of an internal region of a patient. The method comprises administering to the patient a lipid composition comprising, in an aqueous carrier, a lipid and a gas or gaseous precursor. The composition is flushed and the patient is scanned using diagnostic imaging to obtain a visible image of the region. The method involves flushing the composition at a rate which substantially eliminates diagnostic artifacts in the image. A preferable flush rate is less than about 2.5 mL/sec.

In another embodiment of the invention, there is provided a method for diagnosing the presence of diseased tissue in a patient. The method comprises administering to the patient a vesicle composition comprising, in an aqueous carrier, a gas or gaseous precursor and vesicles comprising lipids, proteins or polymers. The patient is scanned using diagnostic imaging to obtain a visible image of any diseased tissue in the patient. The method involves the administration of the vesicle composition at a rate which substantially eliminates diagnostic artifacts in the image. A preferable rate of administration of the vesicle composition is less than about $8 \times 10^6$ vesicles/Kg-sec.

Still another embodiment of the invention relates to a method for diagnosing the presence of diseased tissue in a patient. The method comprises administering to the patient a lipid composition comprising, in an aqueous carrier, a lipid and a gas or gaseous precursor. The patient is scanned using diagnostic imaging to obtain a visible image of any diseased tissue in the patient. The method involves the administration of the lipid composition at a rate which substantially eliminates diagnostic artifacts in the image. A preferable rate of administration of the lipid composition is from about $1 \times 10^{-7}$ to about $3 \times 10^{-3}$ cc gas/Kg-sec.

Yet another embodiment of the invention relates to a method for diagnosing the presence of diseased tissue in a patient. The method comprises administering to the patient a vesicle composition comprising, in an aqueous carrier, a gas or gaseous precursor and vesicles comprising lipids, proteins or polymers. The composition is flushed and the patient is scanned using diagnostic imaging to obtain a visible image of any diseased tissue in the region. The method involves flushing the vesicle composition at a rate which substantially eliminates diagnostic artifacts in the image. A preferable flush rate is less than about 2.5 mL/sec.

Another embodiment of the invention relates to a method for diagnosing the presence of diseased tissue in a patient. The method comprises administering to the patient a lipid composition comprising, in an aqueous carrier, a lipid and a gas or gaseous precursor. The composition is flushed and the patient is scanned using diagnostic imaging to obtain a visible image of any diseased tissue in the region. The method involves flushing the lipid composition at a rate which substantially eliminates diagnostic artifacts in the image. A preferable flush rate is less than about 2.5 mL/sec.

Still another embodiment of the invention relates to a method for substantially eliminating diagnostic artifacts in a diagnostic image of an internal region of a patient. The method comprises regulating the rate at which a contrast agent is administered to a patient.

In another embodiment of the invention, there is provided a system for administering a contrast agent to a patient. The system comprises (a) a first vessel containing a contrast agent; (b) a second vessel containing a flush agent; (c) a conduit having means for directing fluid into a blood vessel of the patient; (d) means for placing said first and second vessels into flow communication with said conduit; (e) first flow inducing means for inducing said contrast agent to flow from said first vessel into said conduit; and (f) second flow inducing means for inducing said flush agent to flow from said second vessel into said conduit subsequent to said flowing of said contrast agent into said conduit by said first flow inducing means. In preferred form, the first flow inducing means comprises a syringe plunger and the first vessel comprises a syringe barrel in which the plunger slides. Also in preferred form, the second flow inducing means comprises a mechanical injector. The system is particularly suitable for use in the methods which are described herein for the administration of contrast agents.

These and other aspects of the invention will become more apparent from the present specification and claims.

BRIEF DESCRIPTION OF THE DRAWINGS

For the purpose of illustrating embodiments of the invention, there is shown in the drawings forms which are presently preferred. It should be understood, however, that this invention is not limited to the precise arrangements and instrumentalities shown.

DETAILED DESCRIPTION OF THE INVENTION

Figure 1:
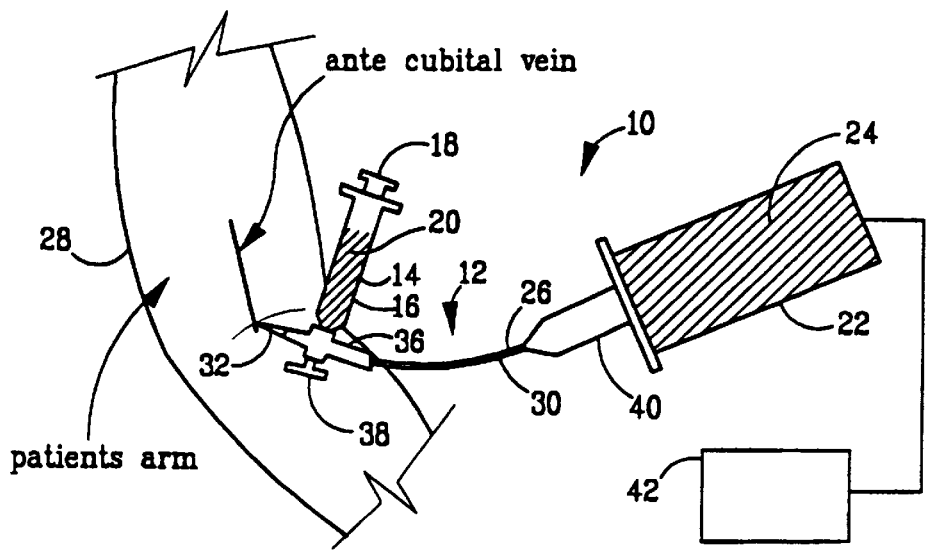
FIG. 1 is a schematic representation of a system including an apparatus for administering a contrast agent to a patient in accordance with an embodiment of the present invention.

As employed above and throughout the disclosure, the following terms, unless otherwise indicated, shall be understood to have the following meanings.

"Lipid" refers to a synthetic or naturally-occurring compound which is generally amphipathic and biocompatible. The lipids typically comprise a hydrophilic component and a hydrophobic component. Exemplary lipids include, for example, fatty acids, neutral fats, phosphatides, glycolipids, surface-active agents (surfactants), aliphatic alcohols, waxes, terpenes and steroids.

"Lipid composition" refers to a composition which comprises a lipid compound, typically in an aqueous medium. Exemplary lipid compositions include suspensions, emulsions and vesicle compositions.

"Lipid formulation" refers to a lipid composition which also comprises a bioactive agent.

"Vesicle" refers to a spherical entity which is generally characterized by the presence of one or more walls or membranes which form one or more internal voids. Vesicles may be formulated, for example, from lipids, including the various lipids described herein, proteinaceous materials, or polymeric materials, including natural, synthetic and semi-synthetic polymers. Preferred vesicles are those which comprise walls or membranes formulated from lipids. In these preferred vesicles, the lipids may be in the form of a monolayer or bilayer, and the mono- or bilayer lipids may be used to form one or more mono- or bilayers. In the case of more than one mono- or bilayer, the mono- or bilayers may be concentric. Lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). Similarly, the vesicles prepared from proteins or polymers may comprise one or more concentric walls or membranes. The walls or membranes of vesicles prepared from proteins or polymers may be substantially solid (uniform), or they may be porous or semi-pourous. The vesicles described herein include such entities commonly referred to as, for example, liposomes, micelles, bubbles, microbubbles, microspheres, lipid-, polymer- and/or protein-coated bubbles, microbubbles and/or microspheres, microballoons, aerogels, clathrate bound vesicles, and the like. The internal void of the vesicles may be filled with a liquid (including, for example, an aqueous liquid), a gas, a gaseous precursor, and/or a solid or solute material, including, for example, a targeting ligand and/or a bioactive agent, as desired.

"Liposome" refers to a generally spherical cluster or aggregate of amphipathic compounds, including lipid compounds, typically in the form of one or more concentric layers, for example, bilayers. They may also be referred to herein as lipid vesicles. The liposomes may be formulated, for example, from ionic lipids and/or non-ionic lipids. Liposomes which are formulated from non-ionic lipids may also be referred to as "niosomes."

"Micelle" refers to colloidal entities formulated from lipids. In certain preferred embodiments, the micelles comprise a monolayer or hexagonal H2 phase configuration. In other preferred embodiments, the micelles may comprise a bilayer configuration.

"Aerogel" refers to generally spherical entities which are characterized by a plurality of small internal voids. The aerogels may be formulated from synthetic materials (for example, a foam prepared from baking resorcinol and formaldehyde), as well as natural materials, such as polysaccharides or proteins.

"Clathrate" refers to a solid, semi-porous or porous particle which may be associated with vesicles. In preferred form, the clathrates may form a cage-like structure containing cavities which comprise the vesicles. One or more vesicles may be bound to the clathrate. A stabilizing material may, if desired, be associated with the clathrate to promote the association of the vesicle with the clathrate. Suitable materials from which clathrates may be formulated include, for example, porous apatites, such as calcium hydroxyapatite, and precipitates of polymers and metal ions, such as alginic acid precipitated with calcium salts.

The vesicles employed in the methods of the present invention preferably contain a gas or gaseous precursor. "Gas filled vesicle" refers to vesicles in which there is encapsulated a gas. "Gaseous precursor filled vesicle" refers to vesicles in which there is encapsulated a gaseous precursor. The vesicles may be minimally, partially or substantially completely filled with the gas and/or gaseous precursor. In certain preferred embodiments, the vesicles may be substantially or completely filled with the gas and/or gaseous precursor. The term "substantially", as used in reference to the gas and/or gaseous precursor filled vesicles, means that greater than about 50% of the internal void volume of the vesicle consists of a gas. Preferably, greater than about 60% of the internal void of the substantially filled vesicles consists of a gas, with greater than about 70% being more preferred. Even more preferably, greater than about 80% of the internal void of the substantially filled vesicles consists of a gas, with greater than about 90% being still more preferred. In particularly preferred embodiments, greater than about 95% of the internal void of the vesicles consists of a gas, with about 100% being especially preferred. Although not considered a preferred embodiment of the present invention, the vesicles may also contain, if desired, no or substantially no gas or gaseous precursor.

"Echogenic vesicle" refers to vesicles which may be capable of reflecting sound waves, including, for example, ultrasound waves. Echogenic vesicles may be particularly useful as contrast agents to alter, for example, the acoustic properties of an internal region of a patient, thereby resulting in improved contrast in diagnostic imaging techniques, such as ultrasound, computed tomography, and magnetic resonance imaging. In preferred form, the echogenic vesicles may comprise gas filled vesicles. Alternatively, the echogenic vesicles may comprise vesicles which contain no or substantially no gas or gaseous precursor and which, together with bubbles or globules of a gas or a gaseous precursor, are suspended in a liquid medium in divided form. In these latter embodiments, it is contemplated that echogenicity and/or an alteration in the acoustic properties of an internal region of a patient arises, at least in part, from the presence of the divided gas or gaseous precursor.

"Vesicle composition" refers to a composition, typically in an aqueous medium, which comprises vesicles.

"Vesicle formulation" refers to a vesicle composition which also comprises a bioactive agent. Suitable vesicles or vesicle species for use in vesicle formulations include, for example, gas filled vesicles and gaseous precursor filled vesicles.

"Emulsion" refers to a lipoidal mixture of two or more liquids and is generally in the form of a colloid. The lipids may be heterogeneously dispersed throughout the emulsion. Alternatively, the lipids may be aggregated in the form of, for example, clusters or layers, including mono- or bilayers.

"Suspension" refers to a mixture of finely divided liquid or solid particles floating in a liquid which can remain stable for extended periods of time.

"Hexagonal H II phase structure" refers to a generally tubular aggregation of lipids in liquid media, for example, aqueous media, in which the hydrophilic portion(s) of the lipids generally face inwardly in association with a liquid environment inside the tube. The hydrophobic portion(s) of the lipids generally radiate outwardly and the complex assumes the shape of a hexagonal tube. A plurality of tubes is generally packed together in the hexagonal phase structure.

"Patient" refers to animals, including mammals, preferably humans.

The phrases "internal region of a patient" and "region of interest" refer to the entire patient or to a particular area or portion of the patient. Internal regions of a patient and regions of interest may include, for example, areas being imaged with diagnostic imaging and/or areas being treated with a bioactive agent. Exemplary of such areas include, for example, the heart region, including myocardial tissue, as well as other bodily tissues, including the vasculature and circulatory system and cancerous tissue. The phrase "vasculature," as used herein, denotes the blood vessels in the body or in an organ or part of the body.

"Bioactive agent" refers to a substance which may be used in connection with an application that is therapeutic or diagnostic in nature, such as in methods for diagnosing the presence or absence of a disease in a patient and/or in methods for the treatment of disease in a patient. As used herein, "bioactive agent" refers also to substances which are capable of exerting a biological effect in vitro and/or in vivo. The bioactive agents may be neutral or positively or negatively charged. Examples of suitable bioactive agents include diagnostic agents, pharmaceuticals, drugs, synthetic organic molecules, proteins, peptides, vitamins, steroids, steroid analogs, and genetic material, including nucleosides, nucleotides and polynucleotides.

"Diagnostic agent" refers to any agent which may be used in connection with methods for imaging an internal region of a patient and/or diagnosing the presence or absence of a disease in a patient. Exemplary diagnostic agents include, for example, contrast agents for use in connection with ultrasound, magnetic resonance imaging or computed tomography of a patient including, for example, the lipid and/or vesicle compositions described herein.

"Polymer", as used herein, refers to molecules formed from the chemical union of two or more repeating units. Accordingly, included within the term "polymer" may be, for example, dimers, trimers and oligomers. The polymer may be synthetic, naturally-occurring or semisynthetic. In preferred form, the term "polymer" refers to molecules which comprise 10 or more repeating units.

"Thickening agent" refers to any of a variety of generally hydrophilic materials which, when incorporated in the lipid and/or vesicle compositions described herein, may act as viscosity modifying agents, emulsifying and/or solubilizing agents, suspending agents, and tonicity raising agents. It is contemplated that the thickening agents may be capable of aiding in maintaining the stability of the compositions due to such properties.

"Dispersing agent" refers to a surface-active agent which, when added to a suspending medium of colloidal particles, including, for example, certain of the lipid and/or vesicle compositions described herein, may promote uniform separation of particles. In certain preferred embodiments, the dispersing agent may comprise a polymeric siloxane compound.

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination of the two. The DNA and RNA may optionally comprise unnatural nucleotides and may be single or double stranded. "Genetic material" refers also to sense and anti-sense DNA and RNA, that is, a nucleotide sequence which is complementary to a specific sequence of nucleotides in DNA and/or RNA.

"Pharmaceutical" or "drug" refers to any therapeutic or prophylactic agent which may be used in the treatment (including the prevention, diagnosis, alleviation, or cure) of a malady, affliction, disease or injury in a patient. Therapeutically useful peptides, polypeptides and polynucleotides may be included within the meaning of the term pharmaceutical or drug.

"Diagnostic artifact" refers generally to imperfections, defects and/or flaws in a diagnostic image including, for example, ultrasound, computed tomography and magnetic resonance images, which may hamper and/or prevent visualization of a region of interest. Diagnostic artifacts may be associated with excess and/or insufficient concentrations of contrast agent. In the case of excess concentrations, diagnostic artifacts may be manifested as undesired darkening and/or shadowing. It is contemplated that the excess concentration of contrast agent may form, for example, an obstruction or barrier, which may prevent penetration, for example, of sound waves in the case of ultrasound, through the contrast agent and into tissues and/or structures in the patient which are proximate the contrast agent and/or the region being imaged. In the case of insufficient concentrations, diagnostic artifacts may be manifested as undesired lightening and/or brightening.

"Ultrasound artifact" and "computed tomography artifact" refer respectively to diagnostic artifacts associated with ultrasound and computed tomography.

"Substantial elimination" refers to the prevention or substantial prevention of the occurrence of diagnostic artifacts in a diagnostic image. The term "substantial prevention" means that at least about 50% of the artifacts may be eliminated by the methods of the present invention as compared to at least one prior art diagnostic method. Preferably, at least about 60% of the artifacts may be eliminated by the methods of the present invention as compared to at least one prior art diagnostic method, with the elimination of at least about 70% of the artifacts being more preferred. Even more preferably, at least about 80% of the artifacts may be eliminated by the methods of the present invention as compared to at least one prior art diagnostic method, with the elimination of at least about 90% of the artifacts being still more preferred. Yet more preferably, at least about 95% of the artifacts may be eliminated by the methods of the present invention as compared to at least one prior art diagnostic method, with the elimination of at least about 100% being still more preferred.

The terms "administered" and "administration" refer generally to the administration to a patient of a biocompatible material, including, for example, lipid and/or vesicle compositions and flush agents. Accordingly, "administered" and "administration" refer, for example, to the injection into a blood vessel of lipid and/or vesicle compositions and/or flush agents. The terms "administered" and "administration" can also refer to the delivery of lipid and/or vesicle compositions and/or flush agents to a region of interest.

"Flushing" refers to the administration to a patient of a flush agent after the administration of a lipid and/or vesicle composition. The term "flush agent" refers to biocompatible materials which may be capable, upon administration, of facilitating the movement of a lipid and/or vesicle composition through the circulatory system. An exemplary flush agent is saline solution. In embodiments which involve the administration of a lipid and/or vesicle composition intravenously (IV), the flush is preferably also administered IV, typically at or near the location that the lipid and/or vesicle composition is administered.

"Biocompatible" refers to materials which are generally not injurious to biological functions and which will not result in any degree of unacceptable toxicity, including allergenic responses and disease states.

"In combination with" refers to the co-administration of a bioactive agent with a lipid and/or vesicle composition. The term "co-administration" means that the bioactive agent may be administered before, during, or after the administration of the lipid and/or vesicle composition. The lipid and/or vesicle composition may be combined with the bioactive agent in any of a variety of different ways. For example, in the case of vesicle compositions, the bioactive agent may be entrapped within the internal void of the vesicle. In addition, the bioactive agent may be integrated within the layer(s) or wall(s) of the vesicle, for example, by being interspersed among lipids (in the case of vesicle compositions which comprise vesicles formulated from lipids) which are contained within the vesicle layer(s) or wall(s). It is contemplated that the bioactive agent may be located on the surface of a vesicle. In this case, the bioactive agent may interact chemically with the surface of the vesicle and remain substantially adhered thereto. Such interaction may take the form of, for example, electrostatic interactions, hydrogen bonding, van der Waal's forces or covalent bonding. Also, the bioactive agent may interact with the surface of the vesicle in a limited manner. Such limited interaction would permit migration of the bioactive agent, for example, from the surface of a first vesicle to the surface of a second vesicle.

The present invention is directed, in part, to improved methods for diagnostic imaging, including, for example, improved methods for providing an image of an internal region of a patient. Embodiments of the present invention involve the administration to the patient of a contrast agent in the form of a lipid composition comprising, in an aqueous carrier, a lipid and a gas or gaseous precursor. Embodiments of the present invention also involve the administration to the patient of a contrast agent in the form of a vesicle composition comprising, in an aqueous carrier, vesicles and a gas or gaseous precursor. The patient is scanned using ultrasound to obtain a visible image of the region. An important feature of the methods of the present invention is that the contrast agent (lipid and/or vesicle composition) is administered to the patient at a rate which substantially eliminates ultrasound artifacts in the image.

The improved methods of the present invention provide highly desirable advantages relative to methods for diagnostic imaging, especially ultrasound, which have been available heretofore. In this connection, a surprising and unexpected advantage of the present invention is that methods are provided which may enable the substantial elimination from diagnostic images, including ultrasound and computed tomography images, of diagnostic artifacts. As known to the skilled artisan, diagnostic artifacts may occur frequently in diagnostic images which are obtained using methods for diagnostic imaging that are currently available. Diagnostic artifacts may be highly undesirable since they may hamper or even prevent visualization of a region of interest. Thus, in certain circumstances, diagnostic artifacts may render a diagnostic image substantially unusable.

As noted above, diagnostic artifacts may be caused by an excess and/or insufficient concentration of contrast agent at a region of interest. It has been found unexpectedly that the rate at which a contrast agent is administered to a patient may have a profound effect on the quality of the resulting diagnostic image. For example, diagnostic imaging of tissue, such as myocardial tissue, may involve the use of a contrast agent, for example, a contrast agent comprising vesicles, which is administered intravenously. After injection, the contrast agent may be carried in the bloodstream to the desired tissue. Energy, for example, ultrasound, may be applied, and a diagnostic image may be generated. The inventors have found that a rapid injection of contrast agent may result in the undesirable introduction into the bloodstream of a concentrated mass of contrast agent. As this concentrated mass reaches the region of interest, for example, the heart region, visualization may be hampered and/or prevented due to diagnostic artifacts caused, for example, by the partial or complete obstruction of the region by the contrast agent. Conversely, it has been found that a slow or prolonged injection may result in the undesirable dilution of the contrast agent in the bloodstream. This may provide an insufficient concentration of contrast agent at the region of interest. Visualization may therefore be hampered and/or precluded due to insufficient contrast. The present invention is directed, at least in part, to methods which provide a simple and effective means for the control and/or regulation of the concentration of contrast agent at a region of interest.

In accordance with the present invention, there are provided methods which involve, inter alia, the administration to a patient of a contrast agent, preferably in the form of lipid and/or vesicle composition. In connection with lipid compositions, and especially lipid compositions in the form of vesicle compositions, it may be advantageous to prepare the lipid compositions at a temperature below the gel to liquid crystalline phase transition temperature of the involved lipids. This phase transition temperature is the temperature at which a lipid bilayer will convert from a gel state to a liquid crystalline state. See, for example, Chapman et al., *J. Biol. Chem.* 1974 249, 2512–2521.

It is generally believed that vesicles which are prepared from lipids that possess higher gel state to liquid crystalline state phase transition temperatures tend to have enhanced impermeability at any given temperature. See Derek Marsh, *CRC Handbook of Lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984). The following table lists some of the representative lipids and their phase transition temperatures.

TABLE 1

Saturated Diacyl-sn-Glycero-3-Phosphocholines:
Main Chain Melting Transition Temperatures

| Number of Carbons in Acyl Chains | Main Phase Transition Temperature (° C.) |
|---|---|
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

See, for example, Derek Marsh, CRC Handbook of Lipid Bilayers, p. 139 (CRC Press, Boca Raton, FL 1990).

It may be possible to enhance the stability of vesicles formulated from lipids by incorporating in the lipid compositions at least a minor amount, for example, about 1 to about 10 mole percent, based on the total amount of lipid employed, of a negatively charged lipid. Suitable negatively charged lipids include, for example, phosphatidylserine, phosphatidic acid, and fatty acids. Without intending to be bound by any theory or theories of operation, it is contemplated that such negatively charged lipids may provide added stability by counteracting the tendency of vesicles to rupture by fusing together. Thus, the negatively charged lipids may act to establish a uniform negatively charged layer on the outer surface of the vesicle, which will be repulsed by a similarly charged outer layer on other vesicles which may be proximate thereto. In this way, the vesicles may be less prone to come into touching proximity with each other, which may lead to a rupture of the membrane or skin of the respective vesicles and consolidation of the contacting vesicles into a single, larger vesicle. A continuation of this process of consolidation will, of course, lead to significant degradation of the vesicles.

The lipid materials used in certain of the compositions described herein, especially in connection with vesicle compositions based on lipids, are also preferably flexible. This means that, for example, in the case of vesicle compositions based on lipids, the vesicles can alter their shape, for example, to pass through an opening having a diameter that is smaller than the diameter of the vesicle.

A wide variety of lipids are believed to be suitable for incorporation in the lipid and/or vesicle compositions. With particular reference to vesicle compositions, for example, micelles and/or liposomes, any of the materials or combinations thereof which are known to those skilled in the art as suitable for their preparation may be used. The lipids used may be of natural, synthetic or semi-synthetic origin. As noted above, suitable lipids generally include, for example, fatty acids, neutral fats, phosphatides, glycolipids, aliphatic alcohols and waxes, terpenes and steroids.

Exemplary lipids which may be used to prepare lipid compositions include, for example, fatty acids; lysolipids; phosphocholines; phosphatidylcholine with both saturated and unsaturated lipids, including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipalmitoylphosphatidylethanolamine (DPPE) and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing biocompatible polymers, such as chitin, hyaluronic acid, polyvinylpyrrolidone or polyethylene glycol (PEG), the latter being also referred to herein as "pegylated lipids", with preferred lipids bearing polymers including DPPE-PEG, which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers and polyoxyethylene fatty acid stearates; sterol aliphatic acid esters, including cholesterol sulfate, cholesterol butyrate, cholesterol iso-butyrate, cholesterol palmitate, cholesterol stearate, lanosterol acetate, ergosterol palmitate and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate and ergosterol gluconate; esters of sugar acids and alcohols including lauryl glucuronide, stearoyl glucuronide, myristoyl glucuronide, lauryl gluconate, myristoyl gluconate and stearoyl gluconate; esters of sugars and aliphatic acids, including sucrose laurate, fructose laurate, sucrose palmitate, sucrose stearate, glucuronic acid, gluconic acid and polyuronic acid; saponins, including sarsasapogenin, smilagenin, hederagenin, oleanolic acid and digitoxigenin; glycerols, including glycerol dilaurate, glycerol trilaurate, glycerol dipalmitate, glycerol and glycerol esters, such as glycerol tripalmitate, glycerol distearate, glycerol tristearate, glycerol dimyristate and glycerol trimyristate; long chain alcohols, including n-decyl alcohol, lauryl alcohol, myristyl alcohol, cetyl alcohol and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-

(((7'-diethylaminocoumarin-3-yl)carbonyl)methylamino)-octadecanoic acid; N-[12-(((7'-diethylaminocoumarin-3-yl)carbonyl)methylamino)-octadecanoyl]-2-aminopalmitic acid; cholesteryl)4'-trimethylammonio)butanoate; N-succinyldioleoylphosphatidylethanol-amine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or combinations thereof.

If desired, a cationic lipid may be used, such as, for example, N-[1-(2,3-dioleoyloxy)propyl]-N,N,N-trimethylammonium chloride (DOTMA), 1,2-dioleoyloxy-3-(trimethylammonio)propane (DOTAP); and 1,2-dioleoyl-3-(4'-trimethylammonio)-butanoyl-sn-glycerol (DOTB). If a cationic lipid is employed in the lipid compositions, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1.

In the case of lipid compositions which contain both cationic and non-cationic lipids, a wide variety of lipids may be employed as the non-cationic lipid. Preferably, this non-cationic lipid comprises one or more of DPPC, DPPE and dioleoylphosphatidylethanolamine. In lieu of the cationic lipids listed above, lipids bearing cationic polymers, such as polylysine or polyarginine, as well as alkyl phosphonates, alkyl phosphinates and alkyl phosphites, may also be used in the lipid compositions.

In preferred embodiments, the lipid compositions comprise phospholipids, particularly one or more of DPPC, DPPE, DPPA, DSPC, DSPE, and DAPC (20 carbons), with DPPC being especially preferred.

Saturated and unsaturated fatty acids may also be employed in the lipid compositions described herein and may include molecules that preferably contain from about 12 carbons to about 22 carbons, in linear or branched form. Hydrocarbon groups consisting of isoprenoid units and/or prenyl groups can be used as well. Examples of saturated fatty acids that are suitable include, for example, lauric, myristic, palmitic and stearic acids. Suitable unsaturated fatty acids that may be used include, for example, lauroleic, physeteric, myristoleic, linoleic, linolenic, palmitoleic, petroselinic and oleic acids. Examples of branched fatty acids that may be used include, for example, isolauric, isomyristic, isopalmitic and isostearic acids.

In addition to lipid compositions and/or vesicle compositions formulated from lipids, the methods of the present invention may also involve vesicles formulated from proteins or derivatives thereof. Vesicles which are formulated from proteins and which would be suitable for use in the methods of the present invention are described, for example, in Feinstein, U.S. Pat. Nos. 4,572,203, 4,718,433 and 4,774,958, and Cerny et al., U.S. Pat. No. 4,957,656. Other protein-based vesicles, in addition to those described in the aforementioned patents, would be apparent to one of ordinary skill in the art, once armed with the present disclosure.

In addition to lipid compositions and/or vesicle compositions formulated from lipids and/or proteins, the methods of the present invention may also involve vesicles formulated from polymers which may be of natural, semi-synthetic (modified natural) or synthetic origin. As used herein, the term polymer denotes a compound comprised of two or more repeating monomeric units, and preferably 10 or more repeating monomeric units. The phrase semi-synthetic polymer (or modified natural polymer), as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, polydextrose, pustulan, chitin, agarose, keratan, chondroitan, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinylchloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof. Preferred are biocompatible synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, ε-caprolactone, acrolein, cyanoacrylate, bisphenol A, epichlorhydrin, hydroxyalkyl-acrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethylmethacrylate, vinyl pyridine, aminoethyl methacrylates, 2-methacryloyloxy-trimethylammonium chloride, and polyvinylidene, as well polyfunctional crosslinking monomers such as N,N'-methylenebisacrylamide, ethylene glycol dimethacrylates, 2,2'-(p-phenylenedioxy)-diethyl dimethacrylate, divinylbenzene, triallylamine and methylenebis-(4-phenyl-isocyanate), including combinations thereof Preferable polymers include polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly(ethylene glycol), and polyamide (nylon) polymers. Preferable copolymers include the following: polyvinylidene-polyacrylonitrile, polyvinylidene-polyacrylonitrile-polymethylmethacrylate, polystyrene-polyacrylonitrile and poly d-1, lactide co-glycolide polymers. A preferred copolymer is polyvinylidene-polyacrylonitrile. Other suitable biocompatible monomers and polymers will be readily apparent to those skilled in the art, once armed with the present disclosure.

Vesicle derived from polymers for use in the methods of the present invention are preferably low density. The term "low density" refers to vesicles which have an internal void (cavity) volume which is at least about 75% of the total volume of the vesicle. Preferably, the vesicles have a void volume of at least about 80%, more preferably at least about 85%, even more preferably at least about 90%, still more preferably at least about 95%, and yet more preferably about 100% of the total volume of the vesicles.

As noted above, the lipid and/or vesicle compositions employed in the present methods may also comprise a gas, such as an inert gas. The gas provides the lipid and/or vesicle compositions with enhanced reflectivity, particularly in connection with vesicle compositions in which the gas is entrapped within the vesicles. This may increase the effectiveness of the vesicle compositions as contrast agents.

Preferred gases are gases which are inert and which are biocompatible, that is, gases which are not injurious to biological function. Preferred gases include those selected from the group consisting of air, noble gases, such as helium, rubidium hyperpolarized xenon, hyperpolarized argon, hyperpolarized helium, neon, argon, xenon, carbon dioxide, nitrogen, fluorine, oxygen, sulfur-based gases, such as sulfur hexafluoride and sulfur tetrafluoride, fluorinated gases, including, for example, partially fluorinated gases or completely fluorinated gases. Exemplary fluorinated gases include the fluorocarbon gases, such as the perfluorocarbon gases, and mixtures thereof. Paramagnetic gases, such as $^{17}O_2$, may also be used in the lipid and/or vesicle compositions.

In preferred embodiments, the gas utilized in the compositions described herein comprises a fluorinated gas. Such fluorinated gases include materials which contain at least one, or more than one, fluorine atom. Preferred are gases which contain more than one fluorine atom, with perfluorocarbons (that is, fully fluorinated fluorocarbons) being more preferred. Preferably, the perfluorocarbon gas is selected from the group consisting of perfluoromethane, perfluoroethane, perfluoropropane, perfluorobutane, perfluoropentane, perfluorocyclobutane and mixtures thereof. More preferably, the perfluorocarbon gas is perfluoropropane or perfluorobutane, with perfluoropropane being particularly preferred. Another preferable gas is sulfur hexafluoride. Yet another preferable gas is heptafluoropropane, including 1,1,1,2,3,3,3-heptafluoropropane and its isomer, 1,1,2,2,3,3,3-heptafluoropropane. It is contemplated that mixtures of different types of gases, such as mixtures of a perfluorocarbon gas and another type of gas, such as air, can also be used in the compositions employed in the methods of the present invention. Other gases, including the gases exemplified above, would be readily apparent to one skilled in the art based on the present disclosure.

In certain preferred embodiments, a gas, for example, air or a perfluorocarbon gas, is combined with a liquid perfluorocarbon, such as perfluoropentane, perfluorohexane, perfluoroheptane, perfluorooctylbromide (PFOB), perfluorodecalin, perfluorododecalin, perfluorooctyliodide, perfluorotripropylamine and perfluorotributylamine.

It may also be desirable to incorporate in the lipid and/or vesicle compositions a precursor to a gaseous substance. Such precursors include materials that are capable of being converted to a gas in vivo. Preferably, the gaseous precursor is biocompatible, and the gas produced in vivo is biocompatible also.

Among the gaseous precursors which are suitable for use in the lipid and/or vesicle compositions described herein are agents which are sensitive to pH. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof. Carbonic acid ($H_2CO_3$) is an example of a suitable inorganic acid, and aminomalonic acid is an example of a suitable organic acid. Other acids, including inorganic and organic acids, would be readily apparent to one skilled in the art based on the present disclosure.

Gaseous precursors which are derived form salts are preferably selected from the group consisting of alkali metal salts, ammonium salts and mixtures thereof. More preferably, the salt is selected from the group consisting of carbonate, bicarbonate, sesquecarbonate, aminomalonate and mixtures thereof.

Examples of suitable gaseous precursor materials which are derived from salts include, for example, lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, Vol. 9, no. 3, pp. 525–532 (1970); Fitzpatrick et al., *Inorganic Chemistry*, Vol. 13, no. 3 pp. 568–574 (1974); and Stelmashok et al., *Koordinatsionnaya Khimiya*, Vol. 3, no. 4, pp. 524–527 (1977). The disclosures of these publications are hereby incorporated herein by reference, in their entirety.

In addition to, or instead of being sensitive to changes in pH, the gaseous precursor materials may also comprise compounds which are sensitive to changes in temperature. Exemplary of suitable gaseous precursors which are sensitive to changes in temperature are the perfluorocarbons. As the artisan will appreciate, a particular perfluorocarbon may exist in the liquid state when the lipid and/or vesicle compositions are first made, and thus may be used as a gaseous precursor. Alternatively, the perfluorocarbon may exist in the gaseous state when the lipid and/or vesicle compositions are made, and thus may be used directly as a gas. Whether the perfluorocarbon is used as a liquid or a gas generally depends on its liquid/gas phase transition temperature, or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., this temperature being above the transition temperature of perfluoropentane. Thus, under normal circumstances, perfluoropentane is a gaseous precursor. As a further example, there are the homologs of perfluoropentane, namely perfluorobutane and perfluorohexane. The liquid/gas transition of perfluorobutane is 4° C. and that of perfluorohexane is 57° C. Thus, perfluorobutane may be useful as a gaseous precursor, although more likely as a gas, whereas perfluorohexane may be useful as a gaseous precursor because of its relatively high boiling point. As known to one of ordinary skill in the art, the effective boiling point of a substance may be related to the pressure to which that substance is exposed. This relationship is exemplified by the ideal gas law PV=nRT, where P is pressure, V is volume, n is moles of substance, R is the gas constant, and T is temperature. The ideal gas law indicates that as pressure increases, the effective boiling point increases also. Conversely, as pressure decreases, the effective boiling point decreases.

A wide variety of materials may be used as temperature-sensitive gaseous precursors in the compositions described herein. It is only required that the material be capable of undergoing a phase transition to the gas phase upon passing through the appropriate temperature. Suitable gaseous precursors include, for example, hexafluoroacetone, isopropyl acetylene, allene, tetrafluoroallene, boron trifluoride, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiyne, 1-fluorobutane, 2-methylbutane, perfluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, perfluoro-2-butyne, 2-bromobutyraldehyde, carbonyl sulfide, crotononitrile, cyclobutane, methylcyclobutane, octafluorocyclobutane, perfluorocyclobutene, 3-chlorocyclopentene, perfluorocyclopentane, octafluorocyclopentene, cyclopropane, perfluorocyclopropane, 1,2-dimethyl-cyclopropane, 1,1-dimethylcyclopropane, 1,2-dimethylcyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis(dimethylphosphine)amine, perfluorohexane, perfluoroheptane, perfluorooctane, 2,3-dimethyl-2-norbornane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, perfluoroethane, nitropentafluoroethane, nitrosopentafluoroethane, perfluoroethylamine, ethyl vinyl ether, 1,1-dichloroethane, 1,1-dichloro-1,2-difluoroethane, 1,2-difluoroethane, methane, trifluoromethanesulfonyl chloride, trifluoromethanesulfonylfluoride, bromodifluoro-nitrosomethane, bromofluoromethane, bromo-chlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neopentane, nitrous oxide, 1,2,3-nonadecanetricarboxylic acid 2-hydroxytrimethyl ester, 1-nonene-3-yne, 1,4-pentadiene, n-pentane, perfluoropentane, 4-amino-4-methylpentan-2-one, 1-pentene, 2-pentene (cis and trans), 3-bromopent-1-ene, perfluoropent-1-ene, tetrachlorophthalic acid, 2,3,6-trimethylpiperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3-dichloropropane, 1-chloropropane, chloropropane-(trans), 2-chloropropane, 3-fluoropropane, propyne, 3,3,3-trifluoropropyne, 3-fluorostyrene, sulfur (di)-decafluoride ($S_2F_{10}$), 2,4-diaminotoluene, trifluoroacetonitrile, trifluoromethyl peroxide, trifluoromethyl sulfide, tungsten hexafluoride, vinyl acetylene and vinyl ether.

Perfluorocarbons are both preferred gases and preferred gaseous precursors for use in connection with the compositions employed in the methods of the present invention. Included among such perfluorocarbons are saturated perfluorocarbons, unsaturated perfluorocarbons, and cyclic perfluorocarbons. The saturated perfluorocarbons, which are usually preferred, have the formula $C_nF_{2n+2}$, where n is from 1 to about 12, preferably about 2 to about 10, more preferably about 3 to about 8, and even more preferably about 3 to about 6. Suitable perfluorocarbons include, for example, perfluoromethane, perfluoroethane, perfluoropropane, perfluorobutane, perfluorocyclobutane, perfluoropentane, perfluorohexane, perfluoroheptane, perfluorooctane and perfluorononane. Preferably, the perfluorocarbon is selected from the group consisting of perfluoropropane, perfluorobutane, perfluorocyclobutane, perfluoropentane, perfluorohexane and perfluorooctane, with perfluoropropane being particularly preferred. Cyclic perfluorocarbons, which have the formula $C_nF_{2n}$, where n is from 3 to 8, preferably 3 to 6, may also be preferred, and include, for example, hexafluorocyclopropane, octafluorocyclobutane, and decafluorocyclopentane.

In addition to the perfluorocarbons, it may be desirable to utilize stable fluorocarbons which are not completely fluorinated. Such fluorocarbons include heptafluoropropane, for example, 1,1,1,2,3,3,3-heptafluoropropane and its isomer, 1,1,2,2,3,3,3-heptafluoropropane.

The gaseous precursor materials may be also photoactivated materials, such as diazonium ion and aminomalonate. Certain lipid and/or vesicle compositions, and particularly vesicle compositions, may be formulated so that gas can be formed at the target tissue or by the action of sound on the composition. Examples of gaseous precursors are described, for example, in U.S. Pat. Nos. 5,088,499 and 5,149,319, the disclosures of which are hereby incorporated herein by reference, in their entirety. Other gaseous precursors, in addition to those exemplified above, will be apparent to one skilled in the art based on the present disclosure.

The gaseous substances and/or gaseous precursors are preferably incorporated in the lipid and/or vesicle compositions irrespective of the physical nature of the composition. Thus, it is contemplated that the gaseous substances and/or precursors thereto may be incorporated, for example, in lipid compositions in which the lipids are aggregated randomly, as well as in vesicle compositions, including vesicle compositions which are formulated from lipids, such as micelles and liposomes. Incorporation of the gaseous substances and/or precursors thereto in the lipid and/or vesicle compositions may be achieved by using any of a number of methods. For example, in the case of vesicles based on lipids, the formation of gas filled vesicles can be achieved by shaking or otherwise agitating an aqueous mixture which comprises a gas or gaseous precursor and one or more lipids. This promotes the formation of stabilized vesicles within which the gas or gas precursor is encapsulated.

In addition, a gas may be bubbled directly into an aqueous mixture of lipid and/or vesicle-forming compounds. Alternatively, a gas instillation method can be used as disclosed, for example, in U.S. Pat. Nos. 5,352,435 and 5,228,446, the disclosures of which are hereby incorporated herein by reference, in their entirety. Suitable methods for incorporating the gas or gas precursor in cationic lipid compositions are disclosed also in U.S. Pat. No. 4,865,836, the disclosures of which are hereby incorporated herein by reference. Other methods would be apparent to one skilled in the art based on the present disclosure. Preferably, the gas may be instilled in the lipid and/or vesicle compositions after or during the addition of the stabilizing material and/or during formation of vesicles.

In preferred embodiments, the gaseous substances and/or gaseous precursor materials are incorporated in vesicle compositions, with micelles and liposomes being preferred. As discussed in detail below, vesicles in which a gas or gaseous precursor or both are encapsulated are advantageous in that they provide improved reflectivity in vivo.

As discussed more fully hereinafter, it is preferred that the lipid compositions, and especially the vesicle compositions, be formulated from lipids and optional stabilizing compounds to promote the formation of stable vesicles. In addition, it is also preferred that the lipid and/or vesicle compositions comprise a highly stable gas as well. The phrase "highly stable gas" refers to a gas which has limited solubility and diffusability in aqueous media. Exemplary highly stable gases include perfluorocarbons since they are generally less diffusible and relatively insoluble in aqueous media. Accordingly, their use may promote the formation of highly stable vesicles.

In certain embodiments, it may be desirable to use a fluorinated compound, especially a perfluorocarbon compound, which may be in the liquid state at the temperature of use of the lipid and/or vesicle compositions, including, for example, the in vivo temperature of the human body, to assist or enhance the stability of the lipid and/or vesicle compositions, and especially, the gas filled vesicles. Suitable fluorinated compounds include, for example, fluorinated surfactants, such as fluorinated surfactants which are commercially available as ZONYL® surfactants (the DuPont Company, Wilmington, Del.), as well as liquid perfluorocarbons, such as for example, perfluorooctylbromide (PFOB), perfluorodecalin, perfluorododecalin, perfluorooctyliodide, perfluorotripropylamine, and perfluorotributylamine. In general, perfluorocarbons comprising about six or more carbon atoms will be liquids at normal human body temperature. Among these perfluorocarbons, perfluorooctylbromide and perfluorohexane, which are liquids at room temperature, are preferred. The gas which is present may be, for example, nitrogen or perfluoropropane, or may be derived from a gaseous precursor, which may also be a perfluorocarbon, for example, perfluoropentane. In the latter case, the lipid and/or vesicle compositions may be prepared from a mixture of perfluorocarbons, which for the examples given, would be perfluoropropane (gas) or perfluoropentane (gaseous precursor) and perfluorooctylbromide (liquid). Although not intending to be bound by any theory or theories of operation, it is believed that, in the case of vesicle compositions, the liquid fluorinated compound may be situated at the interface between the gas and the membrane or wall surface of the vesicle. There may be thus formed a further stabilizing layer of liquid fluorinated compound on the internal surface of the stabilizing compound, for example, a biocompatible lipid used to form the vesicle, and this perfluorocarbon layer may also prevent the gas from diffusing through the vesicle membrane. A gaseous precursor, within the context of the present invention, is a liquid at the temperature of manufacture and/or storage, but becomes a gas at least at or during the time of use.

Thus, it has been discovered that a liquid fluorinated compound, such as a perfluorocarbon, when combined with a gas or gaseous precursor ordinarily used to make the lipid and/or vesicle compositions described herein, may confer an added degree of stability not otherwise obtainable with the gas or gaseous precursor alone. Thus, it is within the scope of the present invention to utilize a gas or gaseous precursor, such as a perfluorocarbon gaseous precursor, for example, perfluoropentane, together with a perfluorocarbon which remains liquid after administration to a patient, that is, whose liquid to gas phase transition temperature is above the body temperature of the patient, for example, perfluorooctylbromide. Perfluorinated surfactants, such as ZONYL® fluorinated surfactants, may be used to stabilize the lipid and/or vesicle compositions, and to act, for example, as a coating for vesicles. Preferred perfluorinated surfactants are the partially fluorinated phosphocholine surfactants. In these preferred fluorinated surfactants, the dual alkyl compounds may be fluorinated at the terminal alkyl chains and the proximal carbons may be hydrogenated. These fluorinated phosphocholine surfactants may be used for making the targeted lipid and/or vesicle compositions employed in the methods of the present invention.

In connection with embodiments involving vesicle compositions, the size of the vesicles can be adjusted for the particular intended end use including, for example, diagnostic and/or therapeutic use. The size of the vesicles may preferably range from about 30 nanometers (nm) to about 100 micrometers ($\mu$m) in diameter, and all combinations and subcombinations of ranges therein. More preferably, the vesicles have diameters of from about 100 nm to about 10 $\mu$m, with diameters of from about 200 nm to about 7 $\mu$m being even more preferred. In connection with particular uses, for example, intravascular use, including magnetic resonance imaging of the vasculature, it may be preferred that the vesicles be no larger that about 30 $\mu$m in diameter, with smaller vesicles being preferred, for example, vesicles of no larger than about 12 $\mu$m in diameter. In certain preferred embodiments, the diameter of the vesicles may be about 7 $\mu$m or less, with vesicles having a mean diameter of about 5 $\mu$m or less being more preferred, and vesicles having a mean diameter of about 3 $\mu$m or less being even more preferred. It is contemplated that these smaller vesicles may perfuse small vascular channels, such as the microvasculature, while at the same time providing enough space or room within the vascular channel to permit red blood cells to slide past the vesicles.

The size of the gas filled vesicles can be adjusted, if desired, by a variety of procedures including, for example, shaking, microemulsification, vortexing, extrusion, filtration, sonication, homogenization, repeated freezing and thawing cycles, extrusion under pressure through pores of defined size, and similar methods.

As noted above, compositions employed herein may also include, with respect to their preparation, formation and use, gaseous precursors that can be activated to change from a liquid or solid state into a gas by temperature, pH, light, and energy (such as ultrasound). The gaseous precursors may be made into gas by storing the precursors at reduced pressure. For example, a vial stored under reduced pressure may create a headspace of perfluoropentane or perfluorohexane gas, useful for creating a preformed gas prior to injection. Preferably, the gaseous precursors may be activated by temperature. Set forth below is a table listing a series of gaseous precursors which undergo phase transitions from liquid to gaseous states at relatively close to normal body temperature (37° C.) or below, and the size of the emulsified droplets that would be required to form a vesicle of a maximum size of 10 μm.

TABLE 2

Physical Characteristics of Gaseous Precursors and Diameter of Emulsified Droplet to Form a 10 μm Vesicle*

| Compound | Molecular Weight | Boiling Point (° C.) | Density | Diameter (μm) of emulsified droplet to make 10 micron vesicle |
|---|---|---|---|---|
| perfluoro pentane | 288.04 | 28.5 | 1.7326 | 2.9 |
| 1-fluorobutane | 76.11 | 32.5 | 0.67789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluoro cyclobutane | 200.04 | -5.8 | 1.48 | 2.8 |
| decafluoro butane | 238.04 | -2 | 1.517 | 3.0 |
| hexafluoro ethane | 138.01 | -78.1 | 1.607 | 2.7 |

*Source: Chemical Rubber Company Handbook of Chemistry and Physics, Robert C. Weast and David R. Lide, eds., CRC Press, Inc. Boca Raton, Florida (1989-1990).

The perfluorocarbons, as already indicated, are preferred for use as the gas or gaseous precursors, as well as additional stabilizing components.

As noted above, it is preferred to optimize the utility of the lipid and/or vesicle compositions, especially vesicle compositions formulated from lipids, by using gases of limited solubility. The phrase "limited solubility" refers to the ability of the gas to diffuse out of the vesicles by virtue of its solubility in the surrounding aqueous medium. A greater solubility in the aqueous medium imposes a gradient with the gas in the vesicle such that the gas may have a tendency to diffuse out of the vesicle. A lesser solubility in the aqueous milieu, may, on the other hand, decrease or eliminate the gradient between the vesicle and the interface such that diffusion of the gas out of the vesicle may be impeded. Preferably, the gas entrapped in the vesicle has a solubility less than that of oxygen, that is, about 1 part gas in about 32 parts water. See *Matheson Gas Data Book,* 1966, Matheson Company Inc. More preferably, the gas entrapped in the vesicle possesses a solubility in water less than that of air; and even more preferably, the gas entrapped in the vesicle possesses a solubility in water less than that of nitrogen.

It may be desirable, in cetain embodiments, to formulate vesicles from substantially impermeable polymeric materials. In these embodiments, it is generally unnecessary to employ a gas which is highly insoluble also. For example, stable vesicle compositions which comprise substantially impermeable polymeric materials may be formulated with gases having higher solubilities, for example, air or nitrogen.

In addition to, or instead of, the lipid, proteinaceous and/or polymeric compounds discussed above, the compositions described herein may comprise one or more stabilizing materials. Exemplary of such stabilizing materials are, for example, biocompatible polymers. The stabilizing materials may be employed to desirably assist in the formation of vesicles and/or to assure substantial encapsulation of the gases or gaseous precursors. Even for relatively insoluble, non-diffusible gases, such as perfluoropropane or sulfur hexafluoride, improved vesicle compositions may be obtained when one or more stabilizing materials are utilized in the formation of the gas and gaseous precursor filled vesicles. These compounds may help improve the stability and the integrity of the vesicles with regard to their size, shape and/or other attributes.

The terms "stable" or "stabilized", as used herein, means that the vesicles may be substantially resistant to degradation, including, for example, loss of vesicle structure or encapsulated gas or gaseous precursor, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and gaseous precursor filled vesicles, may also be stable even under adverse conditions, such as temperatures and pressures which are above or below those experienced under normal ambient conditions.

The stability of the vesicles described herein may be attributable, at least in part, to the materials from which the vesicles are made, including, for example, the lipids, polymers and/or proteins described above, and it is often not necessary to employ additional stabilizing materials, although it is optional and may be preferred to do so. Such additional stabilizing materials and their characteristics are described more fully hereinafter.

The materials from which the vesicles are constructed are preferably biocompatible lipid, protein or polymer materials, and of these, the biocompatible lipids are preferred. In addition, because of the ease of formulation, including the capability of preparing vesicles immediately prior to administration, these vesicles may be conveniently made on site.

The biocompatible polymers useful as stabilizing materials for preparing the gas and gaseous precursor filled vesicles may be of natural, semi-synthetic (modified natural) or synthetic origin. As used herein, the term polymer denotes a compound comprised of two or more repeating monomeric units, and preferably 10 or more repeating monomeric units. The phrase semi-synthetic polymer (or modified natural polymer), as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, polydextrose, pustulan, chitin, agarose, keratan, chondroitan, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinylchloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof. Methods for the preparation of vesicles which employ polymers as stabilizing compounds will be readily apparent to those skilled in the art, once armed with the present disclosure, when the present disclosure is coupled with information known in the art, such as that described and referred to in Unger, U.S. Pat. No. 5,205,290, the disclosures of which are hereby incorporated herein by reference, in their entirety.

Particularly preferred embodiments of the present invention involve vesicles which comprise three components: (1) a neutral lipid, for example, a nonionic or zwitterionic lipid, (2) a negatively charged lipid, and (3) a lipid bearing a stabilizing material, for example, a hydrophilic polymer. Preferably, the amount of the negatively charged lipid will be greater than about 1 mole percent of the total lipid present, and the amount of lipid bearing a hydrophilic polymer will be greater than about 1 mole percent of the total lipid present. Exemplary and preferred negatively charged lipids include phosphatidic acids. The lipid bearing a hydrophilic polymer will desirably be a lipid covalently linked to the polymer, and the polymer will preferably have a weight average molecular weight of from about 400 to about 100,000. Suitable hydrophilic polymers are preferably selected from the group consisting of polyethylene glycol (PEG), polypropylene glycol, polyvinylalcohol, and polyvinylpyrrolidone and copolymers thereof, with PEG polymers being preferred. Preferably, the PEG polymer has a molecular weight of from about 1000 to about 7500, with molecular weights of from about 2000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other phospholipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoylphosphatidylethanol-amine-polyethylene glycol 5000 (DSPE-PEG5000).

In certain preferred embodiments of the present invention, the lipid compositions may include about 77.5 mole % DPPC, 12.5 mole % of DPPA, and 10 mole % of DPPE-PEG5000. Also preferred are compositions which comprise about 80 to about 90 mole % DPPC, about 5 to about 15 mole % DPPA and about 5 to about 15 mole % DPPE-PEG5000. Especially preferred are compositions which comprise DPPC, DPPA and DPPE-PEG5000 in a mole % ratio of 82:10:8, respectively. DPPC is substantially neutral, since the phosphatidyl portion is negatively charged and the choline portion is positively charged. Consequently, DPPA, which is negatively charged, may be added to enhance stabilization in accordance with the mechanism described above. DPPE-PEG provides a pegylated material bound to the lipid membrane or skin of the vesicle by the DPPE moiety, with the PEG moiety free to surround the vesicle membrane or skin, and thereby form a physical barrier to various enzymatic and other endogenous agents in the body whose function is to degrade such foreign materials. The DPPE-PEG may provide more vesicles of a smaller size which are safe and stable to pressure when combined with other lipids, such as DPPC and DPPA, in the given ratios. It is also theorized that the pegylated material, because of its structural similarity to water, may be able to defeat the action of the macrophages of the human immune system, which would otherwise tend to surround and remove the foreign object. The result is an increase in the time during which the stabilized vesicles may function as diagnostic imaging contrast media.

The vesicle compositions may be prepared from other materials, in addition to the materials described above, provided that the vesicles so prepared meet the stability and other criteria set forth herein. These materials may be basic and fundamental, and form the primary basis for creating or establishing the stabilized gas and gaseous precursor filled vesicles. On the other hand, they may be auxiliary, and act as subsidiary or supplementary agents which can enhance the functioning of the basic stabilizing material or materials, or contribute some desired property in addition to that afforded by the basic stabilizing material.

However, it is not always possible to determine whether a given material is a basic or an auxiliary agent, since the functioning of the material in question is determined empirically, for example, by the results produced with respect to producing stabilized vesicles. As examples of how these basic and auxiliary materials may function, it has been observed that the simple combination of a biocompatible lipid and water or saline when shaken will often give a cloudy solution subsequent to autoclaving for sterilization. Such a cloudy solution may function as a contrast agent, but is aesthetically objectionable and may imply instability in the form of undissolved or undispersed lipid particles. Cloudy solutions may be also undesirable where the undissolved particulate matter has a diameter of greater than about 7 µm, and especially greater than about 10 µm. Manufacturing steps, such as sterile filtration, may also be problematic with solutions which contain undissolved particulate matter. Thus, propylene glycol may be added to remove this cloudiness by facilitating dispersion or dissolution of the lipid particles. The propylene glycol may also function as a wetting agent which can improve vesicle formation and stabilization by increasing the surface tension on the vesicle membrane or skin. It is possible that the propylene glycol can also function as an additional layer that may coat the membrane or skin of the vesicle, thus providing additional stabilization. As examples of such further basic or auxiliary stabilizing materials, there are conventional surfactants which may be used; see D'Arrigo U.S. Pat. Nos. 4,684,479 and 5,215,680.

Additional auxiliary and basic stabilizing materials include such agents as peanut oil, canola oil, olive oil, safflower oil, corn oil, or any other oil commonly known to be ingestible which is suitable for use as a stabilizing compound in accordance with the teachings herein. Various auxiliary and basic stabilizing materials are disclosed, for example, in U.S. Pat. No. 5,580,575, the disclosures of which are incorporated herein by reference, in their entirety.

In addition, compounds used to make mixed micelle systems may be suitable for use as basic or auxiliary stabilizing materials, and these include, for example, lauryltrimethylammonium bromide (dodecyl-), cetyltrimethylammonium bromide (hexadecyl-), myristyltrimethylammonium bromide (tetradecyl-), alkyldimethylbenzylammonium chloride (where alkyl is $C_{12}$, $C_{14}$ or $C_{16}$,), benzyldimethyldodecylammonium bromide/chloride, benzyldimethyl hexadecylammonium bromide/chloride, benzyldimethyl tetradecylammonium bromide/chloride, cetyldimethylethylammonium bromide/chloride, or cetylpyridinium bromide/chloride.

It has also been found that the gas and gaseous precursor filled vesicles used in the present invention may be controlled according to size, solubility and heat stability by choosing from among the various additional or auxiliary stabilizing materials described herein. These materials can affect these parameters of the vesicles, especially vesicles formulated from lipids, not only by their physical interaction with the membranes, but also by their ability to modify the viscosity and surface tension of the surface of the gas and gaseous precursor filled vesicle. Accordingly, the gas and gaseous precursor filled vesicles used in the present invention may be favorably modified and further stabilized, for example, by the addition of one or more of a wide variety of (a) viscosity modifiers, including, for example, carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000; (b) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, and poloxamer 181, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan mono-oleate, sorbitan mono-palmitate, sorbitan monostearate, stearic acid, trolamine, and emulsifying wax; (c) suspending and/or viscosity-increasing agents, including, for example, acacia, agar, alginic acid, aluminum mono-stearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, Zeolites®, methylcellulose, pectin, polyethylene oxide, povidone, propylene glycol alginate, silicon dioxide, sodium alginate, tragacanth, xanthan gum, α-d-gluconolactone, glycerol and mannitol; (d) synthetic suspending agents, such as polyethylene glycol (PEG), polyvinylpyrrolidone (PVP), polyvinylalcohol (PVA), polypropylene glycol (PPG), and polysorbate; and (e) tonicity raising agents which stabilize and add tonicity, including, for example, sorbitol, mannitol, trehalose, sucrose, propylene glycol and glycerol.

A wide variety of methods are available for the preparation of lipid and/or vesicle compositions, such as micelles and/or liposomes. Included among these methods are, for example, shaking, drying, gas-installation, spray drying, and the like. Suitable methods for preparing vesicle compositions from lipids are described, for example, in Unger et al., U.S. Pat. No. 5,469,854, the disclosures of which are incorporated herein by reference. As noted above, the vesicles are preferably prepared from lipids which remain in the gel state.

With particular reference to the preparation of micelle compositions, the following discussion is provided. Micelles may be prepared using any one of a variety of conventional micellar preparatory methods which will be apparent to those skilled in the art. These methods typically involve suspension of one or more lipid compounds in an organic solvent, evaporation of the solvent, resuspension in an aqueous medium, sonication and centrifugation. The foregoing methods, as well as others, are discussed, for example, in Canfield et al., *Methods in Enzymology*, Vol. 189, pp. 418–422 (1990); El-Gorab et al, *Biochem. Biophys. Acta*, Vol. 306, pp. 58–66 (1973); *Colloidal Surfactant*, Shinoda, K., Nakagana, Tamamushi and Isejura, Academic Press, NY (1963) (especially "The Formation of Micelles", Shinoda, Chapter 1, pp. 1–88); *Catalysis in Micellar and Macromolecular Systems*, Fendler and Fendler, Academic Press, NY (1975). The disclosures of each of the foregoing publications are incorporated by reference herein, in their entirety.

As noted above, the vesicle composition may comprise liposomes. A wide variety of methods are available in connection with the preparation of liposome compositions. Accordingly, the liposomes may be prepared using any one of a variety of conventional liposomal preparatory techniques which will be apparent to those skilled in the art. These techniques include, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. See, e.g., Madden et al., *Chemistry and Physics of Lipids*, 1990 53, 37–46, the disclosures of which are hereby incorporated herein by reference in their entirety. Suitable freeze-thaw techniques are described, for example, in International Application Serial No. PCT/US89/05040, filed Nov. 8, 1989, the disclosures of which are incorporated herein by reference in their entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing. This may be achieved, for example, by the use of a mechanical shaking device, such as a Wig-L-Bug™ (Crescent Dental, Lyons, Ill.), a Mixomat (Degussa AG, Frankfurt, Germany), a Capmix (Espe Fabrik Pharmazeutischer Praeparate GMBH & Co., Seefeld, Oberay Germany), a Silamat Plus (Vivadent, Lechtenstein), or a Vibros (Quayle Dental, Sussex, England). Conventional microemulsification equipment, such as a Microfluidizer™ (Microfluidics, Woburn, Mass.) may also be used.

Spray drying may be also employed to prepare the gas-filled vesicles. Utilizing this procedure, the lipids may be pre-mixed in an aqueous environment and then spray dried to produce gas-filled vesicles. The vesicles may be stored under a headspace of a desired gas.

Many liposomal preparatory techniques which may be adapted for use in the preparation of vesicle compositions are discussed, for example, in U.S. Pat. No. 4,728,578; U.K. Patent Application GB 2193095 A; U.S. Pat. No. 4,728,575; U.S. Pat. No. 4,737,323; International Application Serial No. PCT/US85/01161; Mayer et al., *Biochimica et Biophysica Acta*, Vol. 858, pp. 161–168 (1986); Hope et al., *Biochimica et Biophysica Acta*, Vol. 812, pp. 55–65 (1985); U.S. Pat. No. 4,533,254; Mayhew et al., *Methods in Enzymology*, Vol. 149, pp. 64–77 (1987); Mayhew et al., *Biochimica et Biophysica Acta*, Vol 755, pp. 169–74 (1984); Cheng et al, *Investigative Radiology*, Vol. 22, pp. 47–55 (1987); International Application Serial No. PCT/US89/05040; U.S. Pat. No. 4,162,282; U.S. Pat. No. 4,310,505; U.S. Pat. No. 4,921,706; and Liposome *Technology*, Gregoriadis, G., ed., Vol. I, pp. 29–31, 51–67 and 79–108 (CRC Press Inc., Boca Raton, Fla. 1984), the disclosures of each of which are hereby incorporated by reference herein, in their entirety.

Lipid compositions comprising a gas can be prepared by agitating an aqueous solution containing, if desired, a stabilizing material, in the presence of a gas. The term "agitating," as used herein, means any shaking motion of an aqueous solution such that gas may be introduced from the local ambient environment into the aqueous solution. This agitation is preferably conducted at a temperature below the gel to liquid crystalline phase transition temperature of the lipid. The shaking involved in the agitation of the solutions is preferably of sufficient force to result in the formation of a lipid composition, including vesicle compositions, and particularly vesicle compositions comprising gas filled vesicles. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

The shaking may occur manually or by machine. Mechanical shakers that may be used include, for example, a shaker table such as a VWR Scientific (Cerritos, Calif.) shaker table, as well as any of the shaking devices described hereinbefore, with the Capmix (Espe Fabrik Pharmazeutischer Praeparate GMBH & Co., Seefeld, Oberay Germany) being preferred. It has been found that certain modes of shaking or vortexing can be used to make vesicles within a preferred size range. Shaking is preferred, and it is preferred that the shaking be carried out using the Espe Capmix mechanical shaker. In accordance with this preferred method, it is preferred that a reciprocating motion be utilized to generate the lipid compositions, and particularly vesicle compositions. It is even more preferred that the motion be reciprocating in the form of an arc. It is contemplated that the rate of reciprocation, as well as the arc thereof, is particularly important in connection with the formation of vesicles. Preferably, the number of reciprocations or full cycle oscillations may be from about 1000 to about 20,000 per minute. More preferably, the number of reciprocations or oscillations may be from about 2500 to about 8000 per minute, with from about 3300 to about 5000 reciprocations or oscillations per minute being even more preferred. Of course, the number of oscillations may be dependent upon the mass of the contents being agitated. Generally speaking, a larger mass may require fewer oscillations. Another means for producing shaking includes the action of gas emitted under high velocity or pressure.

It will also be understood that preferably, with a larger volume of aqueous solution, the total amount of force may be correspondingly increased. Vigorous shaking is defined as at least about 60 shaking motions per minute, and is preferred. Vortexing at about 60 to about 300 revolutions per minute is more preferred. Vortexing at about 300 to about 1800 revolutions per minute is even more preferred.

In addition to the simple shaking methods described above, more elaborate methods can also be employed. Such elaborate methods include, for example, liquid crystalline shaking gas instillation processes and vacuum drying gas instillation processes, such as those described in U.S. Pat. No. 5,580,575, the disclosures of which are incorporated herein by reference, in their entirety. Although any of a number of varying techniques can be used, the vesicle compositions employed in the present invention are preferably prepared using a shaking technique. Preferably, the shaking technique involves agitation with a mechanical shaking apparatus, such as an Espe Capmix (Seefeld, Oberay Germany), using, for example, the techniques disclosed in U.S. Pat. No. 5,542,935, the disclosures of which are hereby incorporated herein by reference in their entirety.

The size of gas filled vesicles can be adjusted, if desired, by a variety of procedures, including, for example, microemulsification, vortexing, extrusion, filtration, sonication, homogenization, repeated freezing and thawing cycles, extrusion under pressure through pores of defined size, and similar methods. Gas filled vesicles prepared in accordance with the methods described herein can range in size from less than about 1 $\mu$m to greater than about 100 $\mu$m. In addition, after extrusion and sterilization procedures, which are discussed in detail below, agitation or shaking may provide vesicle compositions which can contain substantially no or minimal residual anhydrous lipid phase in the remainder of the solution. (Bangham, A. D., Standish, M. M, & Watkins, J. C., *J. Mol. Biol.* Vol. 13, pp. 238–252 (1965). If desired, the vesicles may be used as they are formed, without any attempt at further modification of the size thereof. For intravascular use, the vesicles preferably have diameters of less than about 30 $\mu$m, and more preferably, less than about 12 $\mu$m. For targeted intravascular use including, for example, binding to certain tissue, such as cancerous tissue, the vesicles may be significantly smaller, for example, less than about 100 nm in diameter. For enteric or gastrointestinal use, the vesicles may be significantly larger, for example, up to a millimeter in size. Preferably, the vesicles may be sized to have diameters of from about 2 $\mu$m to about 100 $\mu$m.

The gas filled vesicles may be sized by a simple process of extrusion through filters wherein the filter pore sizes control the size distribution of the resulting gas filled vesicles. By using two or more cascaded or stacked set of filters, for example, a 10 $\mu$m filter followed by an 8 $\mu$m filter, the gas filled vesicles can be selected to have a very narrow size distribution around 7 to 9 $\mu$m. After filtration, these gas filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and may be carried out by a step of extracting which comprises extruding the vesicles from the barrel through the filter fitted to the syringe between the barrel and the needle, thereby sizing the vesicles before they are administered to a patient. The step of extracting may also comprise drawing the vesicles into the syringe, where the filter may function in the same way to size the vesicles upon entrance into the syringe. Another alternative is to fill such a syringe with vesicles which have already been sized by some other means, in which case the filter may function to ensure that only vesicles within the desired size range, or of the desired maximum size, are subsequently administered by extrusion from the syringe.

In certain preferred embodiments, the vesicle compositions may be heat sterilized or filter sterilized and extruded through a filter prior to shaking. Generally speaking, vesicle compositions comprising a gas may be heat sterilized, and vesicle compositions comprising gaseous precursors may be filter sterilized. Once gas filled vesicles are formed, they may be filtered for sizing as described above. Performing these steps prior to the formation of gas and gaseous precursor filled vesicles provide sterile gas filled vesicles ready for administration to a patient. For example, a mixing vessel such as a vial or syringe may be filled with a filtered lipid and/or vesicle composition, and the composition may be sterilized within the mixing vessel, for example, by autoclaving. Gas may be instilled into the composition to form gas filled vesicles by shaking the sterile vessel. Preferably, the sterile vessel is equipped with a filter positioned such that the gas filled vesicles pass through the filter before contacting a patient.

The step of extruding the solution of lipid compound through a filter decreases the amount of unhydrated material by breaking up any dried materials and exposing a greater surface area for hydration. Preferably, the filter has a pore size of about 0.1 to about 5 μm, more preferably, about 0.1 to about 4 μm, even more preferably, about 0.1 to about 2 μm, and still more preferably, about 1 μm. Unhydrated compound, which is generally undesirable, appears as amorphous clumps of non-uniform size.

The sterilization step provides a composition that may be readily administered to a patient for diagnostic imaging including, for example, ultrasound or CT. In certain preferred embodiments, sterilization may be accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes.

If desired, the extrusion and heating steps, as outlined above, may be reversed, or only one of the two steps can be used. Other modes of sterilization may be used, including, for example, exposure to gamma radiation.

In addition to the aforementioned embodiments, gaseous precursors contained in vesicles can be formulated which, upon activation, for example, by exposure to elevated temperature, varying pH, or light, may undergo a phase transition from, for example, a liquid, including a liquid entrapped in a vesicle, to a gas, expanding to create the gas filled vesicles described herein. This technique is described in detail in now U.S. Pat. Nos. 5,585,112 and 5,585,112, the disclosures of which are incorporated herein by reference, in their entirety.

The preferred method of activating the gaseous precursor is by exposure to elevated temperature. Activation or transition temperature, and like terms, refer to the boiling point of the gaseous precursor and is the temperature at which the liquid to gaseous phase transition of the gaseous precursor takes place. Useful gaseous precursors are those materials which have boiling points in the range of about −100° C. to about 70° C. The activation temperature is particular to each gaseous precursor. An activation temperature of about 37° C., or about human body temperature, is preferred for gaseous precursors in the context of the present invention. Thus, in preferred form, a liquid gaseous precursor is activated to become a gas at about 37° C. or below. The gaseous precursor may be in liquid or gaseous phase for use in the methods of the present invention.

The methods of preparing the gaseous precursor filled vesicles may be carried out below the boiling point of the gaseous precursor such that a liquid is incorporated, for example, into a vesicle. In addition, the methods may be conducted at the boiling point of the gaseous precursor, such that a gas is incorporated, for example, into a vesicle. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature-activated gaseous precursor filled vesicles may be carried out at a temperature below the boiling point of the gaseous precursor. In this embodiment, the gaseous precursor may be entrapped within a vesicle such that the phase transition does not occur during manufacture. Instead, the gaseous precursor filled vesicles are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the vesicles upon attaining the gaseous state may be determined.

Alternatively, the gaseous precursors may be utilized to create stable gas filled vesicles which are pre-formed prior to use. In this embodiment, the gaseous precursor may be added to a container housing a lipid composition at a temperature below the liquid-gaseous phase transition temperature of the respective gaseous precursor. As the temperature is increased, and an emulsion is formed between the gaseous precursor and liquid solution, the gaseous precursor undergoes transition from the liquid to the gaseous state. As a result of this heating and gas formation, the gas displaces the air in the head space above the liquid mixture so as to form gas filled vesicles which may entrap the gas of the gaseous precursor, ambient gas (e.g. air), or coentrap gas state gaseous precursor and ambient air. This phase transition can be used for optimal mixing and formation of the contrast agent. For example, the gaseous precursor, perfluorobutane, can be entrapped in the lipid vesicles and as the temperature is raised beyond the boiling point of perfluorobutane (4° C.), perfluorobutane gas is entrapped in the vesicles.

Accordingly, the gaseous precursors may be selected to form gas filled vesicles in vivo or may be designed to produce the gas filled vesicles in situ, during the manufacturing process, on storage, or at some time prior to use.

As a further embodiment of this invention, by preforming the gaseous precursor in the liquid state into an aqueous emulsion, the maximum size of the vesicle may be estimated by using the ideal gas law, once the transition to the gaseous state is effectuated. For the purpose of making gas filled vesicles from gaseous precursors, the gas phase may be assumed to form instantaneously and substantially no gas in the newly formed vesicle has been depleted due to diffusion into the liquid, which is generally aqueous in nature. Hence, from a known liquid volume in the emulsion, one may predict an upper limit to the size of the gas filled vesicle.

In embodiments of the present invention, a mixture of a lipid compound and a gaseous precursor, containing liquid droplets of defined size, may be formulated such that upon reaching a specific temperature, for example, the boiling point of the gaseous precursor, the droplets may expand into gas filled vesicles of defined size. The defined size may represent an upper limit to the actual size because the ideal gas law generally cannot account for such factors as gas diffusion into solution, loss of gas to the atmosphere, and the effects of increased pressure.

The ideal gas law, which can be used for calculating the increase in the volume of the gas bubbles upon transitioning from liquid to gaseous states, is as follows:

$$PV = nRT$$

where

P is pressure in atmospheres (atm);

V is volume in liters (L);

n is moles of gas;

T is temperature in degrees Kelvin (K); and

R is the ideal gas constant (22.4 L-atm/K-mole).

With knowledge of volume, density, and temperature of the liquid in the mixture of liquids, the amount, for example, in moles, and volume of liquid precursor may be calculated which, when converted to a gas, may expand into a vesicle of known volume. The calculated volume may reflect an upper limit to the size of the gas filled vesicle, assuming instantaneous expansion into a gas filled vesicle and negligible diffusion of the gas over the time of the expansion.

Thus, for stabilization of the precursor in the liquid state in a mixture wherein the precursor droplet is spherical, the volume of the precursor droplet may be determined by the equation:

$$\text{Volume (spherical vesicle)} = 4/3\ \pi r^3$$

where r is the radius of the sphere.

Thus, once the volume is predicted, and knowing the density of the liquid at the desired temperature, the amount of liquid gaseous precursor in the droplet may be determined. In more descriptive terms, the following can be applied:

$$V_{gas} = 4/3\ \pi (r_{gas})^3$$

by the ideal gas law, $$PV = nRT$$

substituting reveals, $$V_{gas} = nRT/P_{gas}$$

or, $$n = 4/3 [\pi r_{gas}^3] P/RT \quad \text{(A)}$$

amount $n = 4/3 [\pi r_{gas}^3 P/RT] \cdot MW_n$

Converting back to a liquid volume $$V_{liq} = [4/3 [\pi r_{gas}^3] P/RT] \cdot MW_n/D] \quad \text{(B)}$$

where D is the density of the precursor.

Solving for the diameter of the liquid droplet, $$\text{diameter}/2 = [3/4\pi [4/3 \cdot [\pi r_{gas}^3] P/RT] MW_n/D]^{1/3} \quad \text{(C)}$$

which reduces to $$\text{Diameter} = 2[[r_{gas}^3] P/RT\ [MW_n/D]]^{1/3}.$$

As a further means of preparing vesicles of the desired size for use in the methods of the present invention, and with a knowledge of the volume and especially the radius of the liquid droplets, one can use appropriately sized filters to size the gaseous precursor droplets to the appropriate diameter sphere.

A representative gaseous precursor may be used to form a vesicle of defined size, for example, 10 $\mu$m diameter. In this example, the vesicle may be formed in the bloodstream of a human being, thus the typical temperature would be 37° C. or 310 K. At a pressure of 1 atmosphere and using the equation in (A), $7.54 \times 10^{-17}$ moles of gaseous precursor may be required to fill the volume of a 10 $\mu$m diameter vesicle.

Using the above calculated amount of gaseous precursor and 1-fluorobutane, which possesses a molecular weight of 76.11, a boiling point of 32.5° C. and a density of 0.7789 g/mL at 20° C., further calculations predict that $5.74 \times 10^{-15}$ grams of this precursor may be required for a 10 $\mu$m vesicle. Extrapolating further, and with the knowledge of the density, equation (B) further predicts that $8.47 \times 10^{-16}$ mL of liquid precursor may be necessary to form a vesicle with an upper limit of 10 $\mu$m.

Finally, using equation (C), a mixture, for example, an emulsion containing droplets with a radius of 0.0272 $\mu$m or a corresponding diameter of 0.0544 $\mu$m, may be formed to make a gaseous precursor filled vesicle with an upper limit of a 10 $\mu$m vesicle.

An emulsion of this particular size could be easily achieved by the use of an appropriately sized filter. In addition, as seen by the size of the filter necessary to form gaseous precursor droplets of defined size, the size of the filter may also suffice to remove any possible bacterial contaminants and, hence, can be used as a sterile filtration as well.

This embodiment for preparing gas filled vesicles may be applied to all gaseous precursors activated by temperature. In fact, depression of the freezing point of the solvent system allows the use of gaseous precursors which may undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point may be lowered by an amount that is dependent upon the composition of the solution. Thus, as defined by Wall, one can express the freezing point depression of the solvent by the following equation:

$$\ln x_a = \ln(1 - x_b) = \Delta H_{fus}/R(1/T_o - 1/T)$$

where $x_a$ is the mole fraction of the solvent;

$x_b$ is the mole fraction of the solute;

$\Delta H_{fus}$ is the heat of fusion of the solvent; and $T_o$ is the normal freezing point of the solvent.

The normal freezing point of the solvent can be obtained by solving the equation. If $x_b$ is small relative to $x_a$, then the above equation may be rewritten as follows.

$$x^b = \Delta H_{fus}/R[T-T_o/T_oT] \approx \Delta H_{fus}\Delta T/RT_o^2$$

The above equation assumes the change in temperature $\Delta T$ is small compared to $T_2$. This equation can be simplified further by expressing the concentration of the solute in terms of molality, m (moles of solute per thousand grams of solvent). Thus, the equation can be rewritten as follows.

$$X_b = m/[m+1000/m_a] \approx mMa/1000$$

where Ma is the molecular weight of the solvent.

Thus, substituting for the fraction xb:

$$\Delta T = [M_a RT_o^2/1000\Delta H_{fus}]m$$

or $$\Delta T = K_f m, \text{ where}$$

$$K_f = M_a RT_o^2/1000\Delta H_{fus}$$

$K_f$ is the molal freezing point and is equal to 1.86 degrees per unit of molal concentration for water at one atmosphere pressure. The above equation may be used to accurately determine the molal freezing point of solutions of gaseous-precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles include:

(a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 μm. Alternatively, filtering may be performed during in vivo administration of the vesicles such that a filter of about 0.22 μm is employed;

(b) microemulsification, whereby an aqueous mixture of gaseous precursor is emulsified by agitation and heated to form, for example, vesicles prior to administration to a patient;

(c) heating a gaseous precursor in a mixture, with or without agitation, whereby the less dense gaseous precursor filled vesicles may float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying may be useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state. For example, perfluorobutane can be used to fill dried vesicles at temperatures above 4° C. (the boiling point of perfluorobutane).

Preferred methods for preparing the temperature activated gaseous precursor filled vesicles comprise shaking an aqueous solution having a lipid compound in the presence of a gaseous precursor at a temperature below the liquid state to gas state phase transition temperature of the gaseous precursor. This is preferably conducted at a temperature below the gel state to liquid crystalline state phase transition temperature of the lipid. The mixture may be then heated to a temperature above the liquid state to gas state phase transition temperature of the gaseous precursor which can cause the precursor to volatilize and expand. Heating may be then discontinued, and the temperature of the mixture may be allowed to drop below the liquid state to gas state phase transition temperature of the gaseous precursor. Shaking of the mixture may take place during the heating step, or subsequently after the mixture is allowed to cool.

Other methods for preparing gaseous precursor filled vesicles can involve shaking an aqueous solution of, for example, a lipid and a gaseous precursor, and separating the resulting gaseous precursor filled vesicles.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.* 1978, 75, 4194–4198. In contrast, the vesicles made according to certain preferred embodiments described herein are gaseous precursor filled, which imparts greater flexibility, since gaseous precursors after gas formation are more compressible and compliant than an aqueous solution.

The preparatory methods may involve shaking an aqueous solution comprising a lipid, in the presence of a temperature activatable gaseous precursor. Preferably, the shaking is of sufficient force such that a foam is formed within a short period of time, such as about 30 minutes, and preferably within about 20 minutes, and more preferably, within about 10 minutes. The shaking may involve microemulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, the mechanical shakers described hereinbefore, with an Espe Capmix (Seefeld, Oberay Germany) being preferred. Another means for producing shaking includes the action of gaseous precursor emitted under high velocity or pressure.

According to the methods described herein, a gas, such as air, may also be provided by the local ambient atmosphere. The local ambient atmosphere can include the atmosphere within a sealed container, as well as the external environment. Alternatively, for example, a gas may be injected into or otherwise added to the container having the aqueous lipid solution or into the aqueous lipid solution itself to provide a gas other than air. Gases that are lighter than air are generally added to a sealed container, while gases heavier than air can be added to a sealed or an unsealed container. Accordingly, the present invention includes co-entrapment of air and/or other gases along with gaseous precursors.

Hence, the gaseous precursor filled vesicles can be used in substantially the same manner as the gas filled vesicles described herein, once activated by application to the tissues of a host, where such factors as temperature or pH may be used to cause generation of the gas. It is preferred that the gaseous precursors undergo phase transitions from liquid to gaseous states at near the normal body temperature of the host, and are thereby activated, for example, by the in vivo temperature of the host so as to undergo transition to the gaseous phase therein. This can occur where, for example, the host tissue is human tissue having a normal temperature of about 37° C. and the gaseous precursors undergo phase transitions from liquid to gaseous states near 37° C.

As noted above, the lipid and/or vesicle compositions may be sterilized by autoclave or sterile filtration if these processes are performed before the installation step or prior to temperature mediated conversion of the temperature sensitive gaseous precursors within the compositions. Alternatively, one or more anti-bactericidal agents and/or preservatives may be included in the formulation of the compositions, such as sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, may be necessary where the stabilized vesicles are used for imaging under invasive circumstances, for example, intravascularly or intraperitonealy. The appropriate means of sterilization will be apparent to the artisan based on the present disclosure.

Vesicle compositions which comprise vesicles formulated from proteins (also referred to as protein encapsulated microbubbles), such as albumin vesicles, may be prepared by various processes, as will be readily apparent to those skilled in the art, once armed with the present disclosure. Suitable methods include those described, for example, in Feinstein, U.S. Pat. Nos. 4,572,203, 4,718,433 and 4,774,958, and Cerny et al., U.S. Pat. No. 4,957,656, the disclosures of which are hereby incorporated herein by reference, in their entirety. Included among the methods described in the aforementioned patents for the preparation of protein-based vesicles are methods which involve sonicating a solution of a protein. In preferred form, the starting material may be an aqueous solution of a heat-denaturable, water-soluble biocompatible protein. The encapsulating protein is preferably heat-sensitive so that it can be partially insolubilized by heating during sonication. Suitable heat-sensitive proteins include, for example, albumin, hemoglobin, collagen, and the like. Preferably, the protein is a human protein, with human serum albumin (HSA) being more preferred. HSA is available commercially as a sterile 5% aqueous solution, which is suitable for use in the preparation of protein-based vesicles. Of course, as would be apparent to one of ordinary skill in the art, other concentrations of albumin, as well as other proteins which are heat-denaturable, can be used to prepare the vesicles. Generally speaking, the concentration of HSA can vary and may range from about 0.1 to about 25% by weight, and all combinations and subcombinations of ranges therein. It may be preferable, in connection with certain methods for the preparation of protein-based vesicles, to utilize the protein in the form of a dilute aqueous solution. For albumin, it may be preferred to utilize an aqueous solution containing from about 0.5 to about 7.5% by weight albumin, with concentrations of less than about 5% by weight being preferred, for example, from aobut 0.5 to about 3% by weight.

The protein-based vesicles may be prepared using equipment which is commercially available. For example, in connection with a feed preparation operation as disclosed, for example, in Cerny, et al., U.S. Pat. No. 4,957,656, stainless steel tanks which are commercially available from Walker Stainless Equipment Co. (New Lisbon, Wis.), and process filters which are commercially available from Millipore (Bedford, Mass.), may be utilized.

The sonication operation may utilize both a heat exchanger and a flow through sonciating vessel, in series. Heat exhanger equipment of this type may be obatined from ITT Standard (Buffalo, N.Y.). The heat exchanger maintains operating temperature for the sonciation process, with temperature controls ranging from about 65° C. to about 80° C., depending on the makeup of the media. The vibration frequency of the sonication equipment may vary over a wide range, for example, from about 5 to about 40 kilohertz (kHz), with a majority of the commerically available sonicators operating at about 10 or 20 kHz. Suitable sonicating equipment include, for example, a Sonics & Materials Vibra-Cell, equipped with a flat-tipped sonicator horn, commercially available from Sonics & Materials, Inc. (Danbury, Conn.). The power applied to the sonicator horn can be varied over power settings scaled from 1 to 10 by the manufacturer, as with Sonics & Materials Vibra-Cell Model VL1500. An intermediate power setting, for example, from 5 to 9, can be used. It is preferred that the vibrational frequency and the power supplied be sufficeint to produce cavitation in the liquid being sonicated. Feed flow rates may range from about 50 mL/min to about 1000 mL/min, and all combinations and subcombinations of ranges therein. Residence times in the sonication vessel can range from about 1 second to about 4 minutes, and gaseous fluid addition rates may range from about 10 cubic centimeters (cc) per minute to about 100 cc/min, or 5% to 25% of the feed flow rate, and all combinations and subcombinations of ranges therein.

It may be preferable to carry out the sonication in such a manner to produce foaming, and especially intense foaming, of the solution. Generally speaking, intense foaming and aerosolating are important for obtaining a contrast agent having enhanced concentration and stability. To promote foaiming, the power input to the sonicator horn may be increased, and the process may be operated under mild pressure, for example, about 1 to about 5 psi. Foaming may be easily detected by the cloudy appearance of the solution, and by the foam produced.

Suitable methods for the preparation of protein-based vesicles may also involve physically or chemically altering the protein or protein derivative in aqueous solution to denature or fix the material. For example, protein-based vesicles may be prepared from a 5% aqueous solution of HSA by heating after formation or during formation of the contrast agent via sonication. Chemical alteration may involve chemically denaturing or fixing by binding the protein with a difunctional aldehyde, such as gluteraldehyde. For example, the vesicles may be reacted with 0.25 grams of 50% aqueous gluteradehyde per gram of protein at pH 4.5 for 6 hours. The unreacted gluteraldehyde may then be washed away from the protein.

Vesicle compositions which comprise vesicles formulated from polymers may be prepared by various processes, as will be readily apparent to those skilled in the art, once armed with the present disclosure. Exemplary processes include, for example, interfacial polymerization, phase separation and coacervation, multiorifice centrifugal preparation, and solvent evaporation. Suitable procedures which may be employed or modified in accordance with the present disclosure to prepare vesicles from polymers include those procedures disclosed in Garner et al., U.S. Pat. No. 4,179,546, Garner, U.S. Pat. No. 3,945,956, Cohrs et al., U.S. Pat. No. 4,108,806, Japan Kokai Tokkyo Koho 62 286534, British Patent No. 1,044,680, Kenaga et al., U.S. Pat. No. 3,293,114, Morehouse et al., U.S. Pat. No. 3,401,475, Walters, U.S. Pat. No. 3,479,811, Walters et al., U.S. Patent No. 3,488,714, Morehouse et al., U.S. Pat. No. 3,615,972, Baker et al., U.S. Pat. No. 4,549,892, Sands et al., U.S. Pat. No. 4,540,629, Sands et al., U.S. Pat. No. 4,421,562, Sands, U.S. Pat. No. 4,420,442, Mathiowitz et al., U.S. Pat. No. 4,898,734, Lencki et al., U.S. Pat. No. 4,822,534, Herbig et al., U.S. Pat. No. 3,732,172, Himmel et al., U.S. Pat. No. 3,594,326, Sommerville et al., U.S. Pat. No. 3,015,128, Deasy, *Microencapsulation and Related Drug Processes*, Vol. 20, Chs. 9 and 10, pp. 195–240 (Marcel Dekker, Inc., N.Y., 1984), Chang et al., *Canadian J. of Physiology and Pharmacology*, Vol 44, pp. 115–129 (1966), and Chang, *Science*, Vol. 146, pp. 524–525 (1964), the disclosures of each of which are incorporated herein by reference in their entirety.

In accordance with a preferred synthesis protocol, the vesicles may be prepared using a heat expansion process, such as, for example, the process described in Garner et al., U.S. Pat. No. 4,179,546, Garner, U.S. Pat. No. 3,945,956, Cohrs et al., U.S. Pat. No. 4,108,806, British Patent No. 1,044,680, and Japan Kokai Tokkyo Koho 62 286534. In general terms, the heat expansion process may be carried out by preparing vesicles of an expandable polymer or copolymer which may contain in their void (cavity) a volatile liquid (gaseous precursor). The vesicle is then heated, plasticising the vesicle and converting the volatile liquid into a gas, causing the vesicle to expand to up to about several times its original size. When the heat is removed, the thermoplastic polymer retains at least some of its expanded shape. Vesicles produced by this process tend to be of particularly low density, and are thus preferred. The foregoing described process is well known in the art, and may be referred to as the heat expansion process for preparing low density vesicles.

Polymers useful in the heat expansion process will be readily apparent to those skilled in the art and include thermoplastic polymers or copolymers, including polymers or copolymers of many of the monomers described above. Preferable of the polymers and copolymers described above include the following copolymers: polyvinylidene-polyacrylonitrile, polyvinylidene-polyacrylonitrile-polymethyl-methacrylate, and polystyrene-polyacrylonitrile. A most preferred copolymer is polyvinylidene-polyacrylonitrile.

Volatile liquids useful in the heat expansion process will also be well known to those skilled in the art and include: aliphatic hydrocarbons such as ethane, ethylene, propane, propene, butane, isobutane, neopentane, acetylene, hexane, heptane; chlorofluorocarbons such as $CCl_3F$, $CCl_2F_3$, $CClF_3$, $CClF_2$—$CCl_2F_2$, chloroheptafluorocyclobutane, and 1,2-dichlorohexafluorocyclobutane; tetraalkyl silanes, such as tetramethyl silane, trimethylethyl silane, trimethylisopropyl silane, and trimethyl n-propyl silane; as well as perfluorocarbons, including the perfluorocarbons described above. In general, it is important that the volatile liquid not be a solvent for the polymer or copolymer being utilized. It is also preferred that the volatile liquid have a boiling point that is below the softening point of the involved polymer or co-polymer. Boiling points of various volatile liquids and softening points of various polymers and copolymers will be readily ascertainable to one skilled in the art, and suitable combinations of polymers or copolymers and volatile liquids will be easily apparent to the skilled artisan. By way of guidance, and as one skilled in the art would recognize, generally as the length of the carbon chain of the volatile liquid increases, the boiling point of that liquid increases also. Also, mildly preheating the vesicles in water in the presence of hydrogen peroxide prior to definitive heating and expansion may pre-soften the vesicle to allow expansion to occur more readily.

For example, to produce vesicles from synthetic polymers, vinylidene and acrylonitrile may be copolymerized in a medium of isobutane liquid using one or more of the foregoing modified or unmodified literature procedures, such that isobutane becomes entrapped within the vesicles. When such vesicles are then heated to a temperature of from about 80° C. to about 120° C., the isobutane gas expands, which in turn expands the vesicles. After heat is removed, the expanded polyvinylidene and acrylo-nitrile copolymer vesicles remain substantially fixed in their expanded position. The resulting low density vesicles are extremely stable both dry and suspended in an aqueous media. Isobutane is utilized herein merely as an illustrative liquid, with the understanding that other liquids which undergo liquid/gas transitions at temperatures useful for the synthesis of these vesicles and formation of the very low density vesicles upon heating can be substituted for isobutane. Similarly, monomers other than vinylidene and acrylonitrile may be employed in preparing the vesicles.

In certain preferred embodiments, the vesicles which are formulated from synthetic polymers and which may be employed in the methods of the present invention are commercially available from Expancel, Nobel Industries (Sundsvall, Sweden), including EXPANCEL 551 DE™ microspheres. The EXPANCEL 551 DE™ microspheres are composed of a copolymer of vinylidene and acrylonitrile which have encapsulated therein isobutane liquid. Such microspheres are sold as a dry composition and are approximately 50 microns in size. The EXPANCEL 551 DE™ microspheres have a specific gravity of only 0.02 to 0.05, which is between one-fiftieth and one-twentieth the density of water.

As with the preparation of lipid and/or vesicle compositions, a wide variety of techniques are available for the preparation of lipid and/or vesicle formulations. For example, lipid and/or vesicle formulations may be prepared from a mixture of lipid compounds, bioactive agent and gas or gaseous precursor. In this case, lipid and/or vesicle compositions may be prepared as described above in which the compositions also comprise bioactive agent. Thus, for example, micelles can be prepared in the presence of a bioactive agent. In connection with lipid and/or vesicle compositions which comprise a gas, the preparation can involve, for example, bubbling a gas directly into a mixture of lipid compounds and one or more additional materials. Alternatively, the lipid and/or vesicle compositions may be preformed from lipid compounds and gas or gaseous precursor. In the latter case, the bioactive agent may be then added to the lipid and/or vesicle composition prior to use. For example, an aqueous mixture of liposomes and gas may be prepared to which the bioactive agent may be added and which is agitated to provide the liposome formulation. The liposome formulation can be readily isolated since the gas and/or bioactive agent filled liposome vesicles generally float to the top of the aqueous solution. Excess bioactive agent can be recovered from the remaining aqueous solution.

As those skilled in the art will recognize, any of the lipid and/or vesicle compositions and lipid and/or vesicle formulations may be lyophilized for storage, and reconstituted, for example, with an aqueous medium (such as sterile water, phosphate buffered solution, or aqueous saline solution), with the aid of vigorous agitation. To prevent agglutination or fusion of the lipids as a result of lyophilization, it may be useful to include additives which prevent such fusion or agglutination from occurring. Additives which may be useful include sorbitol, mannitol, sodium chloride, glucose, trehalose, polyvinylpyrrolidone and poly(ethylene glycol) (PEG), for example, PEG polymers having a molecular weight of from about 400 to about 10,000, with PEG polymers having molecular weights of about 1000, 3000 (such as PEG3350) and 5000 being preferred. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

As discussed above, the compositions of the present invention, including gas and/or gaseous precursor filled vesicles, are useful as contrast agents for diagnostic imaging, including, for example, ultrasound (US) imaging, computed tomography (CT) imaging, including CT angiography (CTA) imaging, magnetic resonance (MR) imaging, magnetic resonance angiography (MRA), nuclear medicine, optical imaging and elastography.

In accordance with the present invention, there are provided methods of imaging one or more regions of a patient. The present invention also provides methods for diagnosing the presence or absence of diseased tissue in a patient. The methods of the present invention involve the administration of a contrast medium in the form, for example, of a lipid and/or vesicle composition, to a patient. The patient is scanned using diagnostic imaging including, for example ultrasound imaging, to obtain visible images of an internal region of a patient. The methods are especially useful in providing images of the heart region, the gastrointestinal region or the lymphatic system, but can also be employed more broadly to image other internal regions of the patient including, for example, the vasculature. The phrase "gastrointestinal region" or "gastrointestinal tract," as used herein, includes the region of a patient defined by the esophagus, stomach, small and large intestines and rectum. The present methods can also be used in connection with the delivery of a bioactive agent to an internal region of a patient.

If desired, the lipid and/or vesicle compositions described herein may further comprise a targeting agent to promote targeting of tissues and/or receptors in vivo including, for example, myocardial tissue. Suitable targeting agents, methods for their incorporation into lipid and/or vesicle compositions, and methods for the use of such targeted compositions, are described, for example, in copending U.S. application Ser. No. 08/640,464, filed May 1, 1996, now abandoned, the disclosures of which are hereby incorporated herein by reference, in their entirety.

As one skilled in the art would recognize, administration of the lipid and/or vesicle compositions described herein can be carried out in various fashions, including parenterally, orally, or intraperitoneally. Parenteral administration, which is preferred, includes administration by the following routes: intravenous; intramuscular; interstitially; intra-arterially; subcutaneous; intraocular; intrasynovial; transepithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration. The useful dosage to be administered and the particular mode of administration will vary depending upon the age, weight and the particular mammal and region thereof to be scanned, and the particular contrast agent employed. Typically, dosage is initiated at lower levels and increased until the desired contrast enhancement is achieved. Various combinations of the lipid compositions may be used to alter properties as desired, including viscosity, osmolarity or palatability. In carrying out the imaging methods of the present invention, the contrast medium can be used alone, or in combination with diagnostic, therapeutic or other agents. Such other agents include excipients such as flavoring or coloring materials. CT imaging techniques which are employed are conventional and are described, for example, in *Computed Body Tomography*, Lee, J. K. T., Sagel, S. S., and Stanley, R. J., eds., 1983, Ravens Press, New York, N.Y., especially the first two chapters thereof entitled "*Physical Principles and Instrumentation*", Ter-Pogossian, M. M., and "*Techniques*", Aronberg, D. J., the disclosures of which are incorporated by reference herein in their entirety.

In the case of diagnostic applications, such as ultrasound and CT, energy, such as ultrasonic energy, may be applied to at least a portion of the patient to image the target tissue. A visible image of an internal region of the patient may be then obtained, such that the presence or absence of diseased tissue can be ascertained. With respect to ultrasound, ultrasonic imaging techniques, including second harmonic imaging, and gated imaging, are well known in the art, and are described, for example, in Uhlendorf, "Physics of Ultrasound Contrast Imaging: Scattering in the Linear Range", *IEEE Transactions on Ultrasonics, Ferroelectrics, and Frequency Control*, Vol. 14(1), pp. 70–79 (1994) and Sutherland, et al., "Color Doppler Myocardial Imaging: A New Technique for the Assessment of Myocardial Function", *Journal of the American Society of Echocardiography*, Vol. 7(5), pp. 441–458 (1994), the disclosures of which are hereby incorporated herein by reference in their entirety.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency may be received, where x is the incidental frequency. This may serve to decrease the signal from the background material and enhance the signal from the transducer using the targeted contrast media of the present invention which may be targeted to the desired site. Other harmonics signals, such as odd harmonics signals, for example, 3x or 5x, may be similarly received using this method. Subharmonic signals, for example, x/2 and x/3, may also be received and processed so as to form an image.

In addition to the pulsed method, continuous wave ultrasound, for example, Power Doppler, may be applied. This may be particularly useful where rigid vesicles, for example, vesicles formulated from polymethyl methacrylate or cyanomethacrylate, are employed. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. It is contemplated that there may be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of the bioactive agents. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle species. In general, devices for therapeutic ultrasound employ from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may be pulsed also. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHz). In general, frequency for therapeutic ultrasound preferably ranges between about 0.75 and about 3 MHz, with from about 1 and about 2 MHz being more preferred. In addition, energy levels may vary from about 0.5 Watt (W) per square centimeter ($cm^2$) to about 5.0 $W/cm^2$, with energy levels of from about 0.5 to about 2.5 $W/cm^2$ being preferred. Energy levels for therapeutic ultrasound involving hyperthermia are generally from about 5 $W/cm^2$ to about 50 $W/cm^2$. For very small vesicles, for example, vesicles having a diameter of less than about 0.5 $\mu$m, higher frequencies of sound are generally preferred. This is because smaller vesicles may be capable of absorbing sonic energy more effectively at higher frequencies of sound. When very high frequencies are used, for example, greater than about 10 MHz, the sonic energy may penetrate fluids and tissues to a limited depth only. Thus, external application of the sonic energy may be suitable for skin and other superficial tissues. However, it is generally necessary for deep structures to focus the ultrasonic energy so that it is preferentially directed within a focal zone. Alternatively, the ultrasonic energy may be applied via interstitial probes, intravascular ultrasound catheters or endoluminal catheters. Such probes or catheters may be used, for example, in the esophagus for the diagnosis and/or treatment of esophageal carcinoma. In addition to the therapeutic uses discussed above, the compositions described herein can be employed in connection with esophageal carcinoma or in the coronary arteries for the treatment of atherosclerosis, as well as the therapeutic uses described, for example, in U.S. Pat. No. 5,149,319, the disclosures of which are hereby incorporated herein by reference, in their entirety.

A therapeutic ultrasound device may be used which employs two frequencies of ultrasound. The first frequency may be x, and the second frequency may be 2x. In preferred form, the device would be designed such that the focal zones of the first and second frequencies converge to a single focal zone. The focal zone of the device may then be directed to the compositions, for example, vesicle compositions, within the tissue in the region of interest. This ultrasound device may provide second harmonic therapy with simultaneous application of the x and 2x frequencies of ultrasound energy. It is contemplated that, in the case of ultrasound involving vesicles, this second harmonic therapy may provide improved rupturing of vesicles as compared to ultrasound energy involving a single frequency. Also, it is contemplated that the preferred frequency range may reside within the fundamental harmonic frequencies of the vesicles. Lower energy may also be used with this device. An ultrasound device which may be employed in connection with the aforementioned second harmonic therapy is described, for example, in Kawabata, K. et al., *Ultrasonics Sonochemistry*, Vol. 3, pp. 1–5 (1996), the disclosures of which are hereby incorporated herein by reference, in their entirety.

In the case of vesicle compositions formulated from lipids, the concentration of lipid required to form a desired stabilized vesicle level may vary depending upon the type of lipid used, and may be readily determined by routine experimentation. For example, in preferred embodiments, the concentration of 1,2-dipalmitoylphosphatidylcholine (DPPC) used to form stabilized vesicles according to the methods of the present invention may be from about 0.1 mg/mL to about 30 mg/mL of saline solution, more preferably from about 0.5 mg/mL to about 20 mg/mL of saline solution, and even more preferably from about 1 mg/mL to about 10 mg/mL of saline solution. The concentration of distearoylphosphatidylcholine (DSPC) used in preferred embodiments may be from about 0.1 mg/mL to about 30 mg/mL of saline solution, more preferably from about 0.5 mg/mL to about 20 mg/mL of saline solution, and even more preferably from about 1 mg/mL to about 10 mg/mL of saline solution. The amount of composition which is administered to a patient can vary. Typically, the IV dose may be less than about 10 mL for a 70 Kg patient, with lower doses being preferred.

The compositions described herein, and especially the vesicle compositions, are useful as contrast media in diagnostic imaging, and may also be suitable for use in all areas where diagnostic imaging is employed. However, the stabilized vesicles are particularly useful for perfusion imaging.

In accordance with the present invention, there are provided methods of imaging a patient generally, and/or in specifically diagnosing the presence of diseased tissue in a patient. The imaging process of the present invention may be carried out by administering a contrast agent to a patient, and then scanning the patient using, for example, ultrasound, computed tomography, and/or magnetic resonance imaging, to obtain visible images of an internal region of a patient and/or of any diseased tissue in that region. The term "region of a patient" refers to the whole patient or a particular area or portion of the patient. The contrast agent may be particularly useful in providing images of the gastrointestinal and cardiovascular regions, but can also be employed more broadly, such as in imaging the vasculature or in other ways as will be readily apparent to those skilled in the art. Cardiovascular region, as that phrase is used herein, denotes the region of the patient defined by the heart and the vasculature leading directly to and from the heart. The phrase vasculature, as used herein, denotes the blood vessels (including arteries, veins and the like) in the body or in an organ or part of the body. The patient can be any type of mammal, but most preferably is a human.

The present invention also provides methods of diagnosing the presence of diseased tissue in a patient. Diseased tissue includes, for example, endothelial tissue which results from vasculature that supports diseased tissue. As a result, the localization and visualization of endothelial tissue to a region of a patient which under normal circumstances is not associated with endothelial tissue provides an indication of diseased tissue in the region.

As noted above, administration of the compositions described herein may be carried out in various fashions, such as intravascularly, orally, rectally, and the like, using a variety of dosage forms. When the region to be scanned is the cardiovascular region, administration of the contrast medium is preferably carried out intravascularly. When the region to be scanned is the gastrointestinal region, administration of the contrast medium is preferably carried out orally or rectally. The useful dosage to be administered and the particular mode of administration will vary depending upon the age, weight and the particular mammal and region thereof to be scanned, and the particular contrast medium to be employed. Typically, dosage may be initiated at lower levels and increased until the desired contrast enhancement is achieved. Various combinations of the lipid and/or vesicle compositions may be used to modify the relaxation behavior of the medium or to alter properties such as the viscosity, osmolarity or palatability (in the case of orally administered materials). The present invention may be performed with ultrasound or computed tomography according to conventional methods known by skilled artisans. Ultrasound is a diagnostic imaging technique which is unlike nuclear medicine and X-rays since it does not expose the patient to the harmful effects of ionizing radiation. Moreover, unlike magnetic resonance imaging, ultrasound is relatively inexpensive and can be conducted as a portable examination. In using the ultrasound technique, sound is transmitted into a patient or animal via a transducer. When the sound waves propagate through the body, they encounter interfaces from tissues and fluids. Depending on the acoustic properties of the tissues and fluids in the body, the ultrasound sound waves are partially or wholly reflected or absorbed. When sound waves are reflected by an interface they are detected by the receiver in the transducer and processed to form an image. The acoustic properties of the tissues and fluids within the body determine the contrast which appears in the resultant image. Computed tomography imaging principles and techniques which are employed are conventional and are described, for example, in *Computed Body Tomography*, Lee, J. K. T., Sagel, S. S., and Stanley, R. J., eds., Ch. 1, pp. 1–7 (Raven Press, NY 1983). In carrying out the magnetic resonance imaging method of the present invention, the contrast agent can be used alone, or in combination with other diagnostic, therapeutic or other agents. Such other agents include excipients such as flavoring or coloring materials. The magnetic resonance imaging techniques which are employed are conventional and are described, for example, in D. M. Kean and M. A. Smith, *Magnetic Resonance Imaging. Principles and Applications*, (William and Wilkins, Baltimore 1986). Contemplated MRI techniques include, but are not limited to, nuclear magnetic resonance (NMR) and electronic spin resonance (ESR). The preferred imaging modality is NMR.

As noted above, the concentration of vesicles, especially the concentration of echogenic vesicles, referred to herein as "vesicle concentration," may be important with respect to the effectiveness of contrast agents based on vesicles. It is preferred that the vesicle compositions described herein have a vesicle concentration of at least about $1 \times 10^8$ vesicles/mL, as measured with a Model 770 AccuSizer (Particle Sizing Systems, Santa Barbara, Calif.). More preferably, the vesicle compositions have vesicle concentrations of at least about $1 \times 10^9$ vesicles/mL, with concentrations of about $1.5 \times 10^9$ vesicles/mL being even more preferred. In certain circumstances, compositions comprising vesicle concentrations of even more than $1.5 \times 10^9$ vesicles/mL may be desirable. However, these highly concentrated vesicle compositions may be difficult to administer, for example, in the case of administration by injection.

In connection with the diagnostic method aspects of the present invention, it has been surprisingly and unexpectedly found that the rate at which the lipid and/or vesicle compositions are administered to a patient may have a profound effect on the quality of the resulting diagnostic image. Specifically, it has been found that the occurrence of diagnostic artifacts in diagnostic images may be directly related to the rate at which the lipid and/or vesicle compositions are administered. Thus, as discussed above, the administration of a lipid and/or vesicle composition at too high a rate can result in an excess concentration of lipid and/or vesicle composition at the region of interest. In the case of ultrasound imaging, the application of energy (sound waves) can result in the reflection of an excess amount of sound energy, thereby resulting, for example, in shadowing in the resulting ultrasound image. Conversely, the administration of a lipid and/or vesicle composition at too low a rate can result in an insufficient concentration of lipid and/or vesicle composition at the region of interest. In the case of ultrasound imaging involving, for example, gas filled vesicles, the application of energy (sound waves) can result in too little sound energy being reflected, thereby resulting, for example, in inadequate contrast in the resulting ultrasound image.

In accordance with certain preferred embodiments of the present invention, the rate at which lipid and/or vesicle compositions which comprise a gas or gaseous precursor are administered may be determined and regulated as follows. The compositions may be administered to a patient at a dose of, for example, about 10 microliters ($\mu$L) of composition per kilogram (Kg) of patient body weight (10 $\mu$L/Kg). In certain preferred embodiments, the compositions may contain gas in a concentration which provides a dose of gas ranging from about $1\times10^{-4}$ to about $5\times10^{-3}$ cubic centimeters (cc) of gas per kilogram (Kg) of patient body weight, and all combinations and subcombinations of ranges therein. This gas dose may be employed to provide an administration rate of gas to a patient, referred to herein as the "gas administration rate."

The compositions may be administered over a period of time which can vary and depends upon a variety of factors including, for example, the volume of the composition being administered, the age and weight of the patient, the particular materials employed in the compositions, including, for example, lipids, polymers, proteins, vesicles, gases and/or gaseous precursors, the purpose for the administration (for example, diagnostic or therapeutic), the region of interest, the mode of administration, the size of the vesicles (in the case of vesicle compositions), and the like. An exemplary administration time for the compositions described above is about 5 seconds. Dividing the gas dose by this time period provides a gas administration rate which can be expressed as cc gas/Kg-sec. Thus, a gas dose of, for example, about $1\times10^{-4}$ cc gas/Kg and an administration time of 5 sec provides a gas administration rate of about $2\times10^{-5}$ cc gas/Kg-sec.

It is to be understood that the foregoing specific gas concentrations, composition doses, administration times and administration rates are for purposes of illustration only, and not for purposes of limitation.

In connection with preferred embodiments of the invention, the lipid and/or vesicle compositions may be administered to a patient to provide a gas administration rate which ranges from about $1\times10^{-7}$ to about $3\times10^{-3}$ cc gas/Kg-sec, and all combinations and subcombinations of ranges therein including, for example, from about $4\times10^{-7}$, $8\times10^{-7}$, $1\times10^{-6}$, $2\times10^{-6}$ or about $3\times10^{-6}$ to about $3\times10^{-3}$ cc gas/Kg-sec. More preferably, the lipid and/or vesicle compositions may be administered to provide a gas administration rate of from about $4\times10^{-6}$ to about $2\times10^{-3}$ cc gas/Kg-sec, with gas administration rates of from about $5\times10^{-6}$, $6\times10^{-6}$, $7\times10^{-6}$ or $8\times10^{-6}$ to about $2\times10^{-3}$ cc gas/Kg-sec being even more preferred. Still more preferably, the lipid and/or vesicle compositions may be administered to provide a gas administration rate of from about $9\times10^{-6}$ or $1\times10^{-5}$ to about $1\times10^{-3}$ cc gas/Kg-sec, with gas administration rates of from about $2\times10^{-5}$, $3\times10^{-5}$, $4\times10^{-5}$ or $5\times10^{-5}$ to about $1\times10^{-3}$ cc gas/Kg-sec being still more preferred. Yet more preferably, the lipid and/or vesicle compositions may be administered to a patient at a gas administration rate of from about $6\times10^{-5}$, $7\times10^{-5}$, $8\times10^{-5}$ or $9\times10^{-5}$ to less than about $1\times10^{-3}$ cc gas/Kg-sec, with gas administration rates of from about $1\times10^{-4}$ to about $9\times10^{-4}$ cc gas/Kg-sec being even still more preferred.

Gaseous precursors may be incorporated in the compositions described herein and may be, for example, liquids or solids, which are converted to a gas after administration (that is, in vivo), or prior to administration. As would be apparent to one of ordinary skill in the art, once armed with the present disclosure, concentrations of gaseous precursors may be employed in the compositions, and administration rates of compositions which contain gaseous precursors may be employed, which provide the foregoing gas administration rates upon conversion of the gaseous precursor into a gas.

As noted above, vesicle compositions represent a preferred form of the compositions employed in the methods of the present invention. Also as noted above, the concentration of vesicles in the vesicle compositions is preferably at least about $1.5\times10^8$ vesicles per mL of vesicle composition (vesicles/mL), more preferably at least about $1\times10^9$ vesicles/mL, and even more preferably at least about $1.5\times10^9$ vesicles/mL. This vesicle concentration may be employed to provide an administration rate of vesicles to a patient, referred to herein as the "vesicle administration rate." In this connection, the vesicle compositions may be administered to a patient at a dose of, for example, about 10 microliters ($\mu$L) of vesicle composition per kilogram (Kg) of patient body weight (10 $\mu$L/Kg). The product of the vesicle concentration (vesicles/mL) and the dose of the vesicle composition ($\mu$L/Kg) provides a vesicle dose which can be expressed as vesicles/Kg. Thus, the highly preferred vesicle concentration ($1.5\times10^9$ vesicles/mL) and the vesicle composition dose (10 $\mu$L/Kg) described above provides a vesicle dose of about $1.5\times10^7$ vesicles/Kg.

The vesicle compositions are generally administered over a period of time which may vary and depends upon a variety of factors including, for example, the volume of the vesicle composition being administered, the weight of the patient, the particular lipids, polymers, proteins, vesicles, gases or gaseous precursors employed in the composition, the purpose for the administration (for example, diagnostic or therapeutic), the region of interest, the mode of administration, the size of the vesicles, and the like. An exemplary administration time for the vesicle compositions is about 5 seconds. Dividing the vesicle dose by this time period provides an administration rate which may be expressed as vesicles/Kg-sec. Thus, the vesicle dose ($1.5\times10^7$ vesicles/Kg) and administration time (5 sec) described above provides a vesicle administration rate of about $3\times10^6$ vesicles/Kg-sec.

It is to be understood that the foregoing specific vesicle concentrations, composition doses, administration times and administration rates are for purposes of illustration only, and not for purposes of limitation.

It has been observed that diagnostic images obtained using methods which involve the administration of vesicle compositions at a rate of about $8\times10^6$ vesicles/Kg-sec or greater generally may contain substantial diagnostic artifacts. For example, in connection with ultrasound imaging, the administration of a vesicle composition at an administration rate of about $8\times10^6$ vesicles/Kg-sec or greater may result in significant shadowing in the resulting ultrasound image. In certain circumstances, the shadowing may be so severe as to prohibit visualization of the region of interest, thereby rendering the ultrasound image substantially unusable as a diagnostic tool. Delaying the application of energy or prolonging the period of time that energy is applied to the region of interest, in an effort to permit the concentration of lipid and/or vesicle composition at the region of interest to diminish, for example, by being carried away in the bloodstream, generally does not result in an improvement in the quality of the diagnostic image. Instead, it has been observed that as the diagnostic artifacts diminish, the contrast provided by the lipid and/or vesicle composition may diminish also.

In connection with preferred embodiments of the present invention, the vesicle compositions may be administered to a patient to provide a vesicle administration rate of less than about $8\times10^6$ vesicles/Kg-sec. More preferably, the vesicle compositions may be administered to a patient to provide a vesicle administration rate which ranges from about $1\times10^6$ to less than about $8\times10^6$ vesicles/Kg-sec, and all combinations and subcombinations of ranges therein, for example, from about $1\times10^6$ to about $7.5\times10^6$, about $7\times10^6$ or about $6.5 \times 10^6$ vesicles/Kg-sec. Even more preferably, the vesicle compositions may be administered to a patient to provide a vesicle administration rate of from about $1.5 \times 10^6$ to about $6 \times 10^6$ vesicles/Kg-sec, with vesicle administration rates of from about $2 \times 10^6$ to about $5.5 \times 10^6$ vesicles/Kg-sec being still more preferred. Yet more preferably, the vesicle compositions may be administered to provide a vesicle administration rate of from about $2.5 \times 10^6$ to about $5 \times 10^6$ vesicles/Kg-sec, with vesicle administration rates of from about $3 \times 10^6$ to about $4.5 \times 10^6$ vesicles/Kg-sec being even more preferred.

As would be apparent to one skilled in the art, based on the present disclosure, the rate at which the lipid and/or vesicle compositions are preferably administered can vary, depending, for example, on the lipids, polymers, proteins, vesicles, gases and/or gaseous precursors employed, the age and weight of the patient, the mode of administration, the size of the vesicles (in the case of vesicle compositions), and the like. Typically, administration may be carried out at lower rates and the rate can be increased until a desired effect is achieved.

In preferred embodiments of the present invention, the lipid and/or vesicle compositions may be administered by syringe, that is, by intravenous (IV) injection. Accordingly, the gas and/or vesicle administration rates provided herein generally correspond to injection rates. As would be apparent to one of ordinary skill in the art, once armed with the present disclosure, the location on the body of the patient at which the lipid and/or vesicle compositions are injected may vary and depends upon a variety of factors, including, for example, the particular lipid and/or vesicle composition employed, the contemplated application, such as diagnostic or therapeutic application, and the particular region of interest. For example, in the case of diagnostic ultrasound of myocardial tissue, the lipid and/or vesicle compositions may be injected intravenously, for example, in the arm of a patient.

The IV administration of the contrast agents described herein including, for example, the vesicle compositions, may involve administration via syringe. This may be achieved, for example, by an appropriate medical technician who handles the syringe or syringes manually. Alternatively, administration by syringe may be achieved mechanically, for example, via a mechanical injector, such as a mechanical injector which operates using pneumatic or hydraulic pressure. Suitable mechanical injectors which may be used in the methods of the present invention include a Syringe Pump Model 351, commercially available from Sage Instruments (a division of Orion Research Inc., Boston, Mass.), a MedRad™ power injector, commercially available from Medrad, Inc. (Pittsburgh, Pa.) or a Liebel Flarsheim, commercially available from Liebel Flarsheim Co. (Cincinnati, Ohio).

In connection with lipid and/or vesicle compositions which are administered via injection, it may be desirable, and sometimes preferable, to facilitate the movement through the circulating bloodstream of the injected composition. As would be apparent to one of ordinary skill in the art, once armed with the present disclosure, administration by injection generally involves injection of the compositions into a blood vessel. Also as known to the skilled artisan, the blood flow in many blood vessels, and especially smaller blood vessels, may be limited. Due to this limited blood flow, the injected lipid and/or vesicle compositions may pool or accumulate at or near the site of injection. To promote the transport of the lipid and/or vesicle composition from the injection site into the bloodstream and, thereafter, to the region of interest, a flush may be administered. The flush may act, generally by mechanical action, to "push" or "wash" the injected compositions into the bloodstream. Thus, in embodiments which may involve, for example, diagnostic ultrasound of myocardial tissue with a contrast agent that comprises a lipid and/or vesicle composition, a flush may be administered after injection of the lipid and/or vesicle composition to facilitate its movement through the circulatory system and delivery to the region of interest, for example, the heart region.

In embodiments which involve the flush of lipid and/or vesicle compositions, it has been surprisingly and unexpectedly found that, as with the administration rates discussed hereinbefore, the rate at which the lipid and/or vesicle compositions are flushed may have a profound effect on the quality of the resulting diagnostic image. For example, flushing at too high a rate may result in an excess concentration of lipid and/or vesicle composition at the region of interest. Thus, in the case of diagnostic imaging, such as ultrasound, involving, for example, gas filled vesicles, the application of energy, for example, sound waves, may result in the reflection of excess energy from the vesicles. As discussed in detail above, this may cause diagnostic artifacts, for example, shadowing, in the resulting image. Conversely, flushing at too low a rate may result in an insufficient concentration of lipid and/or vesicle composition at the region of interest. It is contemplated that in this case, the lipid and/or vesicle compositions may become highly diluted in the bloodstream. In the case of diagnostic imaging, such as ultrasound, involving, for example, gas filled vesicles, the application of energy, for example, sound waves, may result in the reflection of an insufficient quantity of energy from the vesicles. This may cause diagnostic artifacts, for example, lightening and/or brightening, which are associated with insufficient contrast. As would be apparent to one skilled in the art, based on the present disclosure, the rate at which the lipid and/or vesicle compositions are preferably flushed may vary, depending, for example, on the lipids, vesicles, polymers, proteins, gases and/or gaseous precursors employed, the age and weight of the patient, the mode of administration, the size of the vesicles (in the case of vesicle compositions), and the like.

In accordance with the present invention, the rate at which the lipid compositions may be flushed can be determined as follows. After administration of a lipid and/or vesicle composition, a flush may be administered which can be expressed as the volume of flush (mL) that is administered per unit time (sec). An exemplary flush for the dosages described above can involve a volume of about 5 mL which may be administered over a period of about 10 seconds, providing a flush of about 0.5 mL/sec.

It is to be understood that the foregoing specific flush rate is for purposes of illustration only, and not for purposes of limitation.

In embodiments of the present invention which involve flushing, it has been observed that diagnostic images obtained using methods which involve flushing at a rate of about 2.5 mL/sec or greater may contain substantial diagnostic artifacts. In certain circumstances, the shadowing may be so severe as to prohibit visualization of the region of interest, thereby rendering the ultrasound image substantially unusable as a diagnostic tool. Thus, the flush may preferably be administered at rates of less than about 2.5 mL/sec, for example, from about 0.01 to about 2.4 mL/sec, and all combinations and subcombinations of ranges therein. More preferably, the flush may be administered at a rate of from about 0.02 to about 2.3 mL/sec, with flush rates of from about 0.03 to about 2.2 mL/sec, about 0.04 to about 2.1 mL/sec, about 0.05 to about 2 mL/sec, about 0.06 to about 1.9 mL/sec, about 0.07 to about 1.8 mL/sec, about 0.08 to about 1.7 mL/sec, about 0.09 to about 1.6 mL/sec, or about 0.1 to about 1.5 mL/sec being even more preferred. Still more preferably, the flush may be administered at a rate of from about 0.2 to about 1.4 mL/sec, with flush rates of from about 0.3 to about 1.3 mL/sec, about 0.4 to about 1.2 mL/sec or about 0.5 to about 1.1 mL/sec being yet more preferred.

As would be apparent to one of ordinary skill in the art, once armed with the present disclosure, the gas and/or vesicle administration rates and flush rates described above may be used in connection with the administration to a patient of lipid and/or vesicle formulations. The particular administration and/or flush rates employed with lipid and/or vesicle formulations may vary and depends on a variety of factors, including, for example, the specific bioactive agents and lipids, vesicles, proteins and/or polymers involved, the particular disorder being treated, and the like. Typically, a lower flush rate may be employed initially, and then increased until a desired diagnostic effect is achieved.

As with the IV administration of the contrast agents, the administration of the flush may be achieved via syringe. This may involve, for example, manual manipulation of a syringe by an appropriate medical technician. Also, as noted above in connection with the administration of the vesicle compositions, the administration of the flush may be done mechanically, for example, via a mechanical syringe pump, including mechanical pumps which operate using hydraulic and/or pneumatic power, such as, for example, a Syringe Pump Model 351 (Sage Instruments, a division of Orion Research Inc., Boston, Mass.), or a mechanical power injector, such as a MedRadTm Power Injector (Medrad, Inc., Pittsburgh, Pa.) or a Liebel Flarsheim (Liebel Flarsheim Co., Cincinnati, Ohio).

Referring to the drawings, wherein like numerals refer to like elements throughout the several views, there is shown in FIG. 1 a schematic representation of a system 10 including an apparatus 12 for administering a contrast agent to a patient in accordance with an embodiment of the present invention. The apparatus 12 includes a first vessel which, in FIG. 1, is depicted as a syringe 14 consisting of a barrel 16 and a plunger 18 which is slidably engaged with the barrel 16. A contrast agent 20, such as, for example, a vesicle composition as described hereinabove, is contained in the syringe 14.

The apparatus 12 further comprises a second vessel which, in accordance with the presently preferred embodiment, comprises a mechanical injector 22. A device which is particularly suitable for use as the mechanical injector 22 is a MedRad™ Power Injector (Medrad, Inc., Pittsburgh, Pa.). The mechanical injector 22 preferably contains a flush agent 24, such as saline. As shown in FIG. 1, the syringe 14 and the mechanical injector 22 are in flow communication with each other via a conduit 26. The conduit 26 is preferably adapted to administer the contrast agent 20 and/or flush agent 24 to a patient 28 (shown schematically). The conduit 26 preferably comprises tubing 30, which may comprise any suitable sterile plastic tubing, and a needle 32. Means are provided for connecting the syringe 14 and the mechanical injector 22 with the tubing 30 which places the syringe 14 and the mechanical injector 22 in flow communication with each other. In accordance with the presently preferred embodiment, the flow communication means comprises a 3-way stopcock 34 which is engaged to the needle 32 and the tubing 30 and is located below the syringe 14. The stopcock 34 comprises a housing 36 and a valve 38. As shown in FIG. 1, a nozzle 40 is also provided on the mechanical injector 22 to which the tubing 30 is connected.

Also provided in the apparatus 12 is a control means 42, shown in schematic form, for controlling the mechanical injector 22. The control means 42 controls the amount of power supplied to the mechanical injector 22 and permits regulation of the rate at which the mechanical injector 22 operates and, thereby, the rate at which the flush agent 24 is ejected from the mechanical injector 22.

Figure 2:
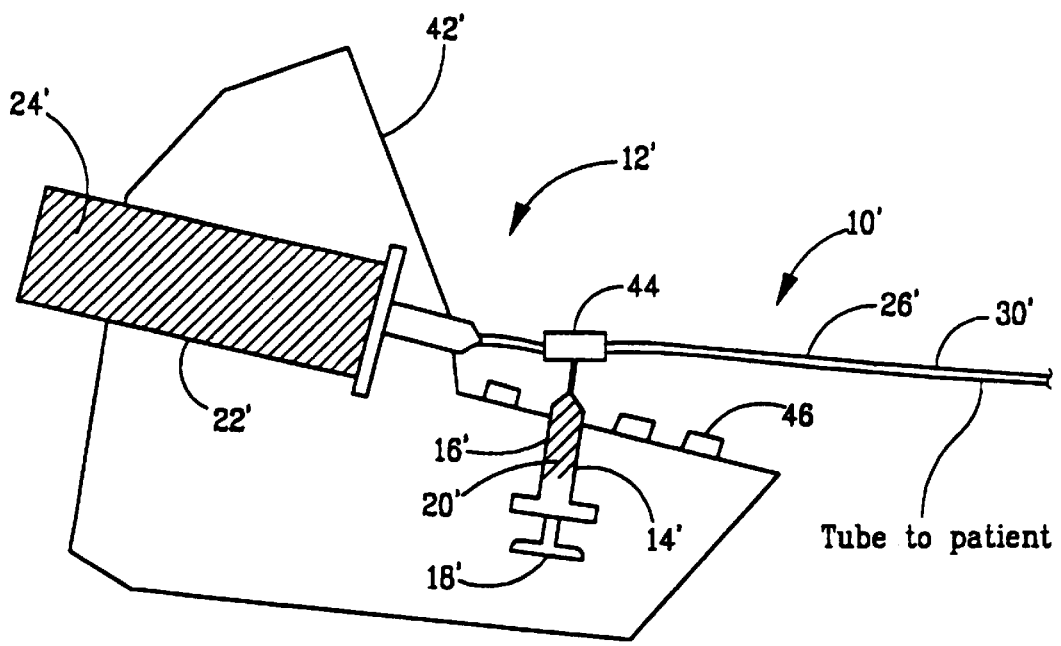
FIG. 2 is a partial schematic representation of a system including an apparatus for administering a contrast agent to a patient according to an alternate embodiment of the present invetion.

In accordance with an alternate embodiment of the present invention, there is shown in FIG. 2 a schematic representation of a system 10' including an apparatus 12' for administering a contrast agent to a patient. The apparatus 12' is similar to the apparatus described above in connection with FIG. 1, and includes a first vessel which preferably comprises a syringe 14' comprising a barrel 16' and a plunger 18'. A contrast agent 20' is preferably contained in the barrel 16'. There is also provided in the embodiment depicted in FIG. 2 a second vessel which, in accordance with the presently preferred embodiment, comprises a mechanical injector 22'. As with the embodiment discussed above, a device which is particularly suitable for use as the mechanical injector 22' is a MedRad™ Power Injector (Medrad, Inc., Pittsburgh, Pa.). The mechanical injector 22' also preferably contains a flush agent 24', such as saline. The syringe 14' and the mechanical injector 22' are preferably in flow communication with each other via a conduit 26'. The conduit 26' is preferably adapted to administer the contrast agent 20' and/or flush agent 24' to a patient (not shown). The conduit 26' preferably comprises tubing 30', which may comprise any suitable sterile plastic tubing, and a needle (not shown) for insertion into the patient. Means are provided for connecting the syringe 14' and the mechanical injector 22' with the tubing 30' which places the syringe 14' and the mechanical injector 22' in flow communication with each other. In accordance with the presently preferred embodiment, the flow communication means comprises a port 44 which is engaged to the syringe 14' and the tubing 30' and is located above the syringe 14'.

The apparatus 12' further comprises a control means 42', which includes a display panel 46, for controlling the mechanical injector 22'.

There is provided herein a description of methods for the administration of a contrast agent, for example, a vesicle composition comprising lipid-, polymer- and/or protein-based vesicles, which may be performed utilizing the systems depicted in the figures. With particular reference to FIG. 1, the valve 38 in the 3-way stopcock 32 is preferably turned to the "off" position with respect to the contrast agent 20 and the flush agent 24. The needle 32 is inserted into an appropriate blood vessel in the patient 28, such as, for example, the antecubital fossa vein. The valve 38 is turned to the "on" position with respect to the contrast agent 20 and the plunger 18 is depressed. The contrast agent is ejected from the syringe 14 and introduced into the patient 28. Preferably, the plunger 18 is depressed at a rate to provide, in the case of a contrast agent 20 which comprises a vesicle composition, a vesicle administration rate of less than about $8 \times 10^6$ vesicles/Kg-sec, with an administration rate of from about $1 \times 10^6$ to less than about $8 \times 10^6$ vesicles/Kg-sec being more preferred. It is also preferred that the rate at which the plunger 18 is depressed provides, in the case of contrast agents which comprise a gas or gaseous precursor, a gas administration rate of from about $1 \times 10^{-7}$ to about $3 \times 10^{-3}$ cc gas/Kg-sec.

If desired, the needle 32 may be removed from the patient's arm without further administration of contrast agent and/or flush agent. Diagnostic imaging may also be performed after administration of the contrast agent 20 to obtain a visible image of the region of interest. Alternatively, and in accordance with the presently preferred embodiment, a flush agent may be administered after administration of the contrast agent 20. In this case, the valve 38 is turned to the "on" position with respect to the flush agent 24. The control means 42 may then be operated to drive the mechanical injector 22. The flush agent 24 is ejected from the mechanical injector 22 and is administered to the patient via the conduit 26. Preferably, the mechanical injector 22 is operated, for example, via the control means 42, to provide a flush injection rate of from about 0.05 to about 2 mL/sec. The rate at which the mechanical injector 22 is operated may be varied at any time during the ejection of the flush agent 24, as desired. Thus, the rate at which the flush agent 24 is administered may vary and may differ from, or be about the same as, the rate at which the contrast agent 20 is administered. After injection of the flush agent 24, diagnostic imaging may be performed to obtain a visible image of the region of interest.

In accordance with the embodiment depicted in FIG. 2, the system may be utilized as described hereinafter. The needle (not shown) is inserted into an appropriate blood vessel in the patient (not shown), such as the antecubital fossa vein. The plunger 18' is depressed, causing the contrast agent 20' to be ejected from the syringe 14' into the port 44. The contrast agent 20' will generally pool or collect in the port 44, and may also become distributed throughout the tubing 30'. Since in the present embodiment the contrast agent 20' is not ejected into the patient from the syringe 14', the rate at which the plunger 18' is depressed will generally not affect the quality of the image obtained during the subsequent diagnostic imaging.

The flush agent 24' is desirably administered after ejection of the contrast agent 20'. This generally involves operation of the control means 42' to drive the mechanical injector 22'. As with the embodiment discussed above, the control means 42' controls the amount of power supplied to the mechanical injector 22' and permits regulation of the rate at which the mechanical injector 22' operates and, thereby, the rate at which the flush agent 24' is ejected from the mechanical injector 22'. The flush agent 24' is ejected from the mechanical injector 22' and into and through the tubing 30' and the port 44. The flush agent 24' serves to push or drive the contrast agent 20 from its location in the port 44 and/or the tubing 30', throughout the length of the tubing 30', and into the patient. Preferably, the mechanical injector 22' is operated, for example, via the control means 42', to provide a flush injection rate of from about 0.05 to about 2 mL/sec. The flush may be stopped after contrast agent 20' has been administered to the patient. Alternatively, the flush may be continued so that the flush agent 24' is also injected into the patient. The rate at which the mechanical injector 22' is operated may be varied at any time during the ejection of the flush agent 24', as desired.

After injection into the patient of the contrast agent 20' (and optional injection into the patient of the flush agent 24'), diagnostic imaging may be performed to obtain a visible image of the region of interest.

The echogenicity of vesicles, and especially, gas filled vesicles, and the ability to rupture vesicles at the peak resonant frequency using ultrasound, permits the controlled delivery of bioactive agents to an internal region of a patient. Specifically, the vesicles may be monitored subsequent to their administration to a patient to determine the rate at which the vesicles arrive, for example, to a desired region. Furthermore, the vesicles may be ruptured using ultrasound to release the bioactive agent in the region.

The invention is further described in the following examples. Examples 1 to 6 are actual examples, while Examples 7 to 11 are prophetic examples. These examples are for illustrative purposes only, and are not to be construed as limiting the appended claims.

EXAMPLE 1

This example describes the preparation of a lipid composition for use in the methods of the present invention. "DPPC" refers to dipalmitoylphosphatidylcholine; "DPPE" refers to dipalmitoylphosphatidylethanolamine; and "DPPA" refers to dipalmitolylphosphatidic acid. "PEG5000" refers to poly(ethylene glycol) polymer having a molecular weight of about 5000. "DPPE-PEG5000" refers to DPPE which is covalently bound to PEG5000, wherein the DPPE and PEG5000 are present in a weight ratio of about 20:80. "PFP" refers to perfluoropropane gas.

To a solution of saline, propylene glycol and glycerol (8:1:1) were added DPPC, DPPE-PEG5000 and DPPA in a molar ratio of 82:8:10. The resulting mixture was heated to about 45° C. and filtered (0.22 $\mu$m). The filtered mixture was placed in a vial and allowed to cool to room temperature. The vial was placed under vacuum to evacuate any gas, after which the vial was pressurized with PFP. The vial was then sealed, placed on a shaker and agitated at room temperature to provide a solution of PFP-filled vesicles having a mean diameter of about 2.5 $\mu$m. The concentration of vesicles in the solution was about $1.5 \times 10^9$ vesicles/mL.

The following examples are directed to methods for using the gas filled vesicles prepared in Example 1.

EXAMPLE 2

The solution of PFP-vesicles of Example 1 was administered intravenously (IV) to a healthy human subject at a dose of about 10 $\mu$L per Kg of body weight, providing a vesicle dose of about $1.5 \times 10^7$ vesicles/Kg. The site of administration was in the antecubital fossa region in the patient's arm. The time period for injecting the solution of PFP-filled vesicles was 2 seconds, providing a vesicle injection rate of $7.5 \times 10^6$ vesicles/Kg-sec. After injection, a saline flush (5 mL) was administered in the same injection site. The time period for injecting the saline flush was 2 seconds, providing a flush rate of 2.5 mL/sec. Transducers (2.5, 3.5 and 5.0 MHz) were used to image the heart region in both short-axis and long-axis views. Image detection was via grey scale imaging. After injection of the saline flush, the ultrasound image rapidly darkened until the heart was not visible due to severe shadowing. This severe shadowing lasted for a period of time of about 30 seconds to about 1 minute. Upon dissipation of the shadowing, the ultrasound image revealed only transient contrast enhancement of the myocardial tissues.

EXAMPLE 3

Example 2 was repeated, except that (A) the time period for injecting the solution of PFP-filled vesicles was increased to from about 5 to about 10 seconds, providing a vesicle injection rate of from about $1.5 \times 10^6$ to about $3.0 \times 10^6$ vesicles/Kg-sec; and (B) the time period for injecting the saline flush was increased to from about 10 to about 15 seconds, providing a flush rate of from about 0.33 to about 0.5 mL/sec. After injection of the saline flush, shadowing was substantially completely eliminated, and the contrast of the myocardial tissue was very robust and long-lasting.

EXAMPLE 4

Example 3 was repeated, except that the time period for injecting the solution of PFP-filled vesicles was increased to about 15 seconds. This provided a vesicle injection rate of about $1.0 \times 10^6$ vesicles/Kg-sec. The flush rate remained about the same as that in Example 3. Although no shadowing was observed after injection of the saline flush, the contrast of the myocardial tissue was less robust.

EXAMPLE 5

Example 2 was repeated, except that (A) the dose of the solution of PFP-filled vesicles was increased to 15 $\mu$L/Kg, providing a vesicle dose of about $2.25 \times 10^7$ vesicles/Kg and a vesicle injection rate of from about $2.25 \times 10^6$ to about $4.5 \times 10^6$ vesicles/Kg-sec; and (B) the time period for injecting the flush was increased to from about 15 to about 20 seconds, providing a flush injection rate of from about 0.25 to about 0.33 mL/sec. After injection of the saline flush, shadowing was substantially completely eliminated, and the contrast of the myocardial tissue was very robust and long-lasting.

EXAMPLE 6

Example 5 was repeated, except that (A) the dose of the solution of PFP-filled vesicles was increased to 30 $\mu$L/Kg, providing a vesicle dose of about $4.5 \times 10^7$ vesicles/Kg and a vesicle injection rate of from about $4.5 \times 10^6$ to about $9.0 \times 10^6$ vesicles/Kg-sec; and (B) the time period for injecting the flush was increased to from about 30 to about 40 seconds, providing a flush injection rate of from about 0.125 to about 0.167 mL/sec. The quality of the contrast was substantially similar to that obtained in Example 5, but lasted for an even longer period of time.

EXAMPLE 7

The PFP-filled vesicles prepared in Example 1 are administered to a patient to provide a gas administration rate of about $5 \times 10^{-4}$ cc gas/Kg-sec. Imaging of the heart region is then carried out as described in the previous examples. Shadowing is substantially completely eliminated, and the contrast of the myocardial tissue is very robust and long-lasting.

EXAMPLE 8

Example 7 is repeated, except that a saline flush is also employed at a flush rate of about 0.5 mL/sec.

EXAMPLE 9

Example 5 is repeated except that (A) the dose of the solution of PFP-filled vesicles is increased to 100 $\mu$L/Kg, providing a vesicle dose of about $1.5 \times 10^8$ vesicles/Kg; (B) the time period for injecting the solution of PFP-filled vesicles is increased to about 50 seconds, providing a vesicle injection rate of about $3.0 \times 10^6$ vesicles/Kg-sec; (C) the volume of flush is increased to about 10 mL; and (D) the time period for injecting the flush is increased to from about 5 to about 10 minutes, providing a flush injection rate of from about 0.0167 to about 0.03 mL/sec. After injection of the saline flush, shadowing is perceived to be substantially completely eliminated, and the contrast of the myocardial tissue is perceived to be very robust and long-lasting.

EXAMPLE 10

Example 2 is repeated, except that (A) a system of the type depicted in FIG. 1 is employed, wherein the flush is delivered by a MedRad™ Power Injector (Medrad, Inc., Pittsburgh, Pa.); (B) the saline flush volume is increased to about 20 mL; and (C) the time period for injecting the flush is increased to about 50 seconds to provide a flush rate of 2.5 mL/sec. Contrast of the myocardial tissue is very robust and long-lasting.

EXAMPLE 11

Example 11 is repeated, except that (A) a system of the type depicted in FIG. 2 is employed, wherein a MedRad™ Power Injector (Medrad, Inc., Pittsburgh, Pa.) is employed to eject a flush agent which pushes the contrast agent from the apparatus into the patient; and (B) the saline flush volume is increased to about 25 mL. Contrast of the myocardial tissue is very robust and long-lasting.

The disclosures of each patent, patent application and publication cited or described in this document are hereby incorporated by reference, in their entirety.

Various modifications of the invention, in addition to those described herein, will be apparent to those skilled in the art from the foregoing description. Such modifications are also intended to fall within the scope of the appended claims.

What is claimed is:

1. A method for providing an image of an internal region of a patient comprising (i) administering to the patient a vesicle composition comprising, in an aqueous carrier, a gas or gaseous precursor and vesicles comprising lipids, and (ii) scanning the patient using ultrasound imaging to obtain a visible image of the region, wherein said vesicle composition is administered to the patient at a rate which substantially eliminates ultrasound artifacts in the image, wherein said administration rate comprises continuos infusion.

2. A method according to claim I wherein said vesicles comprise lipids.

3. A method according to claim 2 wherein said vesicle composition comprises vesicles selected from the group consisting of micelles and liposomes.

4. A method according to claim 2 wherein said lipids comprise phospholipids.

5. A method according to claim 4 wherein said phospholipids are selected from the group consisting of phosphatidylcholine, phosphatidylethanolamine and phosphatidic acid.

6. A method according to claim 5 wherein said phosphatidylcholine is selected from the group consisting of dioleoylphosphatidylcholine, dimyristoylphosphatidylcholine, dipalmitoylphosphatidylcholine and distearoylphosphatidycholine.

7. A method according to claim 6 wherein said phosphatidylcholine comprises dipalmitoylphosphatidylcholine.

8. A method according to claim 5 wherein said phosphatidylethanolamine is selected from the group consisting of dipalmitoylphosphatidylethanolamine, dioleoylphosphatidylethanolamine, N-succinyldioleoylphosphatidylethanolamine and 1-hexadecyl-2-palmitoylglycerophosphoethanolamine.

9. A method according to claim 8 wherein said phosphatidylethanolamine comprises dipalmitoylphosphatidylethanolamine.

10. A method according to claim 5 wherein said phosphatidic acid comprises dipalmitolylphosphatidic acid.

11. A method according to claim 2 wherein said lipid further comprises a polymer.

12. A contrast agent according to claim 11 wherein said polymer comprises a hydrophilic polymer.

13. A method according to claim 11 wherein said hydrophilic polymer comprises polyethylene glycol.

14. A method according to claim 1 wherein said gas comprises a fluorinated gas.

15. A method according to claim 14 wherein said fluorinated gas is selected from the group consisting of a perfluorocarbon, sulfur hexafluoride and heptafluoropropane.

16. A method according to claim 15 wherein said fluorinated gas comprises a perfluorocarbon.

17. A method according to claim 16 wherein said perfluorocarbon gas is selected from the group consisting of perfluoromethane, perfluoroethane, perfluoropropane, perfluorobutane and perfluorocyclobutane.

18. A method according to claim 1 wherein said gaseous precursor has a boiling point of greater than about 37° C.

19. A method according to claim 18 wherein said gaseous precursor comprises a fluorinated compound.

20. A method according to claim 19 wherein said fluorinated compound comprises a perfluorocarbon.

21. A method according to claim 20 wherein said perfluorocarbon is selected from the group consisting of perfluoropentane and perfluorohexane.

22. A method according to claim 1 wherein said internal region comprises the heart region.

23. A method according to claim 1 wherein said vesicle composition is administered to the patient at a rate of from about $1 \times 10^6$ to less than about $8 \times 10^6$ vesicles/Kg-sec.

24. A method according to claim 23 wherein said vesicle composition is administered at a rate of from about $1 \times 10^6$ to about $7 \times 10^6$ vesicles/Kg-sec.

25. A method according to claim 24 wherein said vesicle composition is administered at a rate of from about $1.5 \times 10^6$ to about $6 \times 10^6$ vesicles/Kg-sec.

26. A method according to claim 25 wherein said vesicle composition is administered at a rate of from about $2 \times 10^6$ to about $5.5 \times 10^6$ vesicles/Kg-sec.

27. A method according to claim 26 wherein said vesicle composition is administered at a rate of from about $2.5 \times 10^6$ to about $5 \times 10^6$ vesicles/Kg-sec.

28. A method according to claim 27 wherein said vesicle composition is administered at a rate of from about $3 \times 10^6$ to about $4.5 \times 10^6$ vesicles/Kg-sec.

29. A method according to claim 1 wherein said vesicle composition is administered to the patient at a rate of from about $1 \times 10^{-7}$ to about $3 \times 10^{-3}$ cc gas/Kg-sec.

30. A method according to claim 29 wherein said vesicle composition is administered at a rate of from about $3 \times 10^{-6}$ to about $3 \times 10^{-3}$ cc gas/Kg-sec.

31. A method according to claim 30 wherein said vesicle composition is administered at a rate of from about $4 \times 10^{-6}$ to about $2 \times 10^{-3}$ cc gas/Kg-sec.

32. A method according to claim 31 wherein said vesicle composition is administered at a rate of from about $8 \times 10^6$ to about $2 \times 10^{-3}$ cc gas/Kg-sec.

33. A method according to claim 32 wherein said vesicle composition is administered at a rate of from about $1 \times 10^{-5}$ to about $1 \times 10^{-3}$ cc gas/Kg-sec.

34. A method according to claim 33 wherein said vesicle composition is administered at a rate of from about $4 \times 10^{-5}$ to about $1 \times 10^{-3}$ cc gas/Kg-sec.

35. A method according to claim 33 wherein said vesicle composition is administered at a rate of from about $8 \times 10^{-5}$ to less than about $1 \times 10^{-3}$ CC gas/Kg-sec.

36. A method according to claim 35 wherein said vesicle composition is administered at a rate of from about $1 \times 10^{-4}$ to about $9 \times 10^{-4}$ cc gas/Kg-sec.

37. A method for providing an image of an internal region of a patient comprising (i) administering to the patient a lipid composition comprising, in an aqueous carrier, a lipid and a gas or gaseous precursor, and (ii) scanning the patient using ultrasound imaging to obtain a visible image of the region, wherein said lipid composition is administered to the patient at a rate which substantially eliminates ultrasound artifacts in the image, wherein said administration rate comprises continuous infusion.

38. A method according to claim 37 wherein said lipid comprises a phospholipid.

39. A method according to claim 38 wherein said phospholipid is selected from the group consisting of phosphatidylcholine, phosphatidylethanolamine and phosphatidic acid.

40. A method according to claim 39 wherein said lipid composition comprises a vesicle composition.

41. A method according to claim 40 wherein said vesicle composition comprises vesicles selected from the group consisting of micelles and liposomes.

42. A method according to claim 37 wherein said lipid composition is administered to the patient at a rate of from about $1 \times 10^{-7}$ to about $3 \times 10^{-3}$ cc gas/Kg-sec.

43. A method according to claim 42 wherein said lipid composition is administered at a rate of from about $3 \times 10^{-6}$ to about $3 \times 10^{-3}$ cc gas/Kg-sec.

44. A method according to claim 43 wherein said lipid composition is administered at a rate of from about $4 \times 10^{-6}$ to about $2 \times 10^{-3}$ cc gas/Kg-sec.

45. A method according to claim 44 wherein said lipid composition is administered at a rate of from about $8 \times 10^{-6}$ to about $2 \times 10^{-3}$ cc gas/Kg-sec.

46. A method according to claim 45 wherein said lipid composition is administered at a rate of from about $1 \times 10^{-5}$ to about $1 \times 10^{-3}$ cc gas/Kg-sec.

47. A method according to claim 46 wherein said lipid composition is administered at a rate of from about $4 \times 10^{-5}$ to about $1 \times 10^{-3}$ cc gas/Kg-sec.

48. A method according to claim 47 wherein said lipid composition is administered at a rate of from about $8 \times 10^{-5}$ to less than about $1 \times 10^{-3}$ cc gas/Kg-sec.

49. A method according to claim 48 wherein said lipid composition is administered at a rate of from about $1 \times 10^{-4}$ to about $9 \times 10^{-4}$ cc gas/Kg-sec.

50. A method for providing an image of an internal region of a patient comprising (i) administering to the patient a vesicle composition comprising, in an aqueous carrier, a gas or gaseous precursor and vesicles comprising lipids, (ii) flushing said composition, and (iii) scanning the patient using ultrasound imaging to obtain a visible image of the region, wherein said composition is flushed at a rate which substantially eliminates ultrasound artifacts in the image, wherein said flushing rate comprises continuous infusion.

51. A method accroding to claim 50 wherien said vesicles comprise lipids.

52. A method according to claim 50 wherein said lipids comprise phospholipids.

53. A method according to claim 52 wherein said phospholipids are selected from the group consisting of phosphatidylcholine, phosphatidylethanolamine and phosphatidic acid.

54. A method according to claim 53 wherein said phosphatidylcholine is selected from the group consisting of dioleoylphosphatidylcholine, dimyristoylphosphatidylcholine, dipalmitoylphosphatidylcholine and distearoylphosphatidylcholine.

55. A method according to claim 54 wherein said phosphatidylcholine comprises dipalmitoylphosphatidylcholine.

56. A method according to claim 53 wherein said phosphatidylethanolamine is selected from the group consisting of dipalmitoylphosphatidylethanolamine, dioleoylphosphatidylethanolamine, N-succinyldioleoylphosphatidylethanolamine and 1-hexadecyl-2-palmitoylglycerophosphoethanolamine.

57. A method according to claim 56 wherein said phosphatidylethanolamine comprises dipalmitoylphosphatidylethanolamine.

58. A method according to claim 53 wherein said phosphatidic acid comprises dipalmitolylphosphatidic acid.

59. A method according to claim 50 wherein said vesicle composition is flushed with a saline solution.

60. A method according to claim 50 wherein said gas comprises a fluorinated gas.

61. A method according to claim 60 wherein said fluorinated gas is elected from the group consisting of a perfluorocarbon gas, sulfur hexafluoride and eptafluoropropane.

62. A method according to claim 61 wherein said fluorinated gas comprises a perfluorocarbon.

63. A method according to claim 62 wherein said perfluorocarbon gas is selected from the group consisting of perfluoromethane, perfluoroethane, perfluoropropane, perfluorobutane and perfluorocyclobutane.

64. A method according to claim 50 wherein said gaseous precursor has a boiling point of greater than about 37° C.

65. A method according to claim 64 wherein said gaseous precursor comprises a fluorinated compound.

66. A method according to claim 65 wherein said fluorinated compound comprises a perfluorocarbon.

67. A method according to claim 66 wherein said perfluorocarbon is selected from the group consisting of perfluoropentane and perfluorohexane.

68. A method according to claim 61 wherein said vesicle composition comprises vesicles selected from the group consisting of micelles and liposomes.

69. A method according to claim 50 wherein said internal region omprises the heart region.

70. A method according to claim 50 wherein said vesicle composition is flushed at a rate of from about 0.01 to about 2.4 mL/sec.

71. A method according to claim 70 wherein said vesicle composition is flushed at a rate of from about 0.05 to about 2 mL/sec.

72. A method according to claims 71 wherein said vesicle composition is flushed at a rate of from about 0.07 to about 1.8 mL/sec.

73. A method according to claim 72 wherein said vesicle composition is flushed at a rate of from about 0.09 to about 1.6 mL/sec.

74. A method according to claim 73 wherein said vesicle composition is flushed at a rate of from about 0.1 to about 1.5 mL/sec.

75. A method according to claim 74 wherein said vesicle composition is flushed at a rate of from about 0.3 to about 1.3 mL/sec.

76. A method for providing an image of an internal region of a patient comprising (i) administering to the patient a lipid composition comprising, in an aqueous carrier, a lipid and a gas or gaseous precursor, (ii) flushing said composition, and (iii) scanning the patient using ultrasound imaging to obtain a visible image of the region, wherein said composition is flushed at a rate which substantially eliminates ultrasound artifacts in the image, wherein said flushing rate comprises contiguous infusion.

77. A method according to claim 76 wherein said lipid comprises a phospholipid.

78. A method according to claim 77 wherein said phospholipid is selected from the group consisting of phosphatidylcholine, phosphatidylethanolamine and phosphatidic acid.

79. A method according to claim 78 wherein said lipid composition comprises a vesicle composition.

80. A method according to claim 76 wherein said vesicle composition comprises vesicles selected from the group consisting of micelles and liposomes.

81. A method according to claim 76 wherein said internal region comprises the heart region.

82. A method according to claim 76 wherein said composition is flushed at a rate of from about 0.01 to about 2.4 mL/sec.

83. A method according to claim 82 wherein said lipid composition is flushed at a rate of from about 0.05 to about 2 mL/sec.

84. A method according to claim 83 wherein said lipid composition is flushed at a rate of from about 0.07 to about 1.8 mL/sec.

85. A method according to claim 84 wherein said lipid composition is flushed at a rate of from about 0.09 to about 1.6 mL/sec.

86. A method according to claim 85 wherein said lipid composition is flushed at a rate of from about 0.1 to about 1.5 mL/sec.

87. A method according to claim 86 wherein said lipid composition is flushed at a rate of from about 0.3 to about 1.3 mL/sec.

88. A method for substantially eliminating ultrasound artifacts in an ultrasound image of an internal region of a patient comprising regulating the rate at which a contrast agent is administered to the patient, wherein said administration rate comprises continuous infusion.

89. A method according to claim 88 wherein said contrast agent comprises a vesicle composition comprising, in an aqueous carrier, a gas or gaseous precursor and vesicles comprising lipids.

90. A method according to claim 89 wherein said vesicle composition comprises vesicles selected from the group consisting of micelles and liposomes.

91. A method according to claim 89 wherein said lipids comprise phospholipids.

92. A method according to claim 91 wherein said phospholipids are selected from the group consisting of phosphatidylcholine, phosphatidylethanolamine and phosphatidic acid.

93. A method according to claim 92 wherein said phosphatidylcholine is selected from the group consisting of dioleoylphosphatidylcholine, dimyristoylphosphatidylcholine, dipalmitoylphosphatidylcholine and distearoylphosphatidylcholine.

94. A method according to claim 93 wherein said phosphatidylcholine comprises dipalmitoylphosphatidylcholine.

95. A method according to claim 92 wherein said phosphatidylethanolamine is selected from the group consisting of dipalmitoylphosphatidylethanolamine, dioleoylphosphatidylethanolamine, N-succinyldioleoylphosphatidylethanolamine and 1-hexadecyl-2-palmitoylglycerophosphoethanolamine.

96. A method according to claim 95 wherein said phosphatidylethanolamine comprises dipalmitoylphosphatidylethanolamine.

97. A method according to claim 92 wherein said phosphatidic acid comprises dipalmitolylphosphatidic acid.

98. A method according to claim 89 wherein said lipid further comprises a polymer.

99. A contrast agent according to claim 98 wherein said polymer comprises a hydrophilic polymer.

100. A method according to claim 99 wherein said hydrophilic polymer comprises polyethylene glycol.

101. A method according to claim 89 wherein said vesicle composition is administered to the patient at a rate of from about $1 \times 10^6$ to less than about $8 \times 10^6$ vesicles/Kg-sec.

102. A method according to claim 101 wherein said vesicle composition is administered at a rate of from about $1 \times 10^6$ to about $7 \times 10^6$ vesicles/Kg-sec.

103. A method according to claim 102 wherein said vesicle composition is administered at a rate of from about $1.5 \times 10^6$ to about $6 \times 10^6$ vesicles/Kg-sec.

104. A method according to claim 103 wherein said vesicle composition is administered at a rate of from about $2 \times 10^6$ to about $5.5 \times 10^6$ vesicles/Kg-sec.

105. A method according to claim 104 wherein said vesicle composition is administered at a rate of from about $2.5 \times 10^6$ to about $5 \times 10^6$ vesicles/Kg-sec.

106. A method according to claim 105 wherein said vesicle composition is administered at a rate of from about $3 \times 10^6$ to about $4.5 \times 10^6$ vesicles/Kg-sec.

107. A method according to claim 89 wherein said vesicle composition is administered to the patient at a rate of from about $1 \times 10^{-7}$ to about $3 \times 10^{-3}$ cc gas/Kg-sec.

108. A method according to claim 107 wherein said vesicle composition is administered at a rate of from about $3 \times 10^{-6}$ to about $3 \times 10^{-3}$ cc gas/Kg-sec.

109. A method according to claim 108 wherein said vesicle composition is administered at a rate of from about $4 \times 10^{-6}$ to about $2 \times 10^{-3}$ cc gas/Kg-sec.

110. A method according to claim 108 wherein said vesicle composition is administered at a rate of from about $8 \times 10^{-6}$ to about $2 \times 10^{-3}$ cc gas/Kg-sec.

111. A method according to claim 110 wherein said vesicle composition is administered at a rate of from about $1 \times 10^{-5}$ to about $1 \times 10^{-3}$ cc gas/Kg-sec.

112. A method according to claim 111 wherein said vesicle composition is administered at a rate of from about $4 \times 10^{-5}$ to about $1 \times 10^{-3}$ cc gas/Kg-sec.

113. A method according to claim 112 wherein said vesicle composition is administered at a rate of from about $8 \times 10^{-5}$ to less than about $1 \times 10^{-3}$ cc gas/Kg-sec.

114. A method according to claim 113 wherein said vesicle composition is administered at a rate of from about $1 \times 10^{-4}$ to about $9 \times 10^{-4}$ cc gas/Kg-sec.

115. A method according to claim 88 wherein said administration also comprises flushing said contrast agent.

116. A method according to claim 115 wherein said contrast agent is flushed at a rate of from about $1 \times 10^{-7}$ to about $3 \times 10^{-3}$ cc gas/Kg-sec.

117. A method according to claim 116 wherein said contrast agent is flushed at a rate of from about 0.05 to about 2 mL/sec.

118. A method according to claim 117 wherein said contrast agent is flushed at a rate of from about 0.07 to about 1.8 mL/sec.

119. A method according to claim 118 wherein said contrast agent is flushed at a rate of from about 0.09 to about 1.6 mL/sec.

120. A method according to claim 119 wherein said contrast agent is flushed at a rate of from about 0.1 to about 1.5 mL/sec.

121. A method according to claim 120 wherein said contrast agent is flushed at a rate of from about 0.3 to about 1.3 mL/sec.

122. A method according to claim 88 wherein the region comprises the heart region.

123. A method for diagnosing the presence of diseased tissue in a patient comprising (i) administering to the patient a vesicle composition comprising, in an aqueous carrier, a gas or gaseous precursor and vesicles comprising lipids, and (ii) scanning the patient using ultrasound imaging to obtain a visible image of any diseased tissue in the patient, wherein said vesicle composition is administered to the patient at a rate which substantially eliminates ultrasound artifacts in said image, wherein said administration rate comprises continuous infusion.

124. A method for diagnosing the presence of diseased tissue in a patient comprising (i) administering to the patient a lipid composition comprising, in an aqueous carrier, a lipid and a gas or gaseous precursor, and (ii) scanning the patient using ultrasound imaging to obtain a visible image of any diseased tissue in the patient, wherein said lipid composition is administered to the patient at a rate which substantially eliminates ultrasound artifacts in said image, wherein said administration rate comprises continuous infusion.

125. A method for diagnosing the presence of diseased tissue in a patient comprising (i) administering to the patient a vesicle composition comprising, in an aqueous carrier, a gas or gaseous precursor and vesicles comprising lipids, (ii) flushing said composition, and (iii) scanning the patient using ultrasound imaging to obtain a visible image of any diseased tissue in the patient, wherein said vesicle composition is flushed at a rate which substantially eliminates ultrasound artifacts in the image, wherein said flushing rate comprises continuous infusion.

126. A method for diagnosing the presence of diseased tissue in a patient comprising (i) administering to the patient a lipid composition comprising, in an aqueous carrier, a lipid and a gas or gaseous precursor, (ii) flushing said composition, and (iii) scanning the patient using ultrasound imaging to obtain a visible image of any diseased tissue in the patient, wherein said lipid composition is flushed at a rate which substantially eliminates ultrasound artifacts in the image, wherein said flushing rate comprises continuous infusion.

127. A method according to claim 2 wherein said vesicles comprise lipid-coated bubbles.

128. A method according to claim 127 wherein said vesicles are selected from the group consisting of unilamellar vesicles, oligolamellar vesicles and multilamellar vesicles.

129. A method according to claim 128 wherein said vesicles comprise unilamellar vesicles.

130. A method according to claim 129 wherein said vesicles comprise one monolayer.

131. A method according to claim 130 wherein said lipid is a phospholipid and said gas or gaseous precursor is perfluoropropane.

132. A method according to claim 129 wherein said vesicles comprise one bilayer.

133. A method according to claim 132 wherein said lipid is a phospholipid and said gas or gaseous precursor is perfluoropropane.

134. A method according to claim 128 wherein said vesicles are selected from the group consisting of oligolamellar vesicles and multilamellar vesicles.

135. A method according to claim 134 wherein said vesicles comprise one monolayer.

136. A method according to claim 135 wherein said lipid is a phospholipid and said gas or gaseous precursor is perfluoropropane.

137. A method according to claim 134 wherein said vesicles comprise one bilayer.

138. A method according to claim 137 wherein said lipid is a phospholipid and said gas or gaseous precursor is perfluoropropane.

139. A method according to claim 37 wherein said lipid is selected from the group consisting of unilamellar lipids, oligolamellar lipids or multilamellar lipids.

140. A method according to claim 139 wherein said lipid is a unilamellar lipid.

141. A method according to claim 140 wherein said unilamellar lipid comprises one monolayer.

142. A method according to claim 141 wherein said lipid is a phospholipid and said gas or gaseous precursor is perfluoropropane.

143. A method according to claim 141 wherein said lipid comprises one bilayer.

144. A method according to claim 143 wherein said lipid is a phospholipid and said gas or gaseous precursor is perfluoropropane.

145. A method according to claim 139 wherein said lipid is selected from the group consisting of oligolamellar lipids and multilamellar lipids.

146. A method according to claim 145 wherein said lipid comprises one monolayer.

147. A method according to claim 146 wherein said lipid is a phospholipid and said gas or gaseous precursor is perfluoropropane.

148. A method according to claim 145 wherein said lipid comprises one bilayer.

149. A method according to claim 148 wherein said lipid is a phospholipid and said gas or gaseous precursor is perfluoropropane.

150. A method according to claim 50 wherein said vesicles comprise lipid-coated bubbles.

151. A method according to claim 150 wherein said vesicles are selected from the group consisting of unilamellar vesicles, oligolamellar vesicles and multilamellar vesicles.

152. A method according to claim 151 wherein said lipids comprise a phospholipid.

153. A method according to claim 151 wherein said vesicles comprise unilamellar vesicles.

154. A method according to claim 153 wherein said vesicles comprise one monolayer.

155. A method according to claim 153 wherein said lipid is a phospholipid and said gas or gaseous precursor is perfluoropropane.

156. A method according to claim 153 wherein said vesicles comprise one bilayer.

157. A method according to claim 156 wherein said lipid is a phospholipid and said gas or gaseous precursor is perfluoropropane.

158. A method according to claim 157 wherein said vesicles are selected from the group consisting of oligolamellar vesicles and multilamellar vesicles.

159. A method according to claim 158 wherein said vesicles comprise one monolayer.

160. A method according to claim 159 wherein said lipid is a phospholipid and said gas or gaseous precursor is perfluoropropane.

161. A method according to claim 158 wherein said vesicles comprise one bilayer.

162. A method according to claim 161 wherein said lipid is a phospholipid and said gas or gaseous precursor is perfluoropropane.

163. A method according to claim 127 wherein said vesicles further comprise polyethylene glycol.

164. A method according to claim 150 wherein said vesicles further comprise polyethylene glycol.

165. A method according to claim 127 wherein said lipid is a phospholipid.

166. A method according to claim 130 wherein said lipid is a phospholipid.

167. A method according to claim 132 wherein said lipid is a phospholipid.

168. A method according to claim 135 wherein said lipid is a phospholipid.

169. A method according to claim 137 wherein said lipid is a phospholipid.

170. A method according to claim 141 wherein said lipid is a phospholipid.

171. A method according to claim 143 wherein said lipid is a phospholipid.

172. A method according to claim 146 wherein said lipid is a phospholipid.

173. A method according to claim 148 wherein said lipid is a phospholipid.

174. A method according to claim 154 wherein said lipid is a phospholipid.

175. A method according to claim 156 wherein said lipid is a phospholipid.

176. A method according to claim 159 wherein said lipid is a phospholipid.

177. A method according to claim 161 wherein said lipid is a phospholipid.

178. A method according to claim 1 wherein said composition is reconstructed from a lyophilized composition.

179. A method according to claim 2 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

180. A method according to claim 179 wherein said gas or gaseous precursor is a combination of nitrogen and perfluoropropane.

181. A method according to claim 37 wherein said composition is reconstituted from a lyophilized composition.

182. A method according to claim 37 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

183. A method according to claim 182 wherein said gas or gaseous precursor is a combination of nitrogen and perfluoropropane.

184. A method according to claim 50 wherein said composition is reconstituted from a lyophilized composition.

185. A method according to claim 51 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

186. A method according to claim 185 wherein said gas or gaseous precursor is a combination of nitrogen and perfluoropropane.

187. A method according to claim 76 wherein said composition is reconstituted from a lyophilized composition.

188. A method according to claim 76 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

189. A method according to claim 188 wherein said gas or gaseous precursor is a combination of nitrogen and perfluoropropane.

190. A method according to claim 89 wherein said composition is reconstituted from a lyophilized composition.

191. A method according to claim 89 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

192. A method according to claim 191 wherein said gas or gaseous precursor is a combination of nitrogen and perfluoropropane.

193. A method according to claim 123 wherein said composition is reconstituted from a lyophilized composition.

194. A method according to claim 123 wherein said vesicles comprise lipids and wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

195. A method according to claim 194 wherein said gas or gaseous precursor is a combination of nitrogen and perfluoropropane.

196. A method according to claim 124 wherein said composition is reconstituted from a lyophilized composition.

197. A method according to claim 124 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

198. A method according to claim 197 wherein said gas or gaseous precursor is a combination of nitrogen and perfluoropropane.

199. A method according to claim 125 wherein said composition is reconstituted from a lyophilized composition.

200. A method according to claim 125 wherein said vesicles comprise lipids and wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

201. A method according to claim 200 wherein said gas or gaseous precursor is a combination of nitrogen and perfluoropropane.

202. A method according to claim 126 wherein said composition is reconstituted from a lyophilized composition.

203. A method according to claim 126 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

204. A method according to claim 203 wherein said gas or gaseous precursor is a combination of nitrogen and perfluoropropane.

205. A method for providing an image of an internal region of a patient comprising (i) administering to the patient a vesicle composition comprising, in an aqueous carrier, a gas or gaseous precursor and vesicles comprising surfactants, and (ii) scanning the patient using ultrasound imaging to obtain a visible image of the region, wherein said vesicle composition is administered to the patient at a rate which substantially eliminates ultrasound artifacts in the image, wherein said administration rate comprises continuous infusion.

206. A method according to claim 205 wherein said composition is reconstituted from a lyophilized composition.

207. A method according to claim 205 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononanc.

208. A method according to claim 207 wherein said gas or gaseous precursor is a combination of nitrogen and perfluoropropane.

209. A method for providing an image of an internal region of a patient comprising (i) administering to the patient a composition comprising, in an aqueous carrier, a surfactant and a gas or gaseous precursor, and (ii) scanning the patient using ultrasound imaging to obtain a visible image of the region, wherein said composition is administered to the patient at a rate which substantially eliminates ultrasound artifacts in the image, wherein said administration rate comprises continuous infusion.

210. A method according to claim 209 wherein said composition is reconstituted from a lyophilized composition.

211. A method according to claim 209 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

212. A method according to claim 211 wherein said gas or gaseous precursor is a combination of nitrogen and perfluoropropane.

213. A method for providing an image of an internal region of a patient comprising (i) administering to the patient a vesicle composition comprising, in an aqueous carrier, a gas or gaseous precursor and vesicles comprising surfactants, (ii) flushing said composition, and (iii) scanning the patient using ultrasound imaging to obtain a visible image of the region, wherein said composition is flushed at a rate which substantially eliminates ultrasound artifacts in the image, wherein said flushing rate comprises continuous infusion.

214. A method according to claim 213 wherein said composition is reconstituted from a lyophilized composition.

215. A method according to claim 213 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

216. A method according to claim 215 wherein said gas or gaseous precursor is a combination of nitrogen and perfluoropropane.

217. A method for providing an image of an internal region of a patient comprising (i) administering to the patient a composition comprising, in an aqueous carrier, a surfactant and a gas or gaseous precursor, (ii) flushing said composition, and (iii) scanning the patient using ultrasound imaging to obtain a visible image of the region, wherein said composition is flushed at a rate which substantially eliminates ultrasound artifacts in the image, wherein said flushing rate comprises continuous infusion.

218. A method according to claim 217 wherein said composition is reconstituted from a lyophilized composition.

219. A method according to claim 217 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

220. A method according to claim 219 wherein said gas or gaseous precursor is a combination of nitrogen and perfluoropropane.

221. A method according to claim 88 wherein said contrast agent comprises a vesicle composition comprising, in an aqueous carrier, a gas or gaseous precursor and vesicles comprising surfactants.

222. A method according to claim 221 wherein said composition is reconstituted from a lyophilized composition.

223. A method according to claim 221 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

224. A method according to claim 223 wherein said gas or gaseous precursor is a combination of nitrogen and perfluoropropane.

225. A method for diagnosing the presence of diseased tissue in a patient comprising (i) administering to the patient a vesicle composition comprising, in an aqueous carrier, a gas or gaseous precursor and vesicles comprising surfactants, and (ii) scanning the patient using ultrasound imaging to obtain a visible image of any diseased tissue in the patient, wherein said vesicle composition is administered to the patient at a rate which substantially eliminates ultrasound artifacts in said image, wherein said administration rate comprises continuous infusion.

226. A method according to claim 225 wherein said composition is reconstituted from a lyophilized composition.

227. A method according to claim 225 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

228. A method according to claim 225 wherein said gas or gaseous precursor is a combination of nitrogen and perfluoropropane.

229. A method for diagnosing the presence of diseased tissue in a patient comprising (i) administering to the patient a composition comprising, in an aqueous carrier, a surfactant and a gas or gaseous precursor, and (ii) scanning the patient using ultrasound imaging to obtain a visible image of any diseased tissue in the patient, wherein said composition is administered to the patient at a rate which substantially eliminates ultrasound artifacts in said image, wherein said administration rate comprises continuous infusion.

230. A method according to claim 229 wherein said composition is reconstituted from a lyophilized composition.

231. A method according to claim 229 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

232. A method according to claim 231 wherein said gas or gaseous precursor is a combination of nitrogen and perfluoropropane.

233. A method for diagnosing the presence of diseased tissue in a patient comprising (i) administering to the patient a vesicle composition comprising, in an aqueous carrier, a gas or gaseous precursor and vesicles comprising surfactants, (ii) flushing said composition, and (iii) scanning the patient using ultrasound imaging to obtain a visible image of any diseased tissue in the patient, wherein said composition is flushed at a rate which substantially eliminates ultrasound artifacts in the image, wherein said flushing rate comprises continuous infusion.

234. A method according to claim 233 wherein said composition is reconstituted from a lyophilized composition.

235. A method according to claim 233 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

236. A method according to claim 235 wherein said gas or gaseous precursor is a combination of nitrogen and perfluoropropane.

237. A method for diagnosing the presence of diseased tissue in a patient comprising (i) administering to the patient a composition comprising, in an aqueous carrier, a surfactant and a gas or gaseous precursor, (ii) flushing said composition, and (iii) scanning the patient using ultrasound imaging to obtain a visible image of any diseased tissue in the patient, wherein said composition is flushed at a rate which substantially eliminates ultrasound artifacts in the image, wherein said flushing rate comprises continuous infusion.

238. A method according to claim 237 wherein said composition is reconstituted from a lyophilized composition.

239. A method according to claim 237 wherein said gas or gaseous precursor is selected from the group consisting of nitrogen, sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluoroheptane, perfluorooctane and perfluorononane.

240. A method according to claim 239 wherein said gas or gaseous precursor is a combination of nitrogen and perfluoropropane.

* * * * *

UNITED STATES PATENT AND TRADEMARK OFFICE
CERTIFICATE OF CORRECTION

PATENT NO. : 6,033,645
DATED : March 7, 2000
INVENTOR(S) : Unger et al.

It is certified that error appears in the above-identified patent and that said Letters Patent is hereby corrected as shown below:

<u>Title page,</u>
Item [56], U.S. PATENT DOCUMENTS,
At "4,352,500", please delete "4,352,500" and insert -- 3,532,500 -- therefor.
At "5,344,930", please delete "Piess et al." and insert -- Riess et al. -- therefor.
Please insert -- B1 4,229,360   11/1991   Schneider et al. ................260/403 --.

FOREIGN PATENT DOCUMENTS, Please delete "WO 84/02909" and insert
-- WO 94/02909 -- therefor.

OTHER PUBLICATIONS,
At "Ulendorf", first line thereof, please delete "Ulendorf" and insert -- Uhlendorf -- and, in third line thereof, please delete "*Ferrolectrics*" and insert
-- *Ferroelectrics* -- therefor.
At "Sekins et al.", second line thereof, after "Published", please add -- in <u>Proceedings of 5$^{th}$ International Symposium on Hyperthermia Oncology</u>, Kyoto, Japan, August 29-September 3, 1998, 3 pages
At "Hynynen et al.", please delete "Ysefulness" and insert -- Usefulness -- therefor.
At "Mayer et al.", please delete "PRoduced" and insert -- Produced -- therefor.
At "Shiina et al.", please delete "Hyperthermiaby" and insert -- Hyperthermia by- -- therefor.
At "Poznansky et al.", please delete "Biologica" and insert -- Biological -- therefor.
At "Ter-Pogossia", first line thereof, please delete "Ter-Pogossia *Tomography,* Kee, et al., n." and insert -- Ter-Pogossian --, and in second line thereof, after "*Computed Body*", please insert -- *Tomography,* Lee et al. -- therefor.
At "Aronberg", first line thereof, please delete "Kee" and insert -- Lee --, and in second line thereof, please delete "PRess" and insert -- Press -- therefor.
At "Elgorab et al.", please delete "Retinol in" and insert -- Retinol into -- therefor.
At "Keller et al.", fourth line thereof, please delete "458465" and insert
-- 458-465 -- therefor.
At "*Handbook of Pharmaceutical Excipients*", second and third lines thereof, please delete "Parmaceutical" and insert -- Pharmaceutical -- therefor.
At "Levene et al.," please delete "*acoust.*" and insert -- *Acoust.* -- therefor.

UNITED STATES PATENT AND TRADEMARK OFFICE
CERTIFICATE OF CORRECTION

PATENT NO. : 6,033,645
DATED : March 7, 2000
INVENTOR(S) : Unger et al.

It is certified that error appears in the above-identified patent and that said Letters Patent is hereby corrected as shown below:

Column 16,
Line 18, please delete "form" and insert -- from -- therefor.

Column 20,
Line 40, please delete "that about" and insert -- than about -- therefor.

Column 36,
Line 21, please delete "aobut" and insert -- about -- therefor.
Line 32, please delete "exhanger" and insert -- exchanger -- therefor, and, please delete "obatined" and insert -- obtained -- therefor.
Line 34, please delete "sonciation" and insert -- sonication -- therefor.
Line 49, please delete "sufficeint" and insert -- sufficient -- therefor.
Line 63, please delete "foaiming" and insert -- foaming -- therefor.

Column 37,
Line 11, please delete "gluteradehyde" and insert -- gluteraldehyde -- therefor.

Column 54,
Line 33, please delete "continuos" and insert -- continuous -- therefor.

Column 55,
Line 52, please delete "$8x10^6$" and insert -- $8x10^{-6}$ -- therefor.
Line 62, please delete "CC" and insert -- cc -- therefor.

Column 56,
Line 51, please delete "accroding" and insert -- according -- therefor, and, please delete "wherien" and insert -- wherein -- therefor.

Column 57,
Line 14, please delete "elected" and insert -- selected -- therefor.
Line 15, please delete "eptafluoropropane" and insert -- heptafluoropropane -- therefor.
Line 34, please delete "omprises" and insert -- comprises -- therefor.
Line 41, please delete "claims" and insert -- claim -- therefor.
Line 61, please delete "contiguous" and insert -- continuous -- therefor.

UNITED STATES PATENT AND TRADEMARK OFFICE
CERTIFICATE OF CORRECTION

PATENT NO.   : 6,033,645
DATED        : March 7, 2000
INVENTOR(S)  : Unger et al.

It is certified that error appears in the above-identified patent and that said Letters Patent is hereby corrected as shown below:

<u>Column 62,</u>
Line 25, please delete "reconstructed" and insert -- reconstituted -- therefor.

<u>Column 64,</u>
Line 17, please delete "perfluorononanc" and insert -- perfluorononane -- therefor.

Signed and Sealed this

Fifteenth Day of April, 2003

JAMES E. ROGAN
*Director of the United States Patent and Trademark Office*